(12) United States Patent
Cusey et al.

(10) Patent No.: US 11,819,324 B2
(45) Date of Patent: Nov. 21, 2023

(54) APPARATUS, SYSTEMS, AND METHODS FOR GATHERING AND PROCESSING BIOMETRIC AND BIOMECHANICAL DATA

(71) Applicant: NIKE, Inc., Beaverton, OR (US)

(72) Inventors: Lee Norman Cusey, Laguna Niguel, CA (US); Jay Allen Shears, Mission Viejo, CA (US); Harold Dan Stirling, Mission Viejo, CA (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 16/798,993

(22) Filed: Feb. 24, 2020

(65) Prior Publication Data

US 2020/0188735 A1    Jun. 18, 2020

Related U.S. Application Data

(63) Continuation of application No. 15/889,007, filed on Feb. 5, 2018, now Pat. No. 10,675,507, which is a
(Continued)

(51) Int. Cl.
*A61B 5/00* (2006.01)
*A63B 24/00* (2006.01)
(Continued)

(52) U.S. Cl.
CPC .............. *A61B 5/11* (2013.01); *A61B 5/1124* (2013.01); *A61B 5/22* (2013.01); *A61B 5/6802* (2013.01);
(Continued)

(58) Field of Classification Search
None
See application file for complete search history.

(56) References Cited

U.S. PATENT DOCUMENTS

| 4,273,216 A | 6/1981 | Weissmann |
| 4,502,035 A | 2/1985 | Obenauf et al. |

(Continued)

FOREIGN PATENT DOCUMENTS

| WO | WO-2004049943 A1 | 6/2004 |
| WO | WO-2004049944 A1 | 6/2004 |

(Continued)

OTHER PUBLICATIONS

"Apparatus, Systems, and Methods for Communicating Biometric and Biomechanical Information", Co-pending application assigned to the assignee of the current application: U.S. Appl. No. 11/601,445.
(Continued)

*Primary Examiner* — Damon J Pierce
(74) *Attorney, Agent, or Firm* — Schwegman, Lundberg & Woessner, P.A.

(57) ABSTRACT

Apparatus, systems, and methods are provided for measuring and analyzing movements of a body and for communicating information related to such body movements over a network. In certain embodiments, a system gathers biometric and biomechanical data relating to positions, orientations, and movements of various body parts of a user performed during sports activities, physical rehabilitation, or military or law enforcement activities. The biometric and biomechanical data can be communicated to a local and/or remote interface, which uses digital performance assessment tools to provide a performance evaluation to the user. The performance evaluation may include a graphical representation (e.g., a video), statistical information, and/or a comparison to another user and/or instructor. In some embodiments, the biometric and biomechanical data is communicated wirelessly to one or more devices including a processor, display, and/or data storage medium for further
(Continued)

analysis, archiving, and data mining. In some embodiments, the device includes a cellular telephone.

20 Claims, 25 Drawing Sheets

Related U.S. Application Data continuation of application No. 14/474,000, filed on Aug. 29, 2014, now Pat. No. 9,907,997, which is a continuation of application No. 13/369,686, filed on Feb. 9, 2012, now Pat. No. 8,821,305, which is a continuation of application No. 12/697,127, filed on Jan. 29, 2010, now abandoned, which is a continuation of application No. 12/488,491, filed on Jun. 19, 2009, now abandoned, which is a continuation of application No. 11/601,438, filed on Nov. 17, 2006, now Pat. No. 7,602,301.

(60) Provisional application No. 60/794,268, filed on Apr. 21, 2006, provisional application No. 60/781,612, filed on Mar. 10, 2006, provisional application No. 60/772,612, filed on Feb. 10, 2006, provisional application No. 60/765,382, filed on Feb. 3, 2006, provisional application No. 60/757,915, filed on Jan. 9, 2006.

(51) Int. Cl.
*A61B 5/11* (2006.01)
*A61B 5/22* (2006.01)
*A63B 5/11* (2006.01)
*A63B 69/36* (2006.01)
*G06F 3/01* (2006.01)
*G16H 40/67* (2018.01)
*G06V 40/20* (2022.01)
*G06F 18/00* (2023.01)
*G16H 20/30* (2018.01)
*G16H 80/00* (2018.01)

(52) U.S. Cl.
CPC ........ *A61B 5/6804* (2013.01); *A63B 24/0006* (2013.01); *A61B 5/1114* (2013.01); *A61B 5/1127* (2013.01); *A61B 5/4528* (2013.01); *A61B 5/6824* (2013.01); *A61B 5/7405* (2013.01); *A61B 2562/0219* (2013.01); *A63B 5/11* (2013.01); *A63B 24/0062* (2013.01); *A63B 69/3608* (2013.01); *A63B 69/3667* (2013.01); *A63B 2024/0012* (2013.01); *A63B 2209/08* (2013.01); *A63B 2209/10* (2013.01); *A63B 2220/10* (2013.01); *A63B 2220/13* (2013.01); *A63B 2220/24* (2013.01); *A63B 2220/30* (2013.01); *A63B 2220/40* (2013.01); *A63B 2220/803* (2013.01); *A63B 2220/836* (2013.01); *A63B 2225/20* (2013.01); *A63B 2225/50* (2013.01); *G06F 3/011* (2013.01); *G06F 18/00* (2023.01); *G06V 40/23* (2022.01); *G16H 20/30* (2018.01); *G16H 40/67* (2018.01); *G16H 80/00* (2018.01)

(56) References Cited

U.S. PATENT DOCUMENTS

| | | |
|---|---|---|
| 4,582,325 A | 4/1986 | Yuhara |
| 4,660,829 A | 4/1987 | Whiteneir |
| 4,665,928 A | 5/1987 | Linial et al. |
| 4,966,154 A | 10/1990 | Cooper et al. |
| 5,067,717 A | 11/1991 | Harlan et al. |
| 5,221,088 A | 6/1993 | McTeigue et al. |
| 5,229,756 A | 7/1993 | Kosugi et al. |
| 5,375,610 A | 12/1994 | LaCourse et al. |
| 5,492,118 A | 2/1996 | Gratton et al. |
| 5,511,789 A | 4/1996 | Nakamura |
| 5,524,637 A | 6/1996 | Erickson |
| 5,592,401 A | 1/1997 | Kramer |
| 5,638,300 A | 6/1997 | Johnson |
| 5,679,004 A | 10/1997 | Mcgowan et al. |
| 5,702,323 A | 12/1997 | Poulton |
| 5,714,698 A | 2/1998 | Tokioka et al. |
| 5,724,265 A | 3/1998 | Hutchings |
| 5,791,351 A | 8/1998 | Curchod |
| 5,826,578 A | 10/1998 | Curchod |
| 5,899,963 A | 5/1999 | Hutchings |
| 5,907,819 A | 5/1999 | Johnson |
| 5,919,149 A | 7/1999 | Allum |
| 5,930,741 A | 7/1999 | Kramer |
| 5,961,474 A | 10/1999 | Reis |
| 5,963,891 A | 10/1999 | Walker et al. |
| 5,984,796 A | 11/1999 | Mah |
| 6,005,548 A | 12/1999 | Latypov et al. |
| 6,050,962 A | 4/2000 | Kramer et al. |
| 6,050,963 A | 4/2000 | Johnson et al. |
| 6,061,611 A | 5/2000 | Whitmore |
| 6,066,075 A | 5/2000 | Poulton |
| 6,072,467 A | 6/2000 | Walker |
| 6,088,042 A | 7/2000 | Handelman et al. |
| 6,122,960 A | 9/2000 | Hutchings et al. |
| 6,148,280 A | 11/2000 | Kramer |
| 6,165,143 A | 12/2000 | van Lummel |
| 6,176,837 B1 | 1/2001 | Foxlin |
| D439,981 S | 4/2001 | Kasabach et al. |
| 6,261,189 B1 | 7/2001 | Saville et al. |
| 6,305,221 B1 | 10/2001 | Hutchings |
| 6,308,565 B1 | 10/2001 | French et al. |
| 6,314,055 B1 | 11/2001 | Foxlin et al. |
| D451,604 S | 12/2001 | Kasabach et al. |
| 6,377,281 B1 | 4/2002 | Rosenbluth et al. |
| D460,971 S | 7/2002 | Sica et al. |
| 6,428,490 B1 | 8/2002 | Kramer et al. |
| 6,454,708 B1 | 9/2002 | Ferguson et al. |
| 6,463,385 B1 | 10/2002 | Fry |
| 6,474,159 B1 | 11/2002 | Foxlin et al. |
| 6,515,669 B1 | 2/2003 | Mohri |
| 6,527,711 B1 | 3/2003 | Stivoric et al. |
| 6,567,536 B2 | 5/2003 | Mcnitt et al. |
| 6,571,193 B1 | 5/2003 | Unuma et al. |
| 6,590,536 B1 | 7/2003 | Walton |
| 6,595,929 B2 | 7/2003 | Stivoric et al. |
| 6,605,038 B1 | 8/2003 | Teller et al. |
| 6,636,826 B1 | 10/2003 | Abe et al. |
| 6,646,643 B2 | 11/2003 | Templeman |
| 6,681,629 B2 | 1/2004 | Foxlin et al. |
| 6,682,351 B1 | 1/2004 | Abraham-fuchs et al. |
| 6,757,068 B2 | 6/2004 | Foxlin |
| 6,771,224 B2 | 8/2004 | Apostolos |
| 6,778,866 B1 | 8/2004 | Bettwy |
| 6,820,025 B2 | 11/2004 | Bachmann et al. |
| 6,826,509 B2 | 11/2004 | Crisco, III et al. |
| 6,828,908 B2 | 12/2004 | Clark |
| 6,834,436 B2 | 12/2004 | Townsend et al. |
| 6,909,420 B1 | 6/2005 | Nicolas et al. |
| 6,922,632 B2 | 7/2005 | Foxlin |
| 6,959,259 B2 | 10/2005 | Vock et al. |
| 7,000,469 B2 | 2/2006 | Foxlin et al. |
| 7,171,331 B2 | 1/2007 | Vock et al. |
| 7,210,240 B2 | 5/2007 | Townsend et al. |
| 7,219,033 B2 | 5/2007 | Kolen |
| 7,261,690 B2 | 8/2007 | Teller et al. |
| 7,264,554 B2 | 9/2007 | Bentley |
| 7,271,825 B2 | 9/2007 | Dara-abrams |
| 7,292,151 B2 | 11/2007 | Ferguson et al. |
| 7,334,472 B2 | 2/2008 | Seo et al. |
| 7,365,647 B2 | 4/2008 | Nativ |
| 7,433,798 B2 | 10/2008 | Townsend et al. |
| 7,494,430 B2 | 2/2009 | Choi |
| 7,503,878 B1 | 3/2009 | Amsbury et al. |
| 7,542,040 B2 | 6/2009 | Templeman |

(56) References Cited

U.S. PATENT DOCUMENTS

| | | |
|---|---|---|
| 7,554,549 B2 | 6/2009 | Sagar et al. |
| 7,602,301 B1 | 10/2009 | Stirling et al. |
| 7,625,316 B1 | 12/2009 | Amsbury et al. |
| 7,627,451 B2 | 12/2009 | Vock et al. |
| 7,670,263 B2 | 3/2010 | Ellis et al. |
| 7,689,378 B2 | 3/2010 | Kolen |
| 7,689,437 B1 | 3/2010 | Teller et al. |
| 7,755,602 B2 | 7/2010 | Tremblay et al. |
| 7,821,407 B2 | 10/2010 | Shears et al. |
| 7,825,815 B2 | 11/2010 | Shears et al. |
| 7,978,081 B2 | 7/2011 | Shears et al. |
| 8,821,305 B2 | 9/2014 | Cusey et al. |
| 9,907,997 B2 | 3/2018 | Cusey et al. |
| 10,675,507 B2 | 6/2020 | Cusey et al. |
| 11,399,758 B2 | 8/2022 | Cusey et al. |
| 11,452,914 B2 | 9/2022 | Cusey et al. |
| 2002/0077189 A1 | 6/2002 | Tuer et al. |
| 2002/0115047 A1 | 8/2002 | Mcnitt et al. |
| 2002/0143277 A1 | 10/2002 | Wood et al. |
| 2002/0170193 A1* | 11/2002 | Townsend ............. A61B 5/1116 33/512 |
| 2002/0194914 A1 | 12/2002 | Foxlin et al. |
| 2003/0035342 A1 | 2/2003 | Harrington et al. |
| 2003/0083596 A1 | 5/2003 | Kramer et al. |
| 2003/0163287 A1 | 8/2003 | Vock |
| 2003/0216228 A1 | 11/2003 | Rast |
| 2004/0070534 A1 | 4/2004 | Halsey et al. |
| 2004/0073360 A1 | 4/2004 | Foxlin |
| 2004/0113771 A1 | 6/2004 | Ozaki et al. |
| 2004/0116836 A1 | 6/2004 | Kawai et al. |
| 2004/0149036 A1 | 8/2004 | Foxlin et al. |
| 2004/0201857 A1 | 10/2004 | Foxlin |
| 2004/0219498 A1 | 11/2004 | Davidson |
| 2004/0243148 A1 | 12/2004 | Wasielewski |
| 2005/0010139 A1 | 1/2005 | Aminian et al. |
| 2005/0027216 A1 | 2/2005 | Guillemaud et al. |
| 2005/0037844 A1 | 2/2005 | Shum et al. |
| 2005/0059489 A1 | 3/2005 | Kim |
| 2005/0113167 A1* | 5/2005 | Buchner ................. A63F 13/02 463/30 |
| 2005/0186938 A1 | 8/2005 | Hunter |
| 2005/0231425 A1 | 10/2005 | Coleman et al. |
| 2005/0240086 A1 | 10/2005 | Akay |
| 2005/0240253 A1 | 10/2005 | Tyler et al. |
| 2005/0250440 A1 | 11/2005 | Zhou et al. |
| 2005/0280531 A1 | 12/2005 | Fadem et al. |
| 2005/0282633 A1 | 12/2005 | Nicolas et al. |
| 2006/0004299 A1 | 1/2006 | Endo et al. |
| 2006/0027404 A1 | 2/2006 | Foxlin |
| 2006/0031102 A1 | 2/2006 | Teller et al. |
| 2006/0135883 A1 | 6/2006 | Jónsson |
| 2006/0155183 A1 | 7/2006 | Kroecker et al. |
| 2006/0158329 A1 | 7/2006 | Burkley et al. |
| 2006/0166737 A1 | 7/2006 | Bentley |
| 2006/0189852 A1 | 8/2006 | Greenwald et al. |
| 2006/0284979 A1 | 12/2006 | Clarkson |
| 2007/0027367 A1 | 2/2007 | Oliver et al. |
| 2007/0032748 A1 | 2/2007 | McNeil et al. |
| 2007/0039387 A1 | 2/2007 | Jouanet et al. |
| 2007/0135225 A1 | 6/2007 | Nieminen |
| 2007/0167879 A1 | 7/2007 | Cochran |
| 2007/0208542 A1 | 9/2007 | Vock et al. |
| 2007/0219744 A1 | 9/2007 | Kolen |
| 2007/0250286 A1 | 10/2007 | Duncan et al. |
| 2008/0214963 A1 | 9/2008 | Guillemaud et al. |
| 2008/0285805 A1 | 11/2008 | Luinge et al. |
| 2009/0149721 A1* | 6/2009 | Yang ...................... A61B 5/165 600/301 |
| 2009/0278791 A1 | 11/2009 | Slycke et al. |
| 2010/0035688 A1 | 2/2010 | Picunko |
| 2010/0117837 A1 | 5/2010 | Stirling et al. |
| 2010/0121227 A1 | 5/2010 | Stirling et al. |
| 2010/0121228 A1 | 5/2010 | Stirling et al. |
| 2010/0201500 A1 | 8/2010 | Stirling et al. |
| 2010/0204616 A1 | 8/2010 | Shears et al. |
| 2011/0109438 A1 | 5/2011 | Dijkstra et al. |
| 2012/0143093 A1 | 6/2012 | Stirling et al. |
| 2016/0038787 A1 | 2/2016 | Cusey et al. |
| 2018/0290021 A1 | 10/2018 | Cusey et al. |
| 2020/0368579 A1 | 11/2020 | Cusey et al. |
| 2020/0376338 A1 | 12/2020 | Cusey et al. |
| 2020/0391078 A1 | 12/2020 | Cusey et al. |
| 2020/0391079 A1 | 12/2020 | Cusey et al. |

FOREIGN PATENT DOCUMENTS

| | | |
|---|---|---|
| WO | WO-2004084725 A1 | 10/2004 |
| WO | WO-2007069014 A1 | 6/2007 |
| WO | WO-2008061023 A2 | 5/2008 |

OTHER PUBLICATIONS

"Apparatus, Systems, and Methods for Evaluating Body Movements", Co-pending application assigned to the assignee of the current application: U.S. Appl. No. 11/601,381.

"Apparatus, Systems, and Methods for Gathering and Processing Biometric and Biomechanical Data", Co-pending application assigned to the assignee of the current application: U.S. Appl. No. 12/697,127.

"Apparatus, Systems, and Methods for Gathering and Processing Biometric and Biomechanical Data", Co-pending application assigned to the assignee of the current application: U.S. Appl. No. 12/697,151.

"Apparatus, Systems, and Methods for Gathering and Processing Biometric and Biomechanical Data", Co-pending application assigned to the assignee of the current application: U.S. Appl. No. 12/697,180.

"Apparatus, Systems, and Methods for Gathering and Processing Biometric and Biomechanical Data", Co-pending application assigned to the assignee of the current application: U.S. Appl. No. 12/488,491.

"Apparatus, Systems, and Methods for Gathering and Processing Biometric and Biomechanical Data", Co-pending application assigned to the assignee of the current application: U.S. Appl. No. 11/601,438.

"Apparatus, Systems, and Methods for Gathering and Processing Biometric and Biomechanical Data", Application assigned to the assignee of the current application: U.S. Appl. No. 13/369,686.

"U.S. Appl. No. 11/601,438, Non Final Office Action dated Dec. 4, 2008", 12 pgs.

"U.S. Appl. No. 11/601,438, Notice of Allowance dated Jun. 17, 2009", 8 pgs.

"U.S. Appl. No. 11/601,438, Notice of Allowance dated Jul. 27, 2009", 4 pgs.

"U.S. Appl. No. 11/601,438, Notice of Allowance dated Sep. 10, 2009", 2 pgs.

"U.S. Appl. No. 11/601,438, Response filed Mar. 19, 2009 to Non Final Office Action dated Dec. 4, 2008", 8 pgs.

"U.S. Appl. No. 11/601,445, Examiner Interview Summary dated Apr. 9, 2010", 3 pgs.

"U.S. Appl. No. 11/601,445, Non Final Office Action dated Dec. 2, 2009", 12 pgs.

"U.S. Appl. No. 11/601,445, Notice of Allowance dated Mar. 1, 2011", 8 pgs.

"U.S. Appl. No. 11/601,445, Response filed Apr. 23, 2010 to Non Final Office Action dated Dec. 2, 2009", 13 pgs.

"U.S. Appl. No. 11/601,445, Response filed Oct. 7, 2009 to Restriction Requirement dated Sep. 25, 2009", 8 pgs.

"U.S. Appl. No. 11/601,445, Restriction Requirement dated Sep. 25, 2009", 7 pgs.

"U.S. Appl. No. 12/488,491, Non Final Office Action dated Oct. 26, 2010", 19 pgs.

"U.S. Appl. No. 12/697,127, Examiner Interview Summary dated Sep. 9, 2011", 2 pgs.

"U.S. Appl. No. 12/697,127, Non Final Office Action dated Aug. 9, 2011", 5 pgs.

"U.S. Appl. No. 12/697,127, Response filed Jul. 5, 2011 to Restriction Requirement dated Jan. 4, 2011", 10 pgs.

"U.S. Appl. No. 12/697,127, Restriction Requirement dated Jan. 4, 2011", 6 pgs.

"U.S. Appl. No. 12/697,151, Applicant's Summary of Examiner Interview filed Aug. 2, 2010", 3 pgs.

(56) References Cited

OTHER PUBLICATIONS

"U.S. Appl. No. 12/697,151, Non Final Office Action dated May 6, 2010", 12 pgs.
"U.S. Appl. No. 12/697,151, Notice of Allowance dated Jul. 6, 2010", 11 pgs.
"U.S. Appl. No. 12/697,180, Applicant's Summary of Examiner Interview filed Aug. 2, 2010", 3 pgs.
"U.S. Appl. No. 12/697,180, Notice of Allowance dated Jul. 1, 2010", 14 pgs.
"U.S. Appl. No. 13/369,686, Non Final Office Action dated Sep. 13, 2012", 16 pgs.
"U.S. Appl. No. 13/369,686, Non Final Office Action dated Oct. 11, 2013", 6 pgs.
"U.S. Appl. No. 13/369,686, Notice of Allowance dated Apr. 28, 2014", 7 pgs.
"U.S. Appl. No. 13/369,686, Response filed Mar. 12, 2013 to Non Final Office Action dated Sep. 13, 2012", 17 pgs.
"U.S. Appl. No. 13/369,686, Response filed Apr. 8, 2014 to Non Final Office Action dated Oct. 11, 2013", 13 pgs.
"U.S. Appl. No. 14/474,000, Non Final Office Action dated Mar. 15, 2017", 14 pgs.
"U.S. Appl. No. 14/474,000, Notice of Allowance dated Oct. 19, 2017", 8 pgs.
"U.S. Appl. No. 14/474,000, Response filed Aug. 14, 2017 to Non Final Office Action dated Mar. 15, 2017", 9 pgs.
"U.S. Appl. No. 14/474,000, Response filed Dec. 28, 2016 to Restriction Requirement dated Jul. 1, 2016", 6 pgs.
"U.S. Appl. No. 14/474,000, Restriction Requirement dated Jul. 1, 2016", 6 pgs.
"U.S. Appl. No. 15/889,007, Examiner Interview Summary dated Jan. 28, 2020", 3 pgs.
"U.S. Appl. No. 15/889,007, Examiner Interview Summary dated Sep. 11, 2019", 3 pgs.
"U.S. Appl. No. 15/889,007, Final Office Action dated Dec. 12, 2019", 14 pgs.
"U.S. Appl. No. 15/889,007, Non Final Office Action dated May 15, 2019", 15 pgs.
"U.S. Appl. No. 15/889,007, Preliminary Amendment filed Jun. 22, 2018", 5 pgs.
"U.S. Appl. No. 15/889,007, Response filed Feb. 11, 2020 to Final Office Action dated Dec. 12, 2019", 14 pgs.
"U.S. Appl. No. 15/889,007, Response filed Oct. 15, 2019 to Non-Final Office Action dated May 15, 2019", 19 pgs.
"Arik Hesseldahl and Stanley Holmes", Apple and Nike, Running Mates, Business Week, (May 24, 2006).
Cheok, et al., "Interactive Theatre Experience in Embodied—Wearable Mixed Reality Space", Proceeding of the International Symposium on Mixed and Augmented Reality, (2002), 10 pgs.
Christian, et al., "Gathering Motion Data using Featherweight Sensors and TCP-IP over 802.15.4", IEEE International Symposium on Wearable Computing, Workshop on On-Body Sensing, Osaka, Japan, (Oct. 18-21, 2005), 4 pgs.
David, Churchill, "Quantification of Human Knee Kinematics Using the 3DM-GX1 Sensor", [Online] Retrieved from the internet: <www.microstrain.com>, (Jan. 2004), 12 pgs.
Denjabadi, et al., "Estimation and Visualization of Sagittal Kinematics of Lower Limbs Orientation Using Body-Fixed Sensors", IEEE Transactions on Biomedical Engineering, vol. 53, No. 7, (Jul. 2006), 1385-1393.
Eric, Robert Bachmann, "Inertial and Magnetic Tracking of Limb Segment Orientation for Inserting Humans into Synthetic Environments", Naval Postgraduate School Dissertation, (Dec. 2000), 197 pgs.
Faruk, Yildiz, "Implementation of a Human Avatar for the Mar G Project in Networked Virtual Environments", Naval Postgraduate School, Monterey, California, (Mar. 2004).
Ildeniz, Duman, "Thesis, Design, Implementation, and Testing of a Real-Time Software System for a Quaternion-Based Attitude Estimation Filter", Naval Postgraduate School, Monterey, California, (Mar. 1999).

Ilmonen, et al., "Software Architecture for Multimodal User Input—Fluid, Helsinki University of Technology Telecommunications Software and Multimedia Library", User Interfaces for All, LNCS 2615, (2003), 319-338.
Jovanov, et al., "A wireless body area network of intelligent motion sensors for computer assisted physical rehabilitation", Journal of NeuroEngineering and Rehabilitation 2:6, (Mar. 2005), 10 pgs.
Lane, et al., "Control Interface for Driving Interactive Characters in Immersive Virtual Environments", US Army Research, Report, (Nov. 2006), 10 pgs.
Otto, et al., "System Architecture of a Wireless Body Area Sensor Network for Ubiquitous Health Monitoring", University of Alabama in Huntsville, Journal of Mobile Multimedia, vol. 1, No. 4, (2006), 307-326.
Reed, Albergotti, "Golfs Digital Divide", The Wall Street Journal, (Apr. 8,9, 2006).
Takemura, et al., "Distributed Processing Architecture for Virtual Space Teleconferencing", Proceedings of International Conference on Artificial Reality and Telexistence, ICAT'93, (Jul. 1993), 27-32.
Vadym, Crygorenko, "Digital Compassing: Build a Tilt-Compensated Digital Magnetic Compass", (Mar. 2006).
Vesna, Filipovic, et al., "SYDACK—System of Diagnosis and Control in Kinesitherapy", 28th International Conference Information Technology Interfaces ITI 206, Cavtat, Croatia, (Jun. 19-22, 2006), 6 pgs.
"U.S. Appl. No. 15/889,007, Notice of Allowance dated Feb. 27, 2020", 9 pgs.
"U.S. Appl. No. 16/989,383, Preliminary Amendment filed Aug. 11, 2020", 8 pgs.
"U.S. Appl. No. 16/989,400, Preliminary Amendment filed Aug. 11, 2020", 9 pgs.
"U.S. Appl. No. 17/003,249, Preliminary Amendment filed Aug. 27, 2020", 8 pgs.
"U.S. Appl. No. 17/003,273, Preliminary Amendment filed Aug. 27, 2020", 8 pgs.
"U.S. Appl. No. 16/989,383, Non Final Office Action dated Jan. 11, 2022", 14 pgs.
"U.S. Appl. No. 16/989,400, Non Final Office Action dated Jan. 12, 2022", 6 pgs.
"U.S. Appl. No. 17/003,249, Non Final Office Action dated Jan. 26, 2022", 12 pgs.
"NPL Search", (Jan. 19, 2022).
"NPL Search", (Jan. 8, 2022).
"NPL Search", (Jan. 6, 2021).
"U.S. Appl. No. 16/989,383, Final Office Action dated May 13, 2022", 17 pgs.
"U.S. Appl. No. 16/989,383, Response filed Mar. 18, 2022 to Non Final Office Action dated Jan. 11, 2022", 12 pgs.
"U.S. Appl. No. 16/989,400, Notice of Allowance dated Apr. 18, 2022", 8 pgs.
"U.S. Appl. No. 16/989,400, Response filed Mar. 18, 2022 to Non Final Office Action dated Jan. 12, 2022", 8 pgs.
"U.S. Appl. No. 16/989,400, Supplemental Notice of Allowability dated Jul. 1, 2022", 2 pgs.
"U.S. Appl. No. 17/003,249, Notice of Allowance dated Jun. 2, 2022", 7 pgs.
"U.S. Appl. No. 17/003,249, Response filed Apr. 26, 2022 to Non Final Office Action dated Jan. 26, 2022", 10 pgs.
"U.S. Appl. No. 17/003,249, Supplemental Notice of Allowability dated Jun. 23, 2022", 2 pgs.
"U.S. Appl. No. 17/003,273, Examiner Interview Summary dated Apr. 18, 2022", 2 pgs.
"U.S. Appl. No. 17/003,273, Non Final Office Action dated Mar. 16, 2022", 12 pgs.
"U.S. Appl. No. 17/003,273, Response filed Sep. 12, 2022 to Non Final Office Action dated Mar. 16, 2022", 14 pgs.
"U.S. Appl. No. 16/989,383, Notice of Allowance dated Jan. 25, 2023", 7 pgs.
"U.S. Appl. No. 16/989,383, Response filed Oct. 6, 2022 to Final Office Action dated May 13, 2022", 13 pgs.
"U.S. Appl. No. 17/003,273, Final Office Action dated Nov. 16, 2022", 12 pgs.

(56) References Cited

OTHER PUBLICATIONS

"U.S. Appl. No. 17/003,273, Notice of Allowance dated Mar. 24, 2023", 8 pgs.
"U.S. Appl. No. 17/003,273, Response filed Feb. 16, 2023 to Final Office Action dated Nov. 16, 2022", 16 pgs.

* cited by examiner

APPARATUS, SYSTEMS, AND METHODS FOR GATHERING AND PROCESSING BIOMETRIC AND BIOMECHANICAL DATA

CROSS-REFERENCE TO RELATED APPLICATIONS

This application is a continuation of U.S. patent application Ser. No. 15/889,007, filed Feb. 5, 2018, which application is a continuation of U.S. application Ser. No. 14/474,000 filed Aug. 29, 2014, titled "APPARATUS, SYSTEMS, AND METHODS FOR GATHERING AND PROCESSING BIOMETRIC AND BIOMECHANICAL DATA" which is a continuation of U.S. application Ser. No. 13/369,686 filed Feb. 9, 2012, now issued as U.S. Pat. No. 8,821,305 titled "APPARATUS, SYSTEMS, AND METHODS FOR GATHERING AND PROCESSING BIOMETRIC AND BIOMECHANICAL DATA", which is a continuation of U.S. application Ser. No. 12/697,127 filed Jan. 29, 2010 titled "APPARATUS, SYSTEMS, AND METHODS FOR GATHERING AND PROCESSING BIOMETRIC AND BIOMECHANICAL DATA", which is a continuation of U.S. application Ser. No. 12/488,491, filed Jun. 19, 2009, titled "APPARATUS, SYSTEMS AND METHODS FOR GATHERING AND PROCESSING BIOMETRIC AND BIOMECHANICAL DATA", which is a continuation of U.S. application Ser. No. 11/601,438, filed Nov. 17, 2006, and now issued as U.S. Pat. No. 7,602,301, titled "APPARATUS, SYSTEMS, AND METHODS FOR GATHERING AND PROCESSING BIOMETRIC AND BIOMECHANICAL DATA", which claims the benefit of priority under 35 U.S.C. § 119(e) to each of the following provisional patent applications: U.S. Provisional Patent Application No. 60/757,915, filed Jan. 9, 2006, titled "APPARATUS, SYSTEMS AND METHODS FOR FATHERING AND PROCESSING BIOMETRIC DATA"; U.S. Provisional Patent Application No. 60/765,382, filed Feb. 3, 2006, titled "APPARATUS, SYSTEMS AND METHODS FOR GATHERING AND PROCESING BIOMETRIC DATA"; U.S. Provisional Patent Application No. 60/772,612, filed Feb. 10, 2006, titled "APPARATUS, SYSTEMS AND METHODS FOR FATHERING AND PROCESSING BIOMETRIC DATA"; U.S. Provisional Patent Application No. 60/781,612, filed Mar. 10, 2006, titled "APPARATUS, SYSTEMS AND METHODS FOR FATHERING AND PROCESSING BIOMETRIC DATA"; and U.S. Provisional Patent Application No. 60/794,268, filed Apr. 21, 2006, titled "APPARATUS, SYSTEMS, AND METHODS FOR GATHERING AND PROCESSING BIOMETRIC AND BIOMECHANICAL DATA". The entirety of each of the above-listed documents is hereby incorporated by reference herein, and each is hereby made a part of this specification.

BACKGROUND OF THE DISCLOSURE

Field of the Disclosure

The present disclosure relates to apparatus, systems, and methods for measuring and analyzing movements of a body and for communicating information related to such body movements over a network.

Description of the Related Art

Participants in sports, athletics, and recreational activities often desire to measure their progress relative to their earlier performance or to a performance benchmark such as a famous athlete. Coaches and trainers may desire to monitor the performance of a player or a team as a whole. Medical patients who have suffered an injury that restricts movement of a limb or joint may desire to track their improvement during rehabilitation, and an attending health care provider may desire an object measurement of the improvement.

Sensors can be attached to portions of the body to measure body movements. Data from the sensors can be analyzed to determine characteristics of the body movement (e.g., a range of motion). In some cases, the player or the patient is at one location where he or she performs movements measured by the sensors, while the coach or health care provider is at another location distant from the player or patient. In such cases, it may be inconvenient or difficult to communicate sensor measurements to the coach or healthcare provider resulting in delays in coaching instruction or diagnosis. The present disclosure addresses this and other problems.

SUMMARY OF THE DISCLOSURE

Various non-limiting embodiments of apparatus, systems, and methods for gathering and processing biometric and biomechanical data are disclosed herein. An embodiment of a body movement sensor system comprises at least two sensors associated with an appendage of a user and a transceiver configured to accompany the user during a sports activity. The transceiver is further configured to communicate with the sensors and transmit data received from the sensors. The system also comprises a first processor that is configured to remotely receive the data from the sensors and process the data. The first processor has an interface to illustrate characteristics of the user's performance in real time. The system also comprises a second processor configured to receive and store the data for research or archival purposes.

In an embodiment of the body movement sensor system, at least one of the sensors comprises a three-axis sensor. For example, the three-axis sensor can comprise a three-axis accelerometer, a three-axis magnetometer, and/or a three-axis gyroscopic detector. In some embodiments, at least one of the sensors is substantially water resistant.

In some embodiments of the body movement sensor system, at least one of the sensors is associated with an appendage of a user using a hook and loop material. In certain embodiments of the system, least one of the sensors is associated with an appendage of a user by being attached to a garment. In certain such embodiments, the garment is configured not to substantially interfere with movements of the user during the sports activity. Also, in certain such embodiments, the garment is configured to substantially conform to the appendage of the user.

In various embodiments of the body movement sensor system, the sensors are configured to substantially maintain their orientation and position relative to the appendage during the sports activity. In certain embodiments of the body movement sensor system, the appendage comprises a portion of an arm and/or a leg.

In certain embodiments of the body movement sensor system, the transceiver is further configured to communicate with the sensors through wires. In other embodiments, the transceiver is further configured to communicate with the sensors wirelessly. In an embodiment of the body movement sensor system, the system further comprises at least four sensors, two of which are associated with a leg and two others of which are associated with an arm of a user.

In certain embodiments of the body movement sensor system, the first processor is disposed in a cellular telephone. In certain such embodiments, the first processor comprises the cellular telephone. In some embodiments of the body movement sensor system, the second processor is configured to store received data in a short-term data storage device and to transfer at least some of the received data from the short-term data storage device to a long-term data storage device for the archival purposes. In certain such embodiments, the second processor is configured to transfer at least some of the received data after the data has been stored in the short-term data storage device for a threshold time. In some embodiments of the system, the data is organized for efficient communication over a wireless channel.

In some embodiments of the system, the research purposes comprise extracting implicit, previously unknown, and potentially useful information. In certain embodiments of the system, the research purposes comprise medical research related to body movements.

An embodiment of a measurement system is disclosed. The measurement system comprises at least one sensor configured to associate with a body portion and output data relating to the body portion. The system also comprises a first processor configured to receive and process the data, a second processor configured to receive and process the data, and a transceiver configured to communicate with the sensor and communicate wirelessly with the first processor and the second processor. The data is organized for efficient communication over a wireless channel.

In some embodiments of the measurement system, the data comprises a plurality of packets having an ID header and a packet length. In some such embodiments, the packet length is selected to efficiently utilize a bandwidth of the wireless channel. In one embodiment, the packet length is about 1 second.

Another embodiment of a measurement system is disclosed. In this embodiment, the measurement system comprises at least one sensor configured to associate with a body portion and output data relating to the body portion. This system also includes a first processor configured to receive and process the data, a second processor configured to receive and process the data, and a transceiver configured to communicate with the sensor and communicate wirelessly with the first processor and the second processor. In this embodiment, the at least one sensor is configured to operate at a sample rate that is adjustable.

In some embodiments of this measurement system, the sample rate is adjusted by the transceiver, the first processor, or the second processor. In another embodiment of the system, the sample rate may be adjusted by a user. In certain embodiments of the system, the sample rate is in a range from about 1 Hz to about 10 kHz. In some embodiments, the sample rate is about 2 kHz. In various embodiments of the measurement system, the sample rate can correspond to a Nyquist sample rate for motion of the body part to which the sensor is associated. In certain embodiments, at least one of the first processor and the second processor comprises a cellular telephone.

A further embodiment of a measurement system, is disclosed herein. This measurement system comprises at least one sensor configured to associate with a body portion and to output data relating to the body portion. The system also includes a first processor configured to receive and process the data, a second processor configured to receive and process the data, and a transceiver configured to communicate with the sensor and communicate wirelessly with the first processor and the second processor. The data is stored by a storage system.

In some embodiments of this measurement system, the system further comprises a third processor configured to search the data stored in the storage system. In some of these embodiments, the third processor is configured to extract from the data stored in the storage system implicit, previously unknown, and potentially useful information. In certain embodiments of the measurement system, the storage system comprises a short-term storage system configured to store data having an age less than a threshold, and a long-term storage system configured to store data having an age greater than the threshold.

An embodiment of a body movement monitoring system comprises body movement sensors configured to sense and transmit data relating to at least one of position, orientation, velocity, or acceleration of the sensor. The system also comprises a master control unit configured to receive information from the sensors and transmit that information wirelessly and a storage medium having reference information for comparison to the sensor information. The system also includes a first processor configured to analyze the sensor information, compare it to reference information, and generate visual images related to the sensor information. The system also includes a display device allowing the user to view the visual images during or shortly after the body movements have been made and a storage medium for retaining the sensor information for later comparison.

In some embodiments of this body movement monitoring system, at least one of the body movement sensors comprises an accelerometer, a magnetometer, or a gyroscopic sensor. In certain embodiments of the system, at least one of the body movement sensors is configured to be substantially water resistant. In certain embodiments of the body movement monitoring system, the first processor comprises a cellular telephone having a graphics display and the display device comprises the graphics display.

An embodiment of a golfer alignment system is disclosed. The system comprises a first sensor associated with the head of a user, a second sensor associated with the upper torso of the user, and a third sensor associated with the lower torso of the user. The system further includes a portable master control unit configured to be worn or carried by the user and a remote processor having a user interface and a wireless receiver. The master control unit is configured to receive data from at least two sensors, and the remote processor is configured to communicate wirelessly with the portable master control unit and provide information related to at least one of the user's stance, alignment, or swing to the user in real time.

In some embodiments, the golfer alignment system further comprises at least one foot sensor. In certain embodiments of the system, the user interface of the remote processor comprises a stance-width indicator that can display information relating to data received from any foot sensors, and the information relates to the distance between the user's feet. In other embodiments, the user interface of the remote processor comprises a at least one foot alignment indicator that can display information relating to data received from any foot sensors, and the information relates to the alignment of the user's feet. In some of these embodiments, the user interface further comprises a visible reference line for use in aligning the user interface with the golf target line. In certain embodiments of the system, the user interface of the remote processor further comprises a human form representation having indicators showing the user any stance changes needed and which portion of the body the stance change should affect.

In an embodiment of the golfer alignment system, the indicators comprise light-emitting diodes. In certain embodiments of the system, the remote processor comprises a cellular telephone. In some embodiments, at least one of the first, second, and third sensors is configured to be associated with a garment worn by the user. In some of these embodiments, at least one of the first, second, and third sensors is configured to be associated with the garment by a hook-and-loop fastener. For some embodiments, at least one of the first, second, and third sensors is configured to be associated with the garment by being disposed in a sensor cavity in the garment. In certain of these embodiments, at least one of the first, second, and third sensors and the sensor cavity are shaped or sized to resist relative movement therebetween.

Also disclosed herein is a method of evaluating a golfer's form. The method comprises associating a plurality of sensors with portions of a golfer's body and associating a master control with the golfer. The master control unit is configured to receive data from the plurality of sensors. The method includes calibrating the plurality of sensors and the master control unit to provide a calibration position. In this method, the golfer assumes a golfing stance with respect to a target line and data from the plurality of sensors is analyzed to evaluate the golfer's form.

In certain embodiments of the method of evaluating a golfer's form, the action of associating a plurality of sensors with portions of a golfer's body comprises associating a first sensor with the head of the golfer, associating a second sensor with the upper torso of the golfer and associating a third sensor with the lower torso of the golfer. In some embodiments of the disclosed method, the action of associating a master control unit with the golfer comprises attaching the master control unit to a portion of the golfer's clothes.

In some embodiments of the method of evaluating a golfer's form, the action of calibrating the plurality of sensors comprises assuming the calibration position (by the golfer) and communicating information related to the calibration position to the master control unit. In some of these embodiments, the calibration position comprises a balanced, erect position of the golfer. In another embodiment, the golfer's action of assuming the calibration position comprises standing such that the golfer's left and right shoulders are each located distances away from the ground that are substantially the same and standing such that the golfer's left and right hips are each located distances away from the ground that are substantially the same.

In various embodiments of the method, the golfer's form comprises the golfer's stance, alignment, or swins. In some of these embodiments, the action of analyzing data from the plurality of sensors comprises at least one of determining a width of the golfer's stance, an alignment of regions of the golfer's body, and a lean in an address position of the golfer. In certain of these embodiments, the regions of the golfer's body include the golfer's head, feet, hips, or shoulders.

Embodiments of the method of evaluating a golfer's form further comprise aligning an interface box with the target line. The interface box is configured to communicate with the master control unit so as to provide visual or audible information to the golfer. In some of these embodiments, the visual or audible information relates to the golfer's stance, alignment, or swing. In certain embodiments, the visual information comprises activating a light-emitting diode. The audible information comprises activating a sound-emitting device in some embodiments. The method of evaluating a golfer's form may further comprise performing a golf swing (by the golfer) and activating a rhythm indicator in response to the golf swing.

Embodiments of a system for evaluating a body movement are disclosed, wherein the system comprises a first sensor associated with a first body portion of a user, a second sensor associated with a second body portion of the user, and a third sensor associated with a third body portion of the user. The system further comprises a portable master control unit configured to be worn or carried by the user. The master control unit is configured to receive data from the first, the second, and the third sensors. The system also includes a remote processor having a user interface and a wireless receiver. The remote processor is configured to (i) wirelessly receive body movement information from the portable master control unit, (ii) calculate a performance evaluation based at least in part on the body movement information, and (iii) provide via the user interface information relating to the performance evaluation. In certain embodiments, the remote processor comprises a cellular telephone. In certain such embodiments, the user interface comprises a display of the cellular telephone.

The present disclosure describes a mouthpiece for receiving a radio-frequency (RF) signal and communicating a message included in the signal to a wearer of the mouthpiece. In certain embodiments, the mouthpiece comprises a retainer configured to fit over teeth in the mouth of the wearer, an antenna configured to receive an RF signal that includes a message, and a processor that is in communication with the antenna and that is configured to determine the message from the received RF signal. The mouthpiece further includes a modulator that is configured to receive from the processor a signal indicative of the message and, in response to the signal, to provide a sensory effect in the wearer's mouth that is perceivable by the wearer. The sensory effect is capable of communicating the message to the wearer. In various embodiments of the mouthpiece, the retainer is configured to fit over the lower teeth of the wearer or is configured to fit over the upper teeth of the wearer.

In some applications, the RF signal comprises an RE carrier and a modulated sub-carrier that includes the message. In certain embodiments of the mouthpiece, the processor comprises a signal discriminator capable of decoding the RE signal. In certain such embodiments, the decoded RE signal comprises a sequence of bits.

Embodiments of the mouthpiece may be configured such that the modulator is a vibrator, and the sensory effect causes a tactile stimulus to a portion of the wearer's mouth. For example, in an embodiment, the tactile stimulus is a vibration. In another embodiment of the mouthpiece, the modulator is a vibrator, and the sensory effect causes an auditory stimulus capable of being perceived in the wearer's ear. For example, the auditory stimulus may comprise a frequency of about 1000 Hz.

In some embodiments, the mouthpiece further comprises a power source. In some of these embodiments, the power source comprises a supercapacitor. In an embodiment, the power source is disposed within the wearer's mouth. In another embodiment, the power source is capable of being charged by a portion of the received RF signal.

Disclosed herein are embodiments of a method of communication between at least two users. In an embodiment, the method comprises associating a sensor with a first portion of a first user's body and detecting a body position or a body movement of the first portion of the first user's body with the sensor. The sensor is configured to provide a message related to the body position or the body movement to a radio frequency (RF) transmission unit. The method further includes communicating, with the RF transmission unit, an RF signal that includes the message, and associating a signaling device with a second portion of a second user's body. The signaling device comprises an RF receiver and a modulator configured to provide a physical stimulus to the second portion of the second user's body. Additionally, the method includes receiving, with the RF receiver, the RF signal transmitted by the RF transmission unit, and in response to the RF signal, activating the modulator to provide a physical stimulus to the second user that is capable of conveying the message to the second user.

In various implementations of the method of communication, the RF signal comprises an RF carrier and a subcarrier that includes the message. In other implementations, the message comprises a brevity-code or a Morse-code. In some embodiments of the method, the message is encrypted, and the signaling device is configured to decrypt the message before activating the modulator.

In certain embodiments of the method of communication, the second portion of the user's body includes the second user's mouth, and the signaling device is sized and shaped to be disposed at least partially in the second user's mouth. In some embodiments of the method, the physical stimulus includes a vibration. For example, the vibration can comprise a frequency capable of being perceived in an inner ear of the second user. In one embodiment, the frequency is about 1000 Hz. In certain embodiments of the method of communication between at least two users, the signaling device comprises an embodiment of the above-described mouthpiece for receiving a radio-frequency (RF) signal.

An embodiment of a method for providing biometric-enabled devices to a consumer comprises forming a consortium comprising members and establishing, by the consortium, a biometric data protocol. The method further comprises providing to the consumer a biometric-enabled device that conforms to the biometric data protocol. The members of the consortium include at least a biometric data provider and a device manufacturer. In certain embodiments of this method, the members of the consortium further comprise a telephone carrier.

In some embodiments of this method, the biometric-enabled device comprises a telephone. For example, the telephone may comprise a wireless telephone. The wireless telephone may be disposable.

In certain embodiments of the method for providing biometric-enabled devices to a consumer, the biometric data protocol comprises a set of standards for communicating biometric data over a communications channel. In certain such embodiments, the biometric data comprises information related to the position, velocity, or acceleration of one or more portions of a body. In some of these embodiments, the information is produced by at least one sensor attached to the body.

Certain embodiments of the disclosure are summarized above. However, despite the foregoing description of certain embodiments, only the appended claims (and not the present summary) are intended to define the inventions. The summarized embodiments, and other embodiments and equivalents, will become readily apparent to those skilled in the art from the following detailed description of preferred embodiments having reference to the attached drawings. However, it is to be understood that the inventions disclosed herein are not limited to any particular embodiments described.

Figure 1:
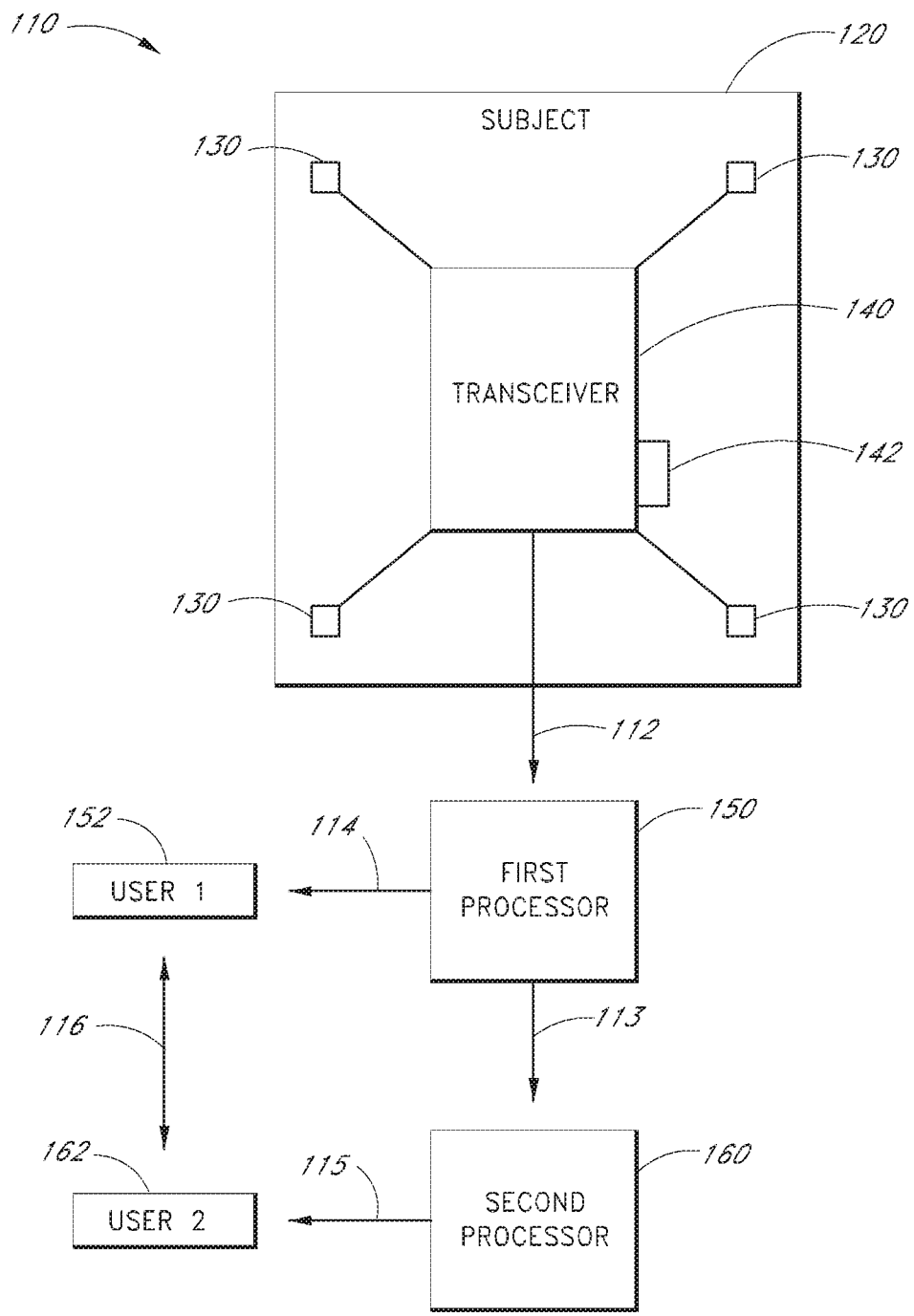
FIG. 1 schematically illustrates a system for gathering and processing biometric and/or biomechanical data that may be used in applications including athletics, medicine, and gaming.

Reference symbols are used in the figures to indicate certain components, aspects or features shown therein, with reference symbols common to more than one figure indicating like components, aspects or features shown therein.

DETAILED DESCRIPTION OF PREFERRED EMBODIMENTS

I. Overview

Systems and methods described herein can be used to gather data relating to positions and movements of various body parts, such as those movements performed in sports activities, for example. The data can be conveyed rapidly so that a user can perceive the data (e.g., in the form of a graphic representation, histogram, and/or listing of numerical parameters) and evaluate the movement. In some advantageous embodiments, the data is conveyed wirelessly to reduce restriction of the movements of the body parts. In some embodiments, a device embodying some aspects of the described technology can be referred to as the "BodySensor" (or BS). A BodySensor can be a remote device that senses body motion and/or symmetry.

Some embodiments disclosed herein can help prevent injury and improve athletic performance by enhancing confidence and providing diagnostic options and services to athletic participants. Some embodiments seek to foster the enjoyment of sports by beginners, amateurs and professional athletes. Embodiments disclosed herein can be used by consumers in various sports, industries, and market segments. Examples of suitable sports include, without limitation, golf, tennis, baseball, softball, football, soccer, track and field, running, jogging, walking, swimming, cycling, skateboarding, aerobics, yoga, weightlifting, bowling, volleyball, gymnastics, skiing, snowboarding. Indeed, the systems and methods described herein can be used in conjunction with any form of body movement, athletics, exercise, and/or recreation whether performed solo or in groups or teams. The described technology and services are extendable across all sports platforms and into other areas such as medical devices, orthopedic medicine, military activities, law enforcement activities, aviation, space travel, and gaining.

In some embodiments, a user can attempt to evaluate body movement data (e.g., an athletic performance) using a remote interface that can use digital performance assessment tools. In some embodiments, the performance assessment and other data analysis can be accomplished whenever, wherever, and however an athlete, coach, or trainer wants it. Thus, in some embodiments, the described technology can provide a competitive edge to athletes, helping athletes perform better and/or reduce the possibility of injury. A preferred embodiment can be used to track measurable aspects of the athlete's physiology and document the performance fingerprint at intervals (e.g., at programmable intervals such as once every millisecond) during the athlete's performance. Thus, embodiments of this technology can measure various flex, bend, twist, torque, and/or symmetry of key body areas that are relevant to various sport, therapy, industry, military, gaming, and/or professional applications, for example.

In some embodiments, systems and methods are described that allow for use of data gathered through such a system. The data from multiple users can be gathered and used for research, medical diagnosis, establishment of norms, averages, baselines, aberrations, standards for athletic recruiting, calibrations, etc. Creation of a database of body movement data can be advantageous for these and various purposes. Thus, some embodiments can capture training and/or performance data that can be used to develop revenue through the lifetime of the customer and/or the product. This development of revenue can be referred to as "lifetime value," or "LTV". Revenue can be created by marketing, selling, and/or licensing the data, Firmware, software, and/or hardware through data collection services (Research), data measurement services (Consulting), performance enhancement services (Training) (e.g., for athletes). The technology can generate a performance "fingerprint" of an athlete's performance (including, e.g., the athlete's recorded movements, mechanics, techniques, physical properties, etc.) which can be related to the athlete's skill, physical characteristics, and/or talent.

A. Example Systems for Gathering and Processing Biometric Data

FIG. 1 illustrates a system 110 for gathering and processing biometric and/or biomechanical data that can be useful in many domains, including but not limited to athletics, medicine, and gaming. A subject 120 can have various sensors 130 positioned on his or her body and/or attached to (e.g., with snaps, hook and loop fasteners, etc.) or positioned within (e.g., inserted into a pocket of, woven into, etc.) his or her clothing. The sensors can be associated with joints and/or appendages of the body in order to track position and or movement of those joints and/or appendages. In some embodiments, the sensors can be located in the mouth of a user in order to sense movement and/or relative position of the teeth or the tongue, for example.

The sensors 130 can connect to and/or communicate with a transceiver 140. In some embodiments, the transceiver can be attached to the body and/or clothing (e.g., the belt) of the subject 120. The transceiver can have a data holder 142. In some embodiments, the data holder 142 is a portable memory device that can be removed such as a flash drive or data card or memory stick or floppy disk, for example.

The sensors 130 can gather data relating to various physical characteristics, positions, changes, performance, or properties of the subject. This data can be referred to as "biometric" data. Biometric data includes biomedical and biomechanical data, and can include any of the following: data tracing the trajectory, speed, acceleration, position, orientation, etc. of a subject's appendage or other body part; data showing the heart rate, blood pressure, temperature, stress level, moisture content, toxin level, viability, respiration rate, etc. of a subject; data showing whether or not a subject is performing a signal or communication movement (e.g., teeth closed, arm cocked, etc.); data showing the posture or other status of a subject (e.g., prone or erect, breathing or not, moving or not); data showing the emotional state of a subject; etc. For example, the sensors can track movement of the subject and/or tension in the subject's muscles. In some embodiments, the sensors 130 can include one or more of the following technologies: accelerometer technology that detects accelerations; gyroscope technology that detects changes in orientation; compass or magnetic technology that senses position and/or alignment with relation to magnetic fields; satellite-based, "GPS"-style technology; radio-frequency technology; etc. More details relating to sensors that can be used with this system are discussed below in the text describing FIG. 2.

The transceiver 140 can collect and store data (e.g., analog and/or digital data) from the sensors 130. In some preferred embodiments, the data is converted from analog to digital in the sensors or the transceiver to facilitate storage and/or transmittance. In some embodiments, the data is sequenced, coded, and or separated to make the reception, storage, and/or transmission more efficient. In some embodiments, the transceiver 140 can be a cell phone, personal digital assistant (PDA), pocket PC, or other portable communications and/or computing device. The cell phone in some embodiments is a disposable cell phone or a prepaid cell phone. In some embodiments, the transceiver 140 can send signals to and/or receive signals from a portable communications device such as those mentioned here, for example.

As illustrated with the arrow 112, the transceiver 140 can transmit data to a first processor 150. The data can be transmitted in electronic or electromagnetic form, for example. In some embodiments, the data is transmitted wirelessly (using radio frequency transmissions, for example). Various communications protocols can be used, including, for example, Bluetooth, TCP/IP, 802.11b, 802.11a, 802.11g, 802.11e, etc.). In certain embodiments, the transceiver 140 transmits the data over the Internet or over a wired or wireless network.

Figure 11:
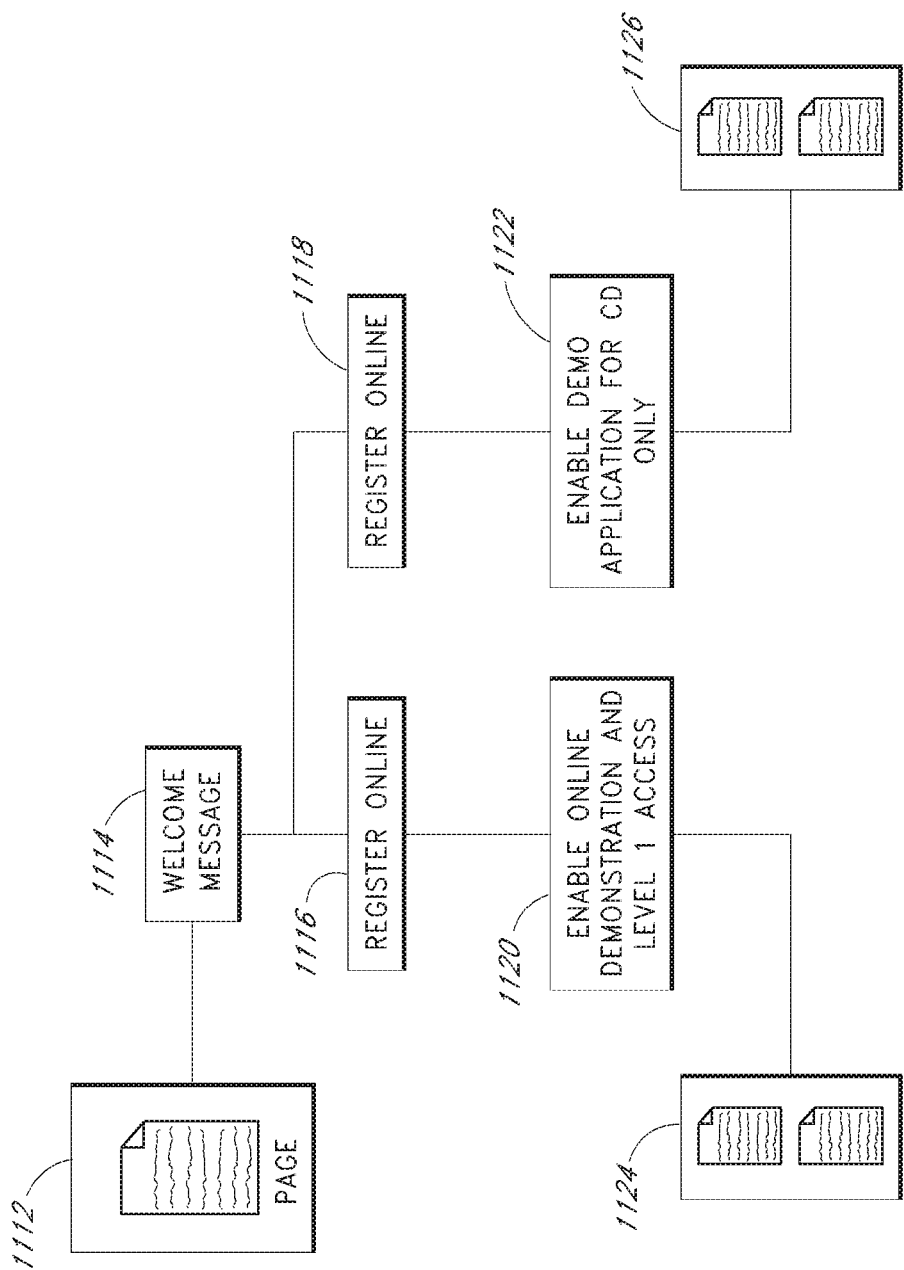
FIG. 11 schematically illustrates an example of offline and online registration options.

The first processor 150 can be one of or a combination of devices or components, such as those illustrated in FIG. 11. The first processor 150 can be a computer and/or remote server such as a laptop computer or computer chip/ASIC, for example. The first processor 150 can be configured to receive signals from the transceiver 140 and can have software that allows a first user 152 to view or otherwise use the data. In some embodiments, the first processor 150 can be a cell phone, personal digital assistant (PDA), pocket PC, or other portable communications and/or computing device. In some embodiments, the functions described for the transceiver 140 and the first processor 150 can be merged into a single device. Thus, a portable communications device can be configured to: collect data from the sensors 130; store data (e.g., on a memory card in the portable communications device); and/or transmit data (and/or a processed form of that data). In some advantageous embodiments, data transmission is accomplished wirelessly to a second processor 160 as described further below.

The first user 152 can be the same entity as the subject 120, for example. Thus, in some embodiments, the subject 120 can gather physiological and/or biometric data using the sensors 130, send that data to the transceiver 140 which in turn transmits the data to the first processor 150, which can be the subject's laptop, for example. The subject can then become the first user 152, accessing the data from the first processor as shown by the arrow 114. The first user 152 can view the data in various formats, some of which may involve some automated processing. For example, the user can view three-dimensional animations (e.g., those created using interpolation), histograms, or other graphical reports. In certain preferred embodiments, the data collected by the sensors permit the user to view an animation of the user's own movements as reconstructed from the biomechanical data collected by the sensors. Additionally, in some embodiments, the user can view animations of another person's movements reconstructed from biomechanical data collected on the other person's movements. For example, in an embodiment, the user can view his or her own performance and then view the performance of a friend, coach, competitor, instructor, trainer, or professional. The first user 152 can be an athlete, patient, coach, doctor, physical therapist, data analyst, etc., and need not be the same entity as the subject 120.

The data (or a modified/processed form thereof) can be sent from the first processor 150 to a second processor 160 (e.g., via a wired or wireless network or the internet, for example). In some embodiments, the second processor 160 can perform the functions described above with respect to the first processor 150. In some embodiments, the second processor 160 can perform additional analysis or processing. Furthermore, as shown by the arrow 115, the second processor 160 can make the data available to a second user 162. The second user 162 can be the subject 120 and/or the first user 152, but the second user 162 can also be a different entity such as a specialist, statistician, analyst, doctor, or coach, for example. In some embodiments, the second user 162 can communicate or interact with the first user 152 as shown using the arrow 116. Thus, a second user 162 such as a coach can have access to the same data being viewed by the first user 152 and/or subject 120 such as an athlete. The second user 162 can then interpret and explain the data to the subject 120, request more data, use automated analysis methods (e.g., using the second processor 160) to extract diagnostic information from the data, speak or send further information to the first user 152, etc. In this way, the second user 162 can provide a "virtual assessment" to the first user of the first user's movements (e.g., golf swing, baseball pitch, running stride, swimming stroke, rehabilitative movement, etc.).

Additional users and additional processors can be used. For example, a third user can comprise an institution that collects data from multiple subjects or multiple users and processes that data to find patterns or establish norms, for example. In some embodiments, the system can comprise sports training monitoring equipment that allows an athlete and/or trainer to monitor an individual training program and to compare an exercise program to a previously stored reference workout or other bench-mark. An athletic trainer can monitor an athlete workout in real time h monitoring sensor data captured and wirelessly transmitted to the trainer display system. As used herein, the term "real time" is used broadly to mean that the data is not available hours later, but is instead available within less than one hour. Preferably, the monitoring and some analysis can be done within a matter of minutes. Advantageously, high-speed data transfer can allow monitoring to occur within a short time (e.g., less than 5 minutes) of the body movement. In some preferred embodiments, monitoring can occur within less than one minute of the body movement. Preferably, all data is stored so that analysis of that data can be compared to other athletes and enhance the training programs.

B. Example BodySensor Systems

Figure 1A:
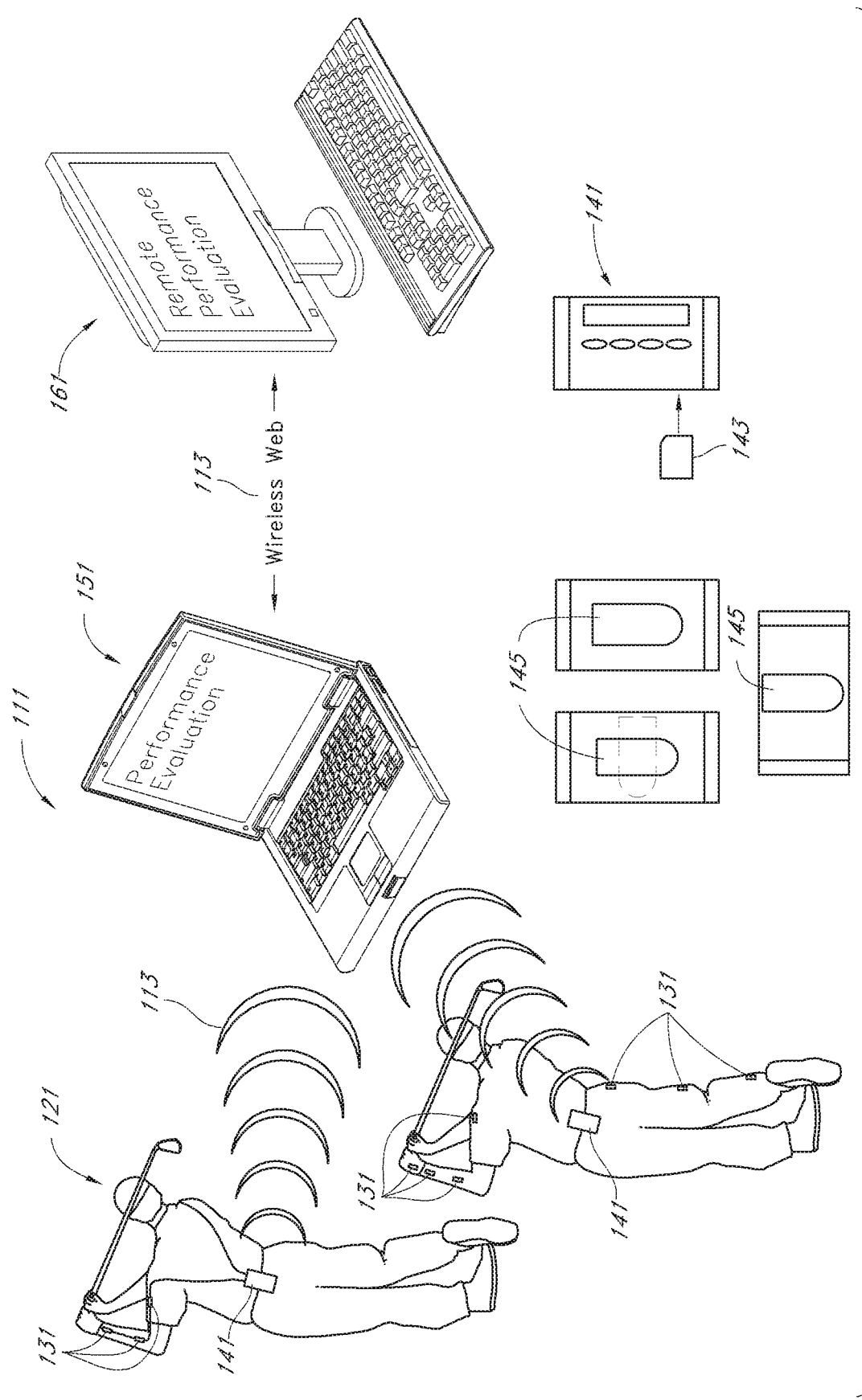
FIG. 1A schematically illustrates an embodiment of a system in accordance with the system of FIG. 1.

FIG. 1A shows an exemplary embodiment of a system 111 in accordance with the description of FIG. 1 above. The illustrated system can be termed a "BodySensor" system. The system 111 can be used by a golfer 121 (an example of a subject 120 of FIG. 1) to assist the golfer 121 in improving his golf game. The golfer 121 can attach various sensors 131 to his body or clothing as shown (see also the garment 200 described with reference to FIGS. 2A-2D). Sensors can also be woven into the fabric of the clothing. In some embodiments, sensor can be incorporated into an undergarment so they are less noticeable and/or cumbersome and conform more closely to the user's body. In some embodiments, sensors can be embedded in the skin of a user. The sensors 131 can gather data relating to the golfer's form, balance, stance, posture, position, speed and shape of swing, etc. The sensors 131 can then send data to a master control unit, or "MCU" 141 (an example of a transceiver 140 of FIG. 1). A detail of an embodiment of the MCU 141 and some sensors 131 is provided in FIG. 2.

The MCU 141 can have a clip 145 on the back for attaching to a belt, for example. The clip 145 can rotate in order to allow the MCU 141 to be oriented in various ways, according to the need or whim of the golfer 121. The MCU 141 can in turn transmit data wirelessly (as shown by wavefronts 113) to a laptop computer 151 (which is an example of a device that can act as the first processor 150 of FIG. 1). In some embodiments, the MCU 141 can transmit data wirelessly via the World Wide Web through a built-in Web server chip contained in the MCU. Alternatively, the MCU 141 can store data on an SD card 143 for later transfer to a processor. In some embodiments, the MCU 141 can be a cell phone, personal digital assistant (PDA), pocket pc, or other portable communications and/or computing device. For example, an additional chip and/or memory card can be inserted into a cell phone to make the cell phone compatible with a system such as that described herein. Other component options and combinations are illustrated in FIG. 11.

When the data is on the laptop computer 151, a user (such as the golfer 121) can use software on the laptop computer 151 to analyze the data and provide, for example, a "performance evaluation" with graphs, numbers, graphical depictions, charts, histograms, etc. The performance evaluation can include statistical analyses that, for example, determine the user's average performance level and the user's deviations from this average. Statistical techniques can be used to compare the user's performance level with other suitable cohorts defined by demographics, geography, performance level, etc. For example, a golfer's performance evaluation may compare the golfer's performance level with other golfers with the same gender, age, geographic location, etc. or with amateur or professional golfers. Statistical analyses may enable a coach to track the performance of a particular player on a team as compared to other team members, selected past teams, competitor teams, professional teams, etc. The data relating to a particular performance by the user (e.g., the golfer) can be referred to as a "performance fingerprint," and can have unique characteristics. The performance fingerprint can be sent from the laptop computer 151 to another computer such as a desktop computer 161 (an example of the second processor 160 of FIG. 1). This data transmission can occur via the World Wide Web, including through a wireless connection, for example. In some embodiments, a cell phone, personal digital assistant (PDA), pocket PC, or other portable communications and/or computing device can supplement or be substituted for the laptop computer 151 described herein. For example, a cell phone, PDA, etc. can upload data to the World Wide Web, and that data (in raw or processed form) can also be accessed from the cell phone, PDA, etc. In some embodiments, a user's data can be sent to a "learning center" via the World Wide Web, and then that same user can thereafter access charts, histograms, etc. that are visible on that user's cell phone, PDA, etc. that provide insight to the user relating to the data and/or the user's performance.

In some embodiments, the data can be viewed and/or analyzed by a third party. The desktop computer 161 can be located at a centralized data processing location where a golf coach, or physical therapist for example, can look at the data and assist the golfer 121 in understanding the performance fingerprint. The desktop and/or second user can provide a "remote performance evaluation" to the golfer 121. The data from the golfer's performance can also be stored in raw and/or processed form for later analysis and comparison.

Figure 1B:
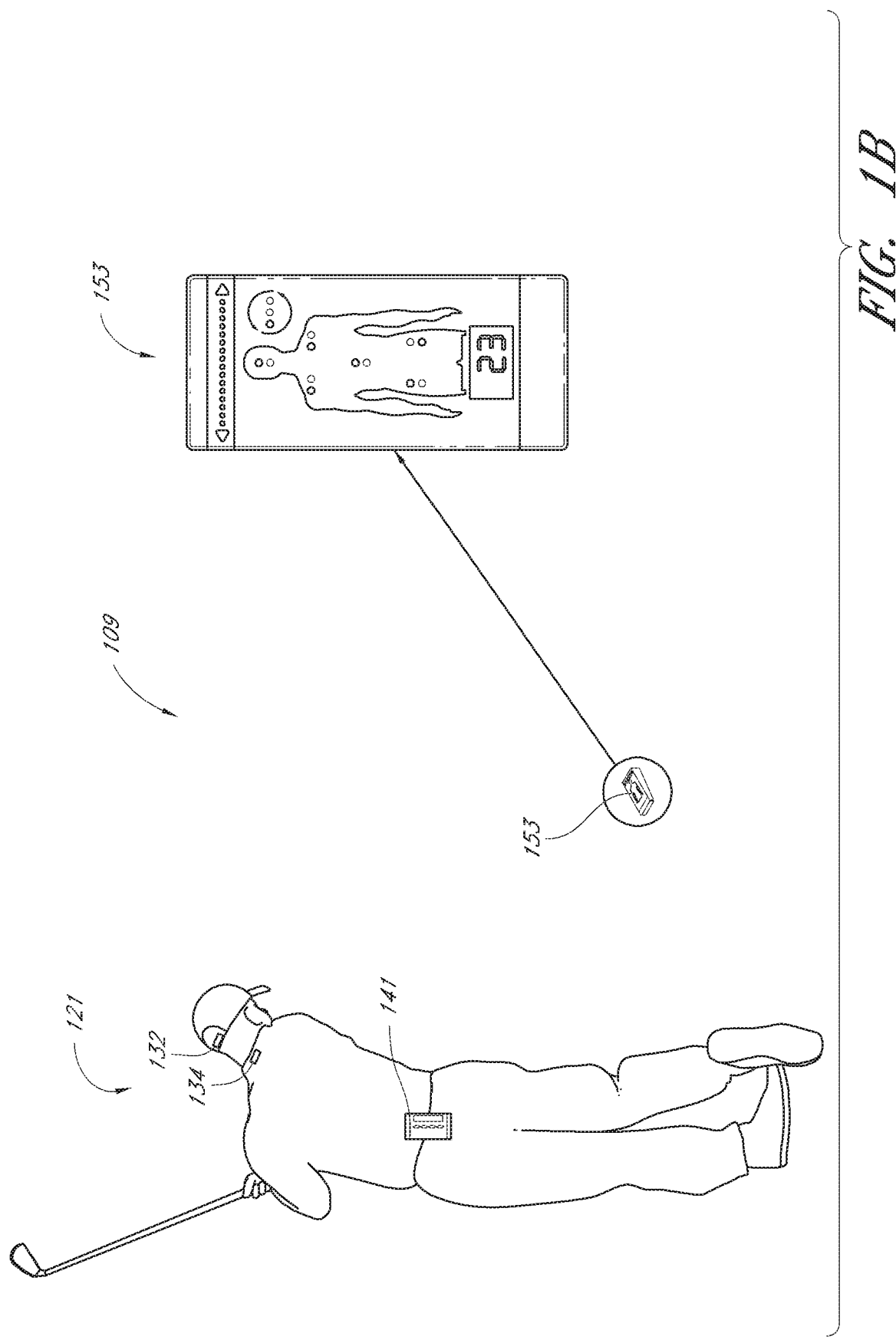
FIG. 1B schematically illustrates another embodiment of a system in accordance with system of FIG. 1.

FIG. 1B shows another embodiment of a system 109 in accordance with the description of FIG. 1 above. In this embodiment, a golfer 121 wears an MCU 141 on his belt, and the MCU 141 transmits data to an interface box 153. The interface box 153 is an example of the first processor 150 of FIG. 1, and the golfer 121 in this example is both the subject 120 and the first user 152 described with reference to FIG. 1. In this example, the golfer 121 can interface directly with the interface box 153. Thus, in some embodiments, the second processor 160 depicted in FIG. 1 may be optional. For example, a simple, inexpensive system can omit the second processor. In some embodiments, the MCU 141 transmits data to the interface box, which can provide visual or audible feedback to the golfer 121. The feedback can relate to desirable adjustments in stance, form, body position, etc.

In the illustrated embodiment, the system 109 employs three body-mounted tilt sensors: a head sensor 132 mounted to the back side of the head of the golfer 121 (e.g., attached or fastened to a hat); a shoulder sensor 134 mounted in the center of the back at shoulder level (e.g., fastened to a shirt under a collar); and a hip sensor mounted on the lower back above the hips (e.g., located in the MCU, which can be attached to a belt above the hips). Each of these sensors can be placed into pockets or compartments of the golfer's clothing, or woven or sewn into the golfer's clothing, for example. Each tilt sensor can comprise an accelerometer and can detect and indicate the tilt or deviation of the body away from vertical. For example, the head sensor 132 can indicate the vertical angle (tilt of the head side-to-side generally in the midsagittal plane) and the horizontal angle (tilt of the head forward or back—generally in the frontal plane) of the head. The shoulder sensor 134 can detect and indicate the shoulder angle (whether the shoulders are tilted side-to-side—generally in the frontal plane—such that a line taken between two analogous portions of the two shoulders is not parallel to the ground) and the vertical angle of the upper spine (tilt of the upper spine forward or back—generally in the midsagittal plane). The hip sensor can indicate the hip angle (whether the hips are tilted side-to-side—generally in the frontal plane—such that a line taken between two analogous portions of the two hips is not parallel to the ground) and the vertical angle of the lower spine (tilt of the lower spine forward or back—generally in the midsagittal plane).

The system 109 can also have one or more sensors having magnetometers for sensing direction relative to the magnetic field of the earth. For example, a sensor can be associated with each shoe of a golfer 121. These sensors can help determine if the golfer's feet are parallel to each other and perpendicular to the golf target line (the line along which the golf ball should be launched). Similar sensors can also be associated with the MCU 141, and with the interface box 153. Thus, shoe or foot sensors can interact with sensors in the interface box 153 to determine the angle of the feet with respect to the angle of the gold target line as determined with respect to the position of the interface box 153.

The system 109 can also have one or more distance sensors associated with the feet of the golfer 121. For example, a first distance sensor on one foot can have a transmitter that transmits an ultrasonic signal that reflects off a flat surface of another sensor on the other foot and travels back along its original path so that it is detected by a receiver in the first distance sensor. The distance sensor can calculate the distance between the two feet based on the time delay between transmitting and receiving the ultrasonic signal. Laser distance sensors can also be used. In some embodiments, a signal source on the feet can transmit to a receiver (instead of a reflector) associated with the interface box 153 so that the distance is calculated without the signal being reflected back toward its origin. The distance sensors can be used to indicate proper placement and alignment of the feet with respect to the interface box 153 and the golf target line.

In some embodiments, various sensors can be combined. For example, a distance measuring sensor can be combined with a magnetometer so that the same sensor can measure both the distance between the center line of the golfer's feet and the orientation of each foot with respect to magnetic north (or the orientation of each foot with respect to the golf target line, for example).

Figure 3:
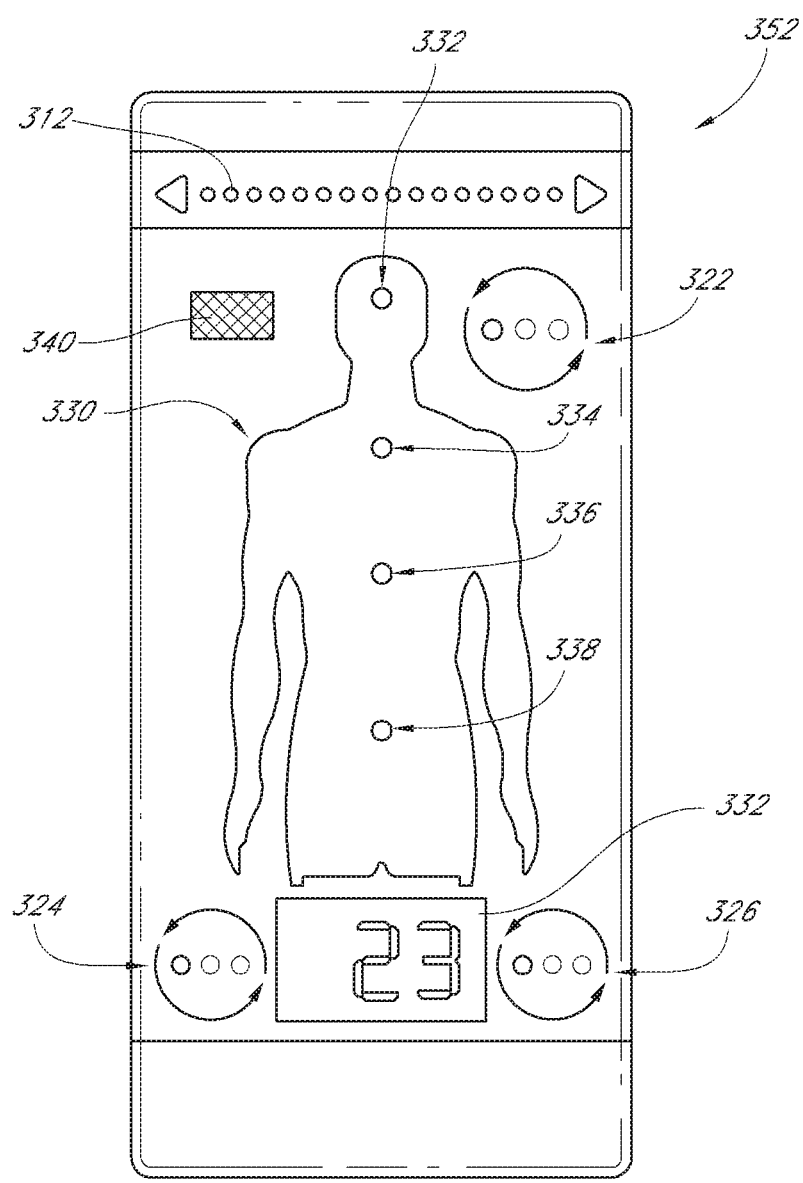
FIG. 3 schematically illustrates a close-up view of one embodiment of an interface box.
Figure 14:
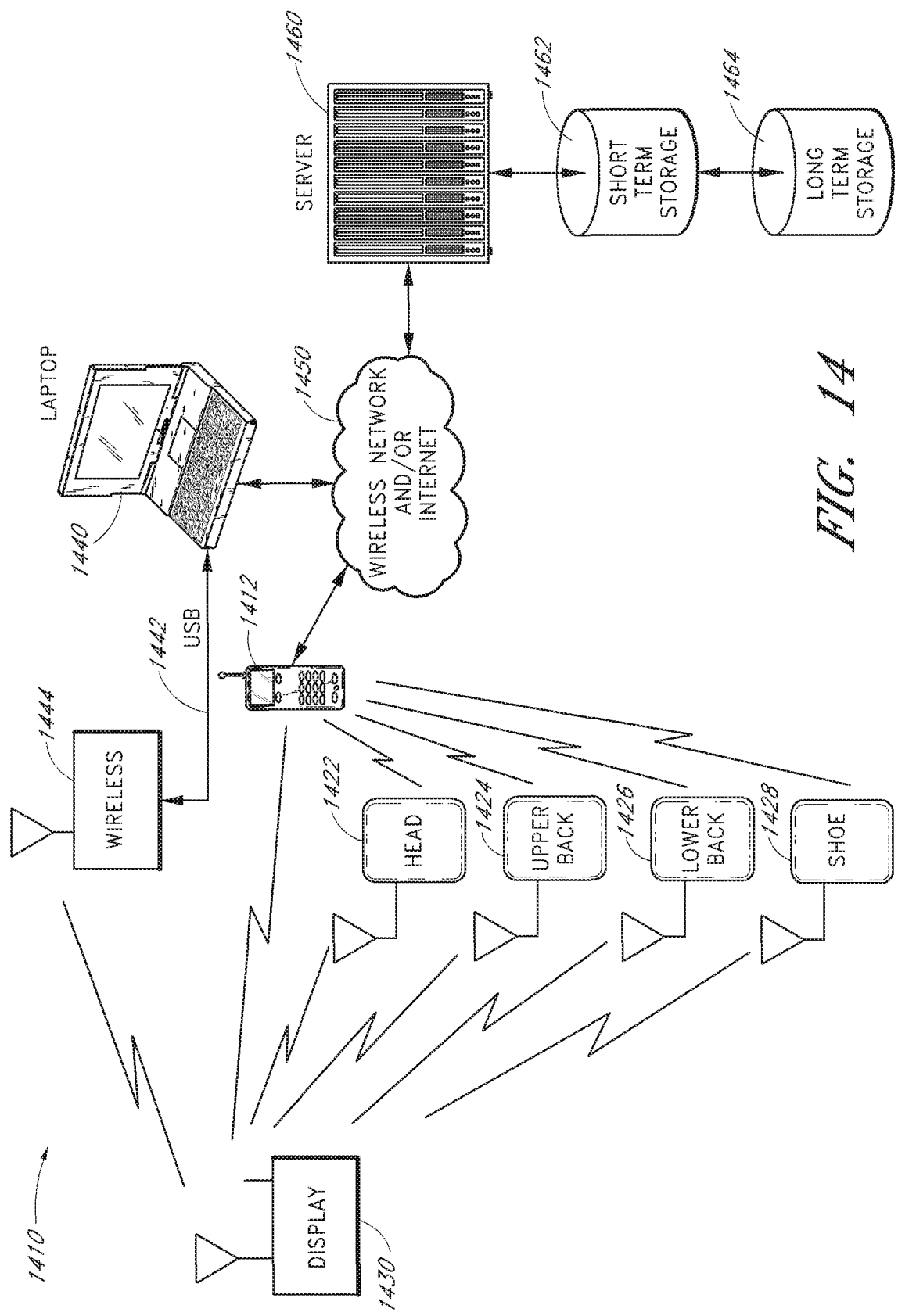
FIG. 14 schematically illustrates wireless communications in a system according to the present disclosure.

At the left, FIG. 1B shows a golfer 121 looking down at the interface box 153 as the golfer 121 completes his swing. The interface box 153 is depicted on the ground in a typical orientation. At the right, a more detailed view of the top of an embodiment of the interface box 153 is shown. FIG. 3 provides more details about the functions and display of the interface box 153. FIG. 14 provides a description of how the system 109 can use wireless communication.

1. Sensors

Figure 2:
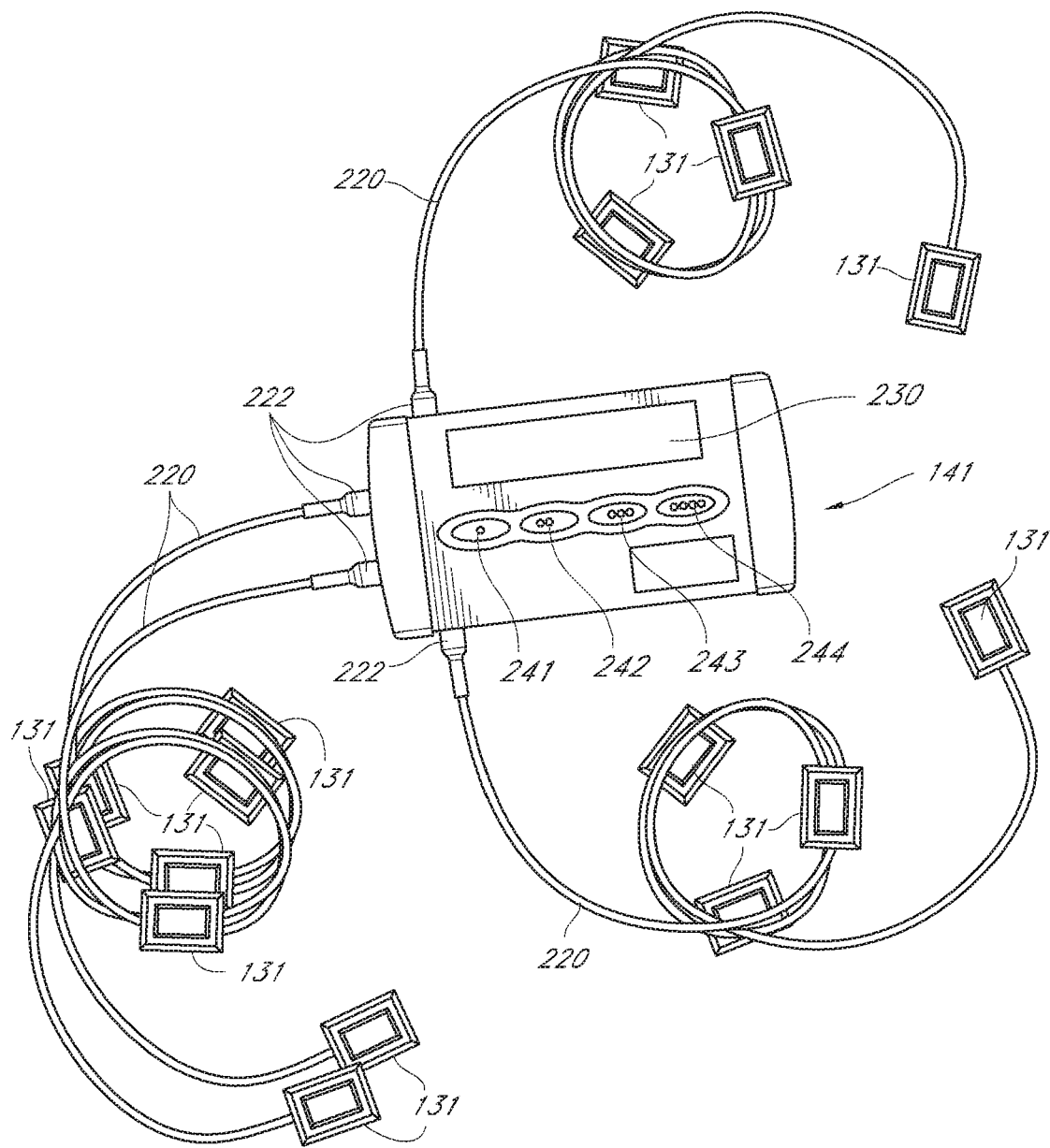
FIG. 2 schematically illustrates a perspective view of one embodiment of sensors and a master control unit (MCU).

FIG. 2 shows a close-up view of one embodiment of the sensors 131. The sensors 131 can be referred to as "Body Sensors." Various kinds of sensors can be used to measure biometric data. For example, some sensors have an accelerometer and can measure and transmit data representing X, Y, and Z coordinates of the position where the device is mounted. Such sensors can be referred to as having three "sense points." Some sensors have, instead of or in addition to an accelerometer, a magnetometer. A magnetometer can, like a magnetic compass, sense orientation relative to the surrounding magnetic fields. For example, magnetometers can use earth's magnetic field to determine orientation with respect to magnetic north. Some sensors have, instead of or in addition to the components described above, have ultrasonic sensors. These sensors can emit and/or receive ultrasonic signals and are generally used to determine the distance between sensors or between a sensor and a reflective surface. Some sensors have, instead of or in addition to the components described above, a gyroscope. Gyroscopic sensor components can establish an orientation and sense deviations from that orientation based on the principle of conservation of angular momentum. Some sensors have only an accelerometer, while other sensors have an accelerometer, a magnetometer, and an ultrasonic sensing component. Some sensors have an accelerometer, a magnetometer, and a gyroscopic sensing component. Preferably, the sensors employed are small and light-weight, with low power requirements. Preferably, the sensor system measures nine (9) degrees of motion using acceleration sensors, magnetometer, and gyros.

In some embodiments, each sensor has a micro controller that makes the physical measurement and converts the data into an appropriate communication protocol. The data collected from each of these sensors is processed and stored in real time in the MCU 141 which can be worn by the subject 120 (see FIG. 1).

In some embodiments, each body sensor 131 comprises a three-axis accelerometer, a three-axis magnetometer, and a three-axis gyroscopic sensor. One or more sensors can be used. In certain embodiments, 2, 3, 4, 6, 8, 10, 12, 18, or more sensors are used. In two golf-related embodiments shown in FIG. 1A, one shows two arm sensors, and the other shows three arm sensors, a shoulder sensor, and three leg sensors. In golf-related embodiments shown in FIG. 1B, only two external sensors 131 are depicted, one on the head, and one at the base of the neck. The data from each of the sensor components are combined to determine the motion of the sensor in three dimensions.

In some preferred embodiments, eighteen sensors are attached to the user's as described in Table 1. Each sensor advantageously includes a subsensor unit to determine the position, orientation, velocity, and acceleration along each of the three dimensions. A subsensor unit may comprise an accelerometer, a magnetometer, and/or a gyroscopic detector to track the movement of the portion of the user's body to which the sensor is attached.

TABLE 1

| Sensor Position on User's Body |
| --- |
| Head |
| Right Shoulder |
| Led Shoulder |
| Right Upper Arm |
| Left Upper Arm |
| Right Forearm |
| Left Forearm |
| Right Hand |
| Left Hand |
| Waist |
| Right Hip |
| Left Hip |
| Right Upper Thigh |
| Left Upper Thigh |
| Right Lower Leg |
| Left Lower Leg |
| Right Ankle |
| Left Ankle |

In one embodiment, each subsensor takes data at data rates up to about 2000 Hz and uses 16 bits per channel. In other embodiments, some or all of the sensors may be programmed to take data at a variable sampling rate. For example, the sampling rate may be programmed based on the particular athletic or rehabilitative activity for which the user desires to obtain biometric performance information. In some implementations, the user may set the sampling rate for some or all of the sensors, or the sampling rate may be set by the MCU 141 prior to a movement by the user. For example, in a golf application using the sensor positions shown in Table 1, the user (or MCU 141) may select a slow sampling rate for body portions that move relatively slowly (e.g., head, ankles, waist, lower legs), an intermediate sampling rate for body portions that move at higher speeds (e.g., shoulders, hips, upper legs), and a fast sampling rate for body portions that move at relatively high speeds and/or which exhibit substantial displacements from their initial positions (e.g., arms and hands).

In one embodiment, the slow sampling rate may be about 10 Hz, the intermediate sampling rate may be about several hundred Hz, and the fast sampling rate may be about a kHz. Other sampling rates may be used for other applications. Embodiments providing variable sampling rates beneficially may use less data storage and lower data transfer rates, because fewer data samples are taken with sensors that measure only relatively slow speeds or small movements. In other embodiments, a uniform sampling rate may be chosen for some or all of the sensors, which beneficially may provide a simpler user initialization process and may reduce possible synchronization problems between sensors.

In some preferred embodiments, each sensor 131 defines its own coordinate system (e.g., "body coordinates"). A network of sensors 131 is established, in which each sensor 131 is mechanically (and/or electrically and/or wirelessly) linked, for example, via the user's limb and torso connections, to a neighboring sensor. In this embodiment, the sensors 131 are related in a hierarchical tree network, with the root of the tree being, for example, a master sensor (e.g., the MCU 141). One or more paths can be defined through the hierarchical tree network. As an example, one path in the tree could be: forearm sensor—upper arm sensor—back of torso sensor (e.g., the master sensor). The body coordinates from a sensor are transformed into an adjacent sensor's body coordinate system, and so on among the sensors on the path, resulting finally in body coordinates in the master sensor body coordinate system. The body coordinates of the master sensor are then transformed into an "Earth" coordinate system, e.g., a coordinate system established for the environment in which the user performs actions. Accordingly, in preferred embodiments, Earth coordinates for each sensor may be calculated, which permits tracking of all the sensors in a common coordinate system (e.g., the Earth coordinate system). In certain embodiments, a Kalman filter (or other suitable signal processing filter, method, or technique) is used to control error propagation in the data from each sensor. In some embodiments, sensor position, orientation, and rotation are represented using mathematical methods and algorithms utilizing quaternions. Such embodiments may have improved computational efficiency and/or computational speed.

In certain embodiments, the orientation of the sensor 131 is determined by measuring a local magnetic field vector and a local gravity vector and using those measurements to determine the orientation of the sensor. Some embodiments can include measuring the magnetic field vector and the local gravity vector using quaternion coordinates. Other methods for determining sensor orientation comprise measuring a local magnetic field vector, a local gravity vector, and the angular velocity of the sensor. These three vectors are processed to determine the orientation of the sensor. In certain embodiments, the three vectors are measured in quaternion coordinates.

Another method for determining sensor orientation comprises determining a local gravity vector by providing an acceleration detector, moving the detector from a start point to an end point over a time period, and summing acceleration measurements over the time period. The local gravity vector is calculated using the summed acceleration measurements. In another embodiment, the orientation of a sensor 131 can be tracked by measuring an angular velocity of the sensor 131 so as to generate angular rate values that are integrated and normalized to produce an estimated sensor orientation. Additionally, a local magnetic field vector and a local gravity vector can be measured by magnetic and acceleration sensors, respectively, and these measurements can be used to correct the estimated sensor orientation.

Many other methods and techniques can be used to determine and track sensor orientation. For example, certain preferred embodiments use methods substantially similar to the methods disclosed in U.S. Pat. No. 6,820,025, titled "Method and Apparatus for Motion Tracking of an Articulated Rigid Body," issued Nov. 16, 2004, which is hereby incorporated by reference herein in its entirety and made part of the specification hereof. In some implementations, kinematic equations of motion for determining sensor position and/or orientation are solved using methods disclosed in U.S. Pat. No. 6,061,611, titled "Closed-Form Integrator for the Quaternion (Euler Angle) Kinematics Equations," issued May 9, 2000, which is hereby incorporated by reference herein in its entirety and made part of the specification hereof.

In some embodiments, other mathematical methods and algorithms are used, e.g., Euler angles, roll/pitch/yaw angles, matrix techniques, etc. For example, some embodiments utilize techniques to track the orientation and movement of the sensors including those described in, for example, U.S. Pat. No. 6,305,221, titled "Rotational Sensor System," issued Oct. 23, 2001, and/or U.S. Pat. No. 6,636,826, titled "Orientation Angle Detector," issued Oct. 21, 2003, each of which is hereby incorporated by reference herein in its entirety and each of which is made part of the specification hereof.

FIG. 2 also shows a close-up view of one embodiment of a transceiver 140, in the form of an MCU 141. The MCU 141 can process data from the sensors 131, managing the data in real time. Real time can refer to very fast processing speed. In some embodiments, real time can refer to data transmission and processing that allows a display to show movement so quickly after the corresponding real movement was made that the display appears to a human observer to be synchronized with, or approximately synchronized with the actual movement. In some embodiments, the movement does not appear to be precisely synchronized but it can be positively related to the real movement by a human observer.

The MCU 141 can be a computer-based device and can operate on battery power (e.g., it can use a standard 9-volt battery, a rechargeable battery, or some other source of power). A housing 210 can enclose not only a battery (not shown), but also various other electronic circuitry in the MCU 141. Cables 220 can connect with the housing 210 through connectors 222, extending from the housing 210 to the sensors 131. In some embodiments, the cables 220 are not necessary because the sensors 131 transmit wirelessly to the MCU 141. The MCU 141 can have a screen 230 that provides a visual display or interface for a user. The MCU 141 can also have features that allow a user to control or otherwise interact with the MCU 141. For example, a first button 241 can change the "mode" of the MCU 141, a second button 242 can select a command from a menu (which can be visible on the screen 230, for example), a third button 243 can scroll up on a menu or move a cursor up, and a fourth button 244 can scroll down on a menu or move a cursor down.

Although FIG. 2 illustrates an embodiment wherein the sensors 131 are connected to the MCU 141 via wired connections (e.g., the cables 220), in other embodiments the sensors 131 communicate with the MCU 141 (or other transceivers, processors, and/or networks) via wireless techniques, as further described herein.

2. Sensor Attachment to the User's Body

The sensors 131 may be attached to suitable portions of the user's body via straps, bands, wire or string, harnesses, Velcro connectors, or by any other suitable attachment method or device. It is advantageous if the position and orientation of the sensors 131 relative to the user's body does not substantially change during the user's movements. In some preferred embodiments, some or all of the sensors 131 are attached to a garment that is worn by the user while biometric data is being taken.

Figure 2A:
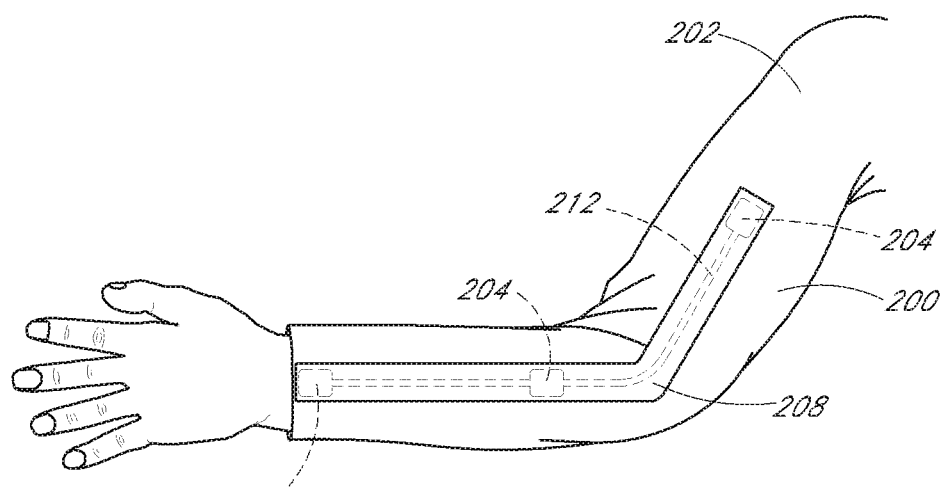
FIG. 2A schematically illustrates how sensors can attach to a portion of a garment, such as a sleeve.

FIG. 2A illustrates one manner of attaching sensors to a garment (e.g., a sleeve). If the sensors are securely fastened, they can remain in place during body movement. If the sensors are associated with clothing that is fitted tightly against the body of the wearer, accuracy of sensor data can be improved. However, it is desirable for any such garment fitted with the sensors not to impede the movement of the wearer. FIG. 2A schematically illustrates a user's arm within a garment 200 comprising a sleeve 202. Three sensors 204 (which may be similar to the sensors 131) are shown as attached to the sleeve 202, but fewer or more sensors can be used in other embodiments. A "Velcro" (e.g., hook and/or loop material) base 208 can be attached (e.g., stitched, adhered, snapped, bonded, etc.) to a portion of the garment 200 such as a portion of the sleeve 202.

Figure 2B:
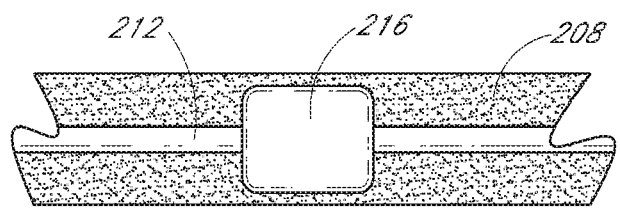
FIGS. 2B and 2C are closeup views of two embodiments of a wire channel and a sensor cavity in the garment of FIG. 2A.
Figure 2C:
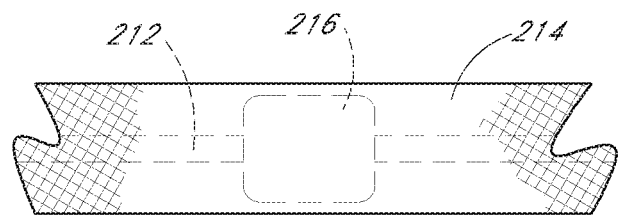

In some embodiments, the garment 200 conforms to the user's body so that the garment does not shift or move with respect to the user's body or a portion of the user's body (e.g., the user's arm) when the user engages in athletic activities. As shown in FIG. 2B, the Velcro base 208 can include a wire channel 212 and a sensor cavity 216 for holding one of the sensors 204. It is preferred, but not required, that the sensor cavity 216 have a size and shape suitable to hold a sensor 204 without substantial relative movement or rotation of the sensor 204 with respect to the user's body or a portion of the user's body. In some embodiments, the sensor 204 has a shape, such as a rectangular shape, and the sensor cavity 216 has a corresponding shape, such as a rectangular shape, configured to snugly hold the sensor 204 so as to limit relative movement and/or rotation of the sensor 204. In other embodiments, the sensors 204 are sewn, stitched, glued, bonded, attached with Velcro, or otherwise held in place within the cavity 216. In some embodiments, the wire channel 212 has a width of about ⅛ inch, the sensor cavity 216 has dimensions of about 1 inch by 1½ inches, and the Velcro base 208 has a transverse width of about 1 inch. In certain embodiments, a strip 214 can cover the wire channel 212 and the sensor cavity 216 as shown in FIG. 2C. The strip 214 can be made from cloth, Velcro, or other suitable material. The strip 214 can be configured to resemble a racing stripe. In some embodiments, the strip 214 is reflective.

Figure 2D:
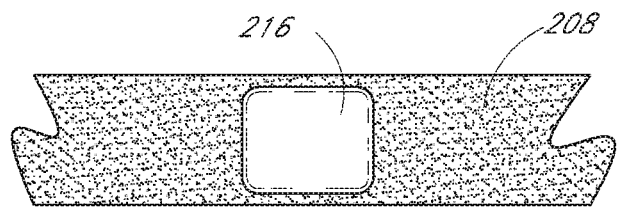
FIG. 2D is a closeup view of a sensor cavity that can attach a wireless sensor to a garment.

Various attachment methods can be used, including snaps, buttons, zippers, etc. As shown in FIG. 2D, some embodiments of the garment 200 do not include the wire channel 212, and may be advantageously used with wireless sensors. In some embodiments, some or all of the sensors are in physical contact with the wearer. Thus, they can be attached to the inside of a garment sleeve, for example.

3. Water-Resistant Systems

Some embodiments of the present inventions are configured for use when the user is swimming or is likely to become wet (e.g., triathlons, water polo, beach volleyball, etc.). In some embodiments, some or all of the sensors 131 are configured to be substantially water resistant. This can be accomplished, for example, by encasing or enclosing the sensors in a waterproof or watertight material or container. In some embodiments, the sensor cavity 216 in the garment 200 is configured to be waterproof or watertight. In an embodiment, the strip 214 is configured to provide further water resistance. In some embodiments, a swimmer wears a swimming garment or swim suit made from a material that conforms to the shape of at least a portion of the swimmer's body (e.g., a material such as Spandex or Lycra), and the sensors 204 are snugly attached in the cavities 216. In embodiments suitable for swimming, it is advantageous, although not always necessary, that sensors 131 be wireless sensors to avoid electrical shorting problems with wired connections. Embodiments of the present inventions are particularly advantageous in swimming contexts, because the present system can provide biometric data that conventional optical sensor systems cannot provide due to distortion of the swimmer's image by the water.

As described, some or all of the sensors 131 may be configured to be water resistant (e.g., waterproof, water tight, and/or water-repelling) devices, for example, by enclosing the sensors 131 in a material or casing or container that is resistant to penetration by water, moisture, and/or humidity. In other embodiments, some or all of the components (e.g., the housing 210, the MCU 141, the cables 220, and/or the connectors) are water resistant. The sensors 131 may have connectors that allow them to be daisy chained to other sensors 131. In an embodiment, the connectors are coated or covered with a silicon compound to make the connection to the sensor 131 sufficiently water resistant for the application in which the sensors 131 are to be used. In some applications the sensors 131 may be highly waterproof (e.g., scuba diving, swimming, triathlons, military marine operations, underwater construction), while in other applications the sensors 131 may be only water or sweat resistant (e.g., running, steeplechase). In some embodiments, the sensor 131 is further inserted into a protective plastic enclosure.

The MCU 141 may utilize a water protective covering similar to the sensors 131. If the MCU 141 includes a replaceable power source (e.g., a battery), the sensor 131 may include a water-protected opening having rubber gaskets that compress to seal the opening. If the MCU 141 power source includes a rechargeable power source (e.g., a rechargeable battery), then in some embodiments the MCU 141 may be charged as follows. The enclosure of the MCU 141 may comprise a portion of an electrical coil (e.g., ½ of a transformer), while the exterior of the enclosure comprises another portion of the coil, thereby forming a complete transformer. The electrical field created by the transformer is converted to direct current (DC) by rectification and filtering. The DC voltage is then used to charge the MCU power source. In some embodiments, the MCU 141 comprises a water sensor, so that if the MCU 141 is in the water, the wireless transmitter may be disabled. When the MCU 141 is not in the water, the MCU 141 can be commanded to transmit internally stored data to an external storage device. In water environments where only a low rate of data from the MCU 141 is needed, one or more ultrasonic sensors can be used for transmitting and receiving data underwater. Ultrasonic data may be transmitted on a single frequency or on multiple frequencies via frequency hopping. One embodiment uses a reference time pulse by which to key transmission, so that distance can also be measured in the water.

In some implementations, some or all of the water-resistant sensors 131 include data storage within the sensor housing (or within a water-resistant fitting). The data storage stores data taken by the sensor 131, for later retrieval and analysis. Such implementations are advantageous in applications, e.g., swimming or diving, where water would inhibit the transfer of data from the sensor 131 to the MCU 141.

4. Alternative MCU Systems

MCU systems can be configured in a variety of ways, with varying features, which can be manufactured and sold for different amounts. One example configuration can be referred to as the "Introductory" MCU system. This MCU embodiment can support various sensor configurations used to monitor real time motion. The introductory MCU system can have a slot or connector for plugging in a Flash Memory card for storing collected data and moving the data to a personal computer. The Introductory MCU system can also support an optional low cost wireless interface to transfer the stored data to a personal computer with a wireless interface (which can be offered as an optional accessory, for example). A "Mid-Level" system embodiment can contain all of the functionality of the introductory embodiment and also include both a Flash Memory card and a low cost wireless interface. A "Professional" MCU system embodiment may support the Flash Memory card and a high-end industry standard wireless interface (e.g., 802.11A, 802.11B, 802.11G, etc.). The Professional MCU system can also have an additional, real-time memory to store events lasting two to three times the normal time period. The Professional MCU system can also have an additional server chip that can allow the MCU to transmit data directly to the World Wide Web without the use of an intermediate personal or laptop computer.

In some embodiments, the system (including, for example, the sensors 131 and the MCU 141) can be configured to take data within a range of sample rates. For example, the range may include sample rates from about 1 Hz to about 10 kHz. It is preferable that the sample rate be at least as large as the appropriate Nyquist sample rate corresponding to the motion of the body part to which the sensor is attached. In one embodiment, the sensors 131 use a sample rate of 2 kHz. In some preferred embodiments, the sensor 131 may be configured to use two or more sample rates so as to provide a sample rate that is adjustable or programmable. For example, referring to Table 1, an ankle sensor may be configured to sample at about 10 Hz, a shoulder sensor at 1 kHz, and a hand sensor at, 2 kHz. Advantageously, the sample rate can be adjustable by a manufacturer, retailer, and/or user. In certain embodiments, the sample rate can be adjusted by a transceiver and/or processor (e.g., the MCU 141). For example, in one embodiment the sensor 131 is configured to receive a signal and to adjust the sample rate in response to the signal. The signal can come from a transceiver, or processor. In an embodiment, the sensors 131 are configured to receive such a signal via wireless communication protocols (e.g., Bluetooth, 802.11, RF, etc.).

In other embodiments, the sensor 131 is configured to be coupled to a docking station that can provide the signal through one or more electrical connectors. In some embodiments, a user can change a configuration setting that affects sampling rate to tune or adjust the system for a particular use. Thus, a system such as those described herein can be useful in various markets, with various sports, to track various movements, etc. Another feature that can allow great expandability is to provide open architecture modular code. A programmable sampling rate can have many advantages. For example, it can provide the ability to increase or decrease the rate each sensor is sampled, independently of the other sensors. This can reduce the duplication of data and storage requirements. Another advantage of programmable and/or independent sample rates for various sensors is that different parts of the body can move at different rates. Thus, having the ability to sample the actual rate of movement can reduce data storage needed and/or allocate data storage resources efficiently, providing more resources to be used for data relating to sensors that need to take more data (e.g., those sensors attached to areas where movement is faster). An example is a baseball pitcher. The highest sample rate may only be needed on his pitching arm to capture the high speed motion, while the sensors associated with rest of his body can operate at a small fraction of the sampling rate to capture the rest of (or at least enough of the relevant) body motion data. In some embodiments, an electromyogram (EMG) sensor can be included in such a system to provide additional data. Such sensors can also take advantage of a system with programmable data sample rates, because they may have different data sampling requirements from those of the other sensors.

The sensors 131 (and/or the MCU 141 or other suitable processors) may be configured to use remote signal strength indication ("RSSI") to estimate, for example, the relative distances between the sensors 131 and/or between the sensors 131 and the MCU 141. For example, using RSSI, sensors 131 that are farther apart will communicate smaller RSSI indexes, whereas sensors 131 that are closer together will communicate larger RSSI indexes. In other embodiments, distance between sensors 131 is determined by measuring a time of arrival of a reference signal and a return response to indicate an elapsed time. Distance is calculated from the elapsed time by multiplying by the signal speed (e.g., the speed of light for electromagnetic reference signals or the speed of sound for ultrasonic reference signals).

In certain embodiments the sensors 131 are configured to communicate bidirectionally, e.g., to send and to receive information and/or data. In one such embodiment, the sensors 131 are configured to receive instructions that update firmware disposed within the sensor 131. In another embodiment, the sensors 131 are configured to receive instructions that permit adjustment or resetting of a programmable sample rate. In certain embodiments, instructions can be communicated to the sensors 131 (and/or the MICU 141) that, for example, unlock certain features of the sensor 131. For example, a sensor 131 may include acceleration, magnetic, and gyroscopic detectors. Such a sensor may have the acceleration detectors activated by default, but the magnetic and gyroscopic detectors disabled by default. Rather than having to purchase a new sensor, a user desiring enhanced capabilities provided by the magnetic and gyroscopic detectors can simply pay a fee and a command to unlock the magnetic and/or gyroscopic detectors will be transmitted to the sensor 131 (e.g., via a wireless network, the internet, the MCU 141, etc.).

C. Example Golf Interface Box

FIG. 3 shows a close-up view of one embodiment of an interface box 352 (which can play the role of the interface box 153 of FIG. 1B). The interface box 153 is an example of the first processor 150 of FIG. 1. The interface box 153 can be referred to as a "remote display system" because in use, it can be located on the ground, away from, but visible to the golfer 121, as illustrated in FIG. 1B. Although the depicted embodiment is described below, it should be understood that any of the visible features/aspects of the device can also appear on a screen such as an LCD screen. Thus, a body alignment indicator 322 and/or a stance-width indicator 332, etc. can appear as a portion of a screen display rather than having a separate, dedicated indicator for each function.

The interface box 352 has a line 312 with arrows at either end that can be generally aligned with the golf target line, or the line between the place where the golf ball rests and the hole into toward which the golfer 121 intends to propel the golf ball.

The interface box 352 can include a body alignment indicator 322 with one or more audible or visual indicators. The interface box 352 shown in FIG. 3 includes three visual indicators, although fewer or more visual (and/or audible) indicators may be used. The visual indicators may comprise Light Emitting Diodes (LEDs), bulbs (e.g., incandescent, fluorescent, halogen), fiber optic light indicators, or other suitable light-indicating devices. The audible indicators may comprise a bell, beep, buzzer, chime, alarm, or other suitable sound-producing device. The interface box 352 can communicate with the MCU 141, and the alignment of the magnetometer in the MCU 141 can be compared to the alignment of the magnetometer in the interface box 352. Generally, the golfer 121 should be aligned parallel to the golf target line. In the interface box 352 shown in FIG. 3, if the MCU 141 indicates that the golfer 121 is facing too far to the left, an LED at the left of the body alignment indicator 322 lights up; if the MCU 141 indicates that the golfer 121 is facing too far to the right, an LED at the right of the body alignment indicator 322 lights up. If the golfer 121 is aligned correctly, a middle LED lights up. In other embodiments, an audible indicator additionally (or alternatively) provides a distinctive sound when the golfer is aligned (or misaligned). Such embodiments advantageously provide feedback to the golfer without requiring the golfer to look up (or move his or her eyes) to detect a visual indicator.

The interface box 352 can also include a left foot alignment indicator 324 and a right foot alignment indicator 326, each with three LEDs that operate similarly to those of the body alignment indicator 322. These alignment indicators display the result of a comparison between the alignment of the magnetometers in the sensors on the feet of the golfer 121 and the magnetometer in the interface box 352. In some embodiments, this comparison is made in the MCU 141, and the result of the comparison is sent to the interface box 352. Generally, the feet should be aligned perpendicularly to the golf target line. Thus, if the MCU 141 indicates that either of the feet of the golfer 121 is facing too far to the left, the LED at the left of the corresponding foot alignment indicator lights up; if the MCU 141 indicates that either of the feet of the golfer 121 is facing too far to the right, the LED at the right of the corresponding foot alignment indicator lights up. If the feet of the golfer 121 are aligned correctly, the middle LED lights up in each of the foot alignment indicators 324 and 326.

The interface box 352 can also include a stance width indicator 332. This indicator receives a signal from the MCU 141 that corresponds to the width calculated from the distance sensor or sensors associated with the feet or shoes of the golfer 121. The stance width indicator can indicate the distance between sensors on the golfer's two feet. In some embodiments, the stance width indicator 332 can display three digits of both alphanumerical and or just numerical data. In some embodiments, the stance width indicator can display a number showing the distance (in units of inches or centimeters, for example) between the centerline of one of the golfer's feet and the centerline of the golfer's other foot.

In the center of the interface box 352 is a human profile 330 or other relevant profile. The human profile can have various indicators providing information to a golfer 121 about the golfer's stance or body position. For example, a head LED 332 on the head of the human profile 330 can provide information relating to signals received from the head sensor 132 on the back of the golfer's head. Similarly, the shoulder LED 334 can provide information relating to signals received from the shoulder sensor 134 on the back of the golfer 121 in between the shoulders, and the hip LED 338 can provide information relating to signals received from a hip sensor located in the MCU 141 that can be attached to the golfer's belt, for example. A mid-back LED 336 can provide information relating to signals received from both a head sensor 132 and a shoulder sensor 134.

Various LED, LCD, or other visual interface configurations are possible. For example, in some embodiments, the color of the LED (e.g., green, amber, red, etc.) can indicate whether or not the correct alignment has been reached. In other embodiments, different LEDs can light up when alignment is correct. In some advantageous embodiments, each LED has two colors, amber and green. When the golfer's head is far from being correctly aligned and/or tilted, the head LED 332 flashes rapidly in amber. As the golfer's head approaches the correct alignment and/or tilt, the intervals between flashes decrease but the flashing head LED 332 continues to be amber colored. When the golfer's head is in correct alignment (or within a certain pre-set range that is considered to be or programmed to be "correct") the head LED 332 changes to emit steady green light. The shoulder LED 334 and the hip LED 338 operate similarly, flashing amber with decreasing flash intervals and finally shining steady green light when the correct alignment is approached and then achieved. The mid-back LED has a similar pattern, but it requires the proper alignment and/or tilt from both the head sensor 132 and the shoulder sensor 334 before it will turn green. In this way, it can indicate to the golfer when the proper back and head angles are achieved when addressing the ball.

In addition to using LEDs and other graphical displays, the interface box 153 can also provide information to a user by way of audio signals. In some embodiments, the interface box 153 (and/or the MCU 141 itself) can announce or otherwise audibly communicate information (including the displayed information described above with respect to the interface box 352) to a user. This audio interface can be achieved, for example, through audio signals emitted from a speaker 340 that can be located in the interface box 153. For example, an audio signal can be generated to indicate body rhythm. When a golfer swings a golf club, for example, different sounds can be emitted that indicate whether or not the swing is smooth. Smoothness can be measured by sensors comparing the relative orientations, positions, velocities, or accelerations of various readings or other data taken during a sports movement (e.g., a golf swing).

In some embodiments, the sounds audible to the user (e.g., a golfer or other sports participant) can be descriptive: one sound (e.g., a clicking sound, a buzz, a beep of one tonality) can indicate that the swinging motion is too jerky or random; another sound (e.g., a swoosh sound, a pleasant chord, or a beep of a different tonality) can indicate that the swinging motion is smooth. In some embodiments, sounds can be prescriptive: a series of sounds can be emitted that correspond to the proper rhythm of the golf swing, and the golfer can match the swing to the cadence of the sounds. Visual indicators can be prescriptive or descriptive as well. In some embodiments, the pitch, intensity, and/or repeat rate of the sound can change to provide information about how much the user's movement and/or position varies from a certain value or range of values or to provide other information to the user.

II. Methods for Gathering and Analyzing Biometric Data

A. Communication Methods

Components of the system 110 can be configured to communicate using wired and/or wireless techniques. For example, the MCU 141 can communicate with the interface box 153 using any number of communication protocols, including, but not limited to, 2.4 GHz devices, Bluetooth devices, wireless local area network (WLAN) channels, etc. In some embodiments, the communication occurs using an nRF24XX, available from Nordic Semiconductor ASA of Tiller, Norway. The nRF24XX can use a low-level Frequency Agility Protocol (nAN24-07) that protects against disturbing traffic from frequency stationary systems like WLAN and frequency hopping devices like Bluetooth.

In some embodiments, the data capture and/or transmittal are performed using methods and apparatus substantially as disclosed in U.S. Pat. No. 6,820,025, titled "Method and Apparatus for Motion Tracking of an Articulated. Rigid Body," issued Nov. 16, 2004, U.S. Pat. No. 6,305,221, titled "Rotational Sensor System," issued Oct. 23, 2001, and/or U.S. Pat. No. 6,636,826, titled "Orientation Angle Detector," issued Oct. 21, 2003. The entirety of each of these documents is incorporated by reference herein and made part of this specification.

Figure 4A:
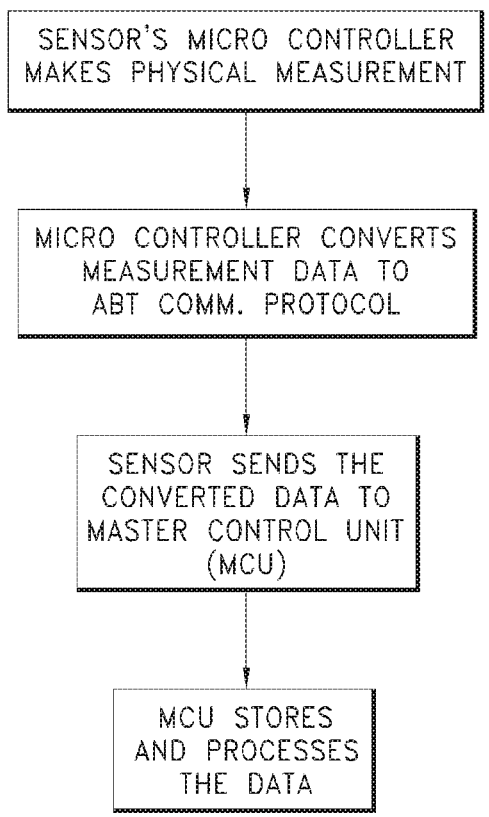
FIG. 4A is a flowchart that illustrates measurement of physical data by an embodiment of the system.

As illustrated in FIG. 4A, a sensor's micro controller can make a physical measurement. The micro controller can then convert the data from the measurement into an agent based transaction model (ABT) communication protocol, which may be advantageous for distributed network services environment. The sensor can then send the converted data to an MCU. The MCU can then store and/or process the data. Thus, in some embodiments, the sensor data is sampled and transmitted to the MCU 141 for processing and/or storage. In some embodiments, the sensors 131 can include micro controllers that output digital data. The micro controllers can convert the measured data into a special communication protocol (e.g., an AST communication protocol) that is compatible with the MCU 141.

Figure 4B:
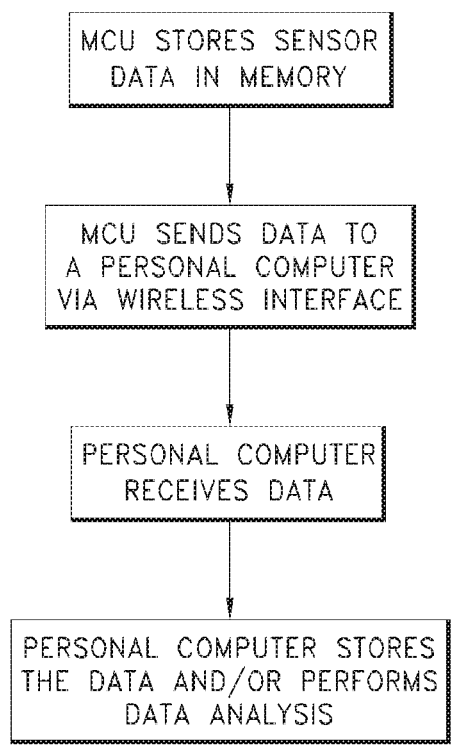
FIG. 4B is a flowchart that illustrates transfer of data from the MCU to a personal computer for storage and/or data analysis.

As illustrated in FIG. 4B, in some embodiments, the MCU 141 can store the sensor data. The MCU 141 can also further process the sensor data. As shown, the MCU 141 can send data to a first processor (e.g., the first processor 150 of FIG. 1), which can be a personal computer or a laptop computer. This data transfer can be accomplished via a wireless interface, which can allow a sports participant great mobility, even while connected to the electronic sensors and/or MCU. As illustrated, the personal computer can receive the data, store and/or analyze the data. In some embodiments, the first processor is an interface box 153. Thus, in some embodiments, after the data and/or information is processed, the results are transmitted to the interface box 153, which in turn communicates the results to the user (e.g., a golfer).

Figure 5A:
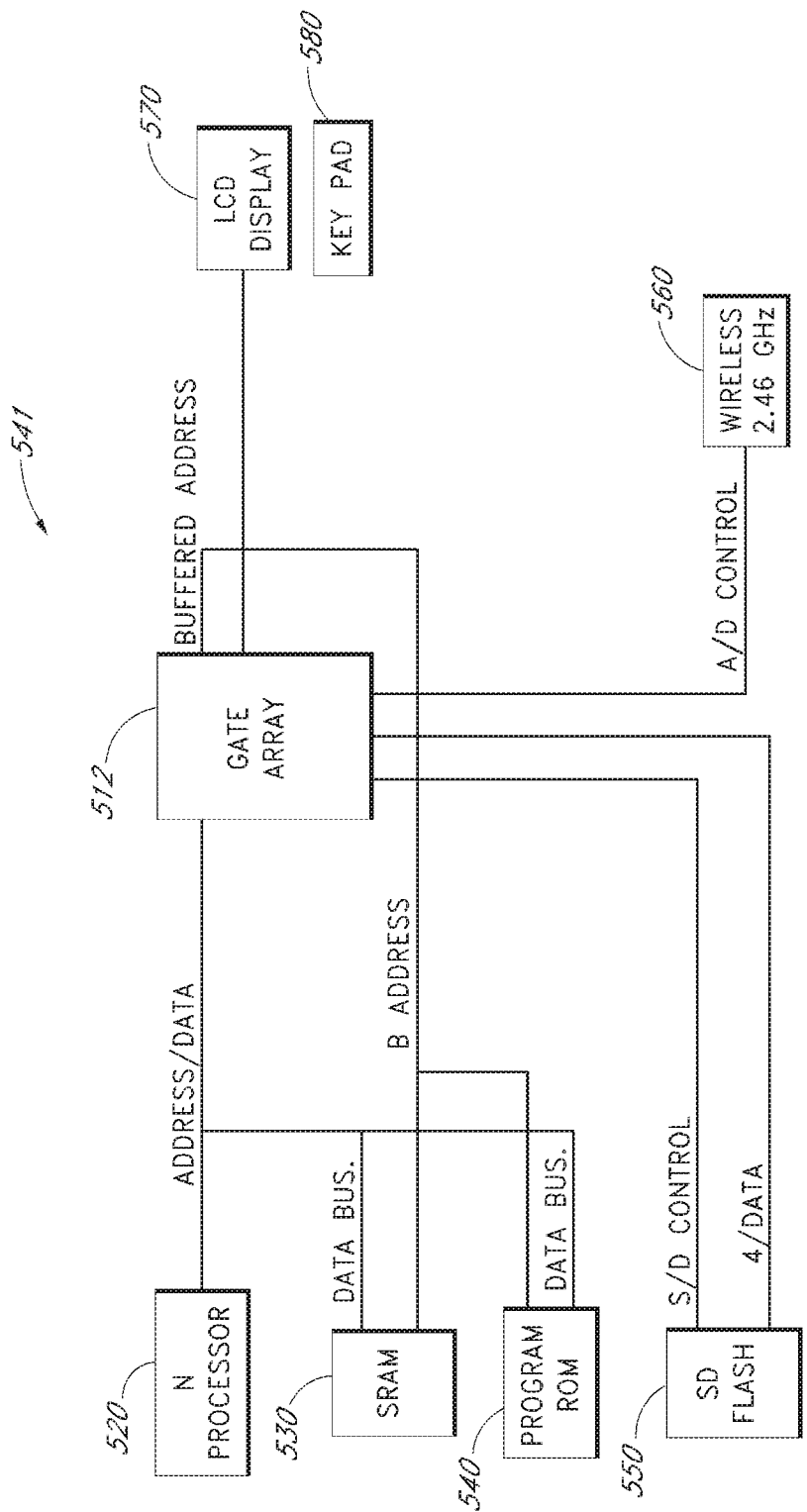
FIG. 5A is a block diagram that schematically illustrates subcomponents of an MCU and schematically illustrates connections along which data and/or signals can travel between those subcomponents.

FIG. 5A schematically illustrates examples of subcomponents of an MCU 541 (e.g., the MCU 141) and shows connections along which data and/or signals can travel between those components. The subcomponents of the MCU 541 can be implemented with suitable electronic components including a field programmable gate array (FPGA), a complex programmable logic device (CPLD), and/or a programmable logic device (PLD). Although not illustrated in FIG. 5A, data from sensors (e.g., the sensors 131) can flow into the depicted gate array 512. Data and/or address information can flow from the gate array 512 to the N Processor 520, the SRAM 530 and/or the program ROM 540 as shown, using a data bus, for example. Buffered address information can flow from the gate array 512 to the SRAM 530 and/or the program ROM 540 as shown. The SRAM can provide temporary storage of data (e.g., for buffering). Control signals and other data can also flow to and from the SD flash memory 550 from the gate array 512. To or from the gate array 512, analog/digital control signals and other data can flow from or to a wireless device 560 (e.g., a 2.46 gigahertz device), which can transmit or receive data to other wireless devices. An LCD display 570 and a key pad 580 can also be connected to the gate array 512, and data from memory (e.g., the program ROM 540) can be displayed on the LCD display 570.

Figure 5B:
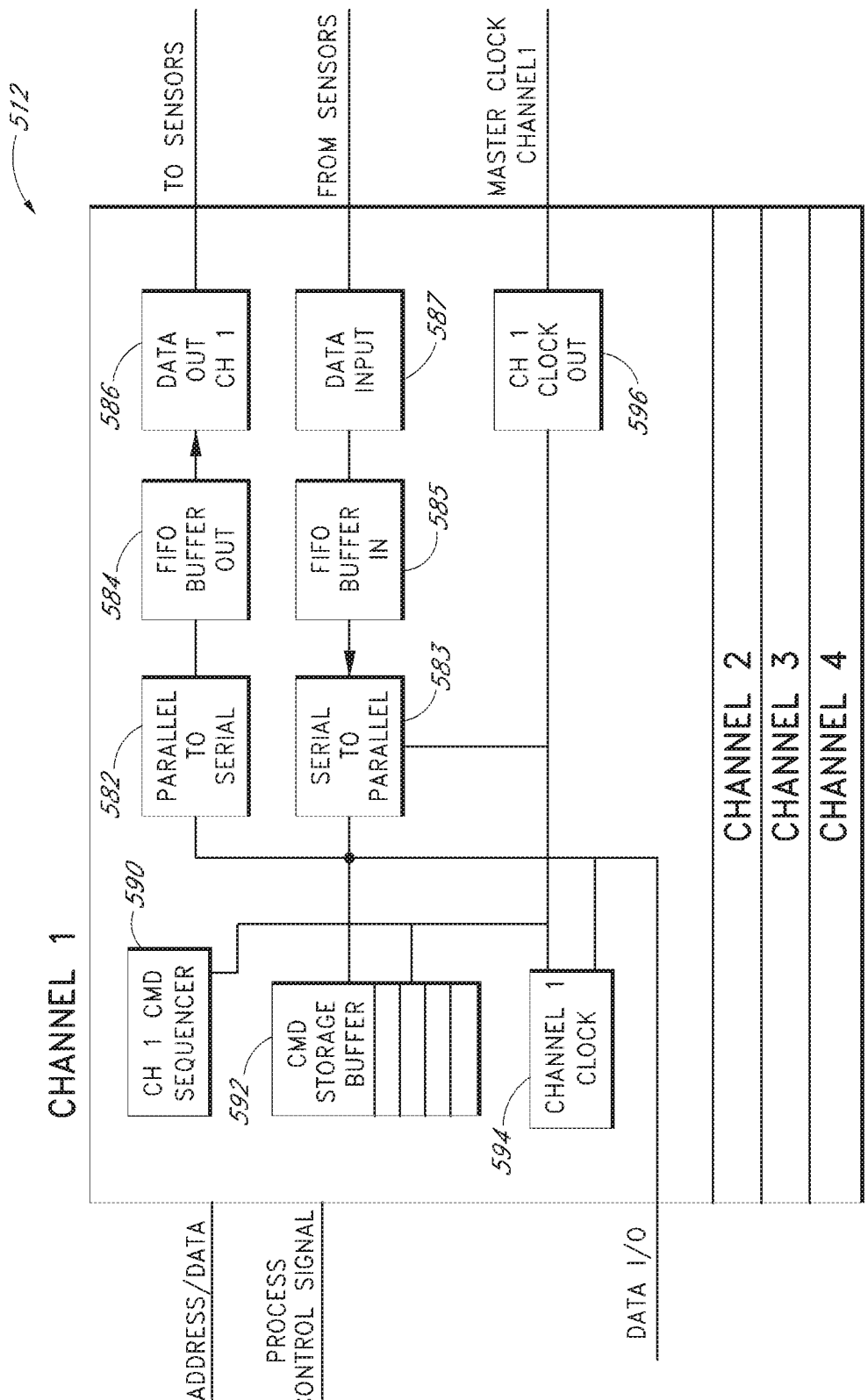
FIG. 5B is a block diagram that schematically illustrates subcomponents of a gate array.

FIG. 5B schematically illustrates examples of subcomponents of a component (such as the gate array 512 shown in FIG. 5A.) Data and signals to and/or from sensors can flow into the illustrated component, Channel 1 is shown, and channels 2-4 can have similar components and layouts. For example, each channel can have a parallel to serial component 582, a first-in, first-out (FIFO) buffer out 584, and a data out component 586, which can send data to outside components (e.g., sensors). Each channel can also have a serial to parallel component 583, a first-in, first-out (FIFO) buffer in 585, and a data input component 587, which can receive data from outside components (e.g., sensors). The FIFO buffer out 584 can, in some embodiments, exchange places with the parallel to serial component 582. Similarly, in some embodiments, the FIFO buffer in 585 can exchange places with the serial to parallel component 583. The parallel and serial component 582 and the serial to parallel component 583 can be connected to a command storage buffer 592, which can also be connected to a channel one command sequencer 590. The channel one command sequencer 590, as well as the command storage buffer 592 and the two parallel/serial components 582 and 583 can be connected to a channel one clock 594, which is in turn connected to a channel one clock out 596. In some embodiments, the component (e.g., the gate array 512) can include a microcontroller, which can be programmed to generate an executable set of commands. For example, the commands may enable signal processing (e.g., filtering) of the data received from the sensors.

Figure 5C:
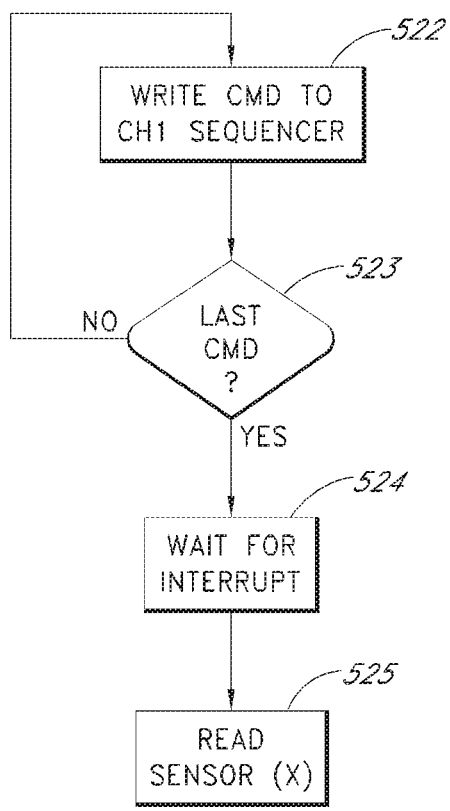
FIG. 5C is a flowchart that schematically illustrates a process that can be performed by the gate array.

FIG. 5C schematically illustrates a process that can be performed by a component (e.g., the gate array 512 of FIG. 5B). In some embodiments, a command can be received, and that command can be written to a channel one sequencer 590, as shown at 522. The system can then determine if the command is the last one, as shown at 523. If not, the system can iterate, writing the next command to the sequencer 590, as shown at 522. However, if the command is the last command, the system can wait for interrupt, as shown at 524, and read a sensor (e.g., sensor x), as shown at 525. The sensors read can be the sensors 131, for example.

Figure 5D:
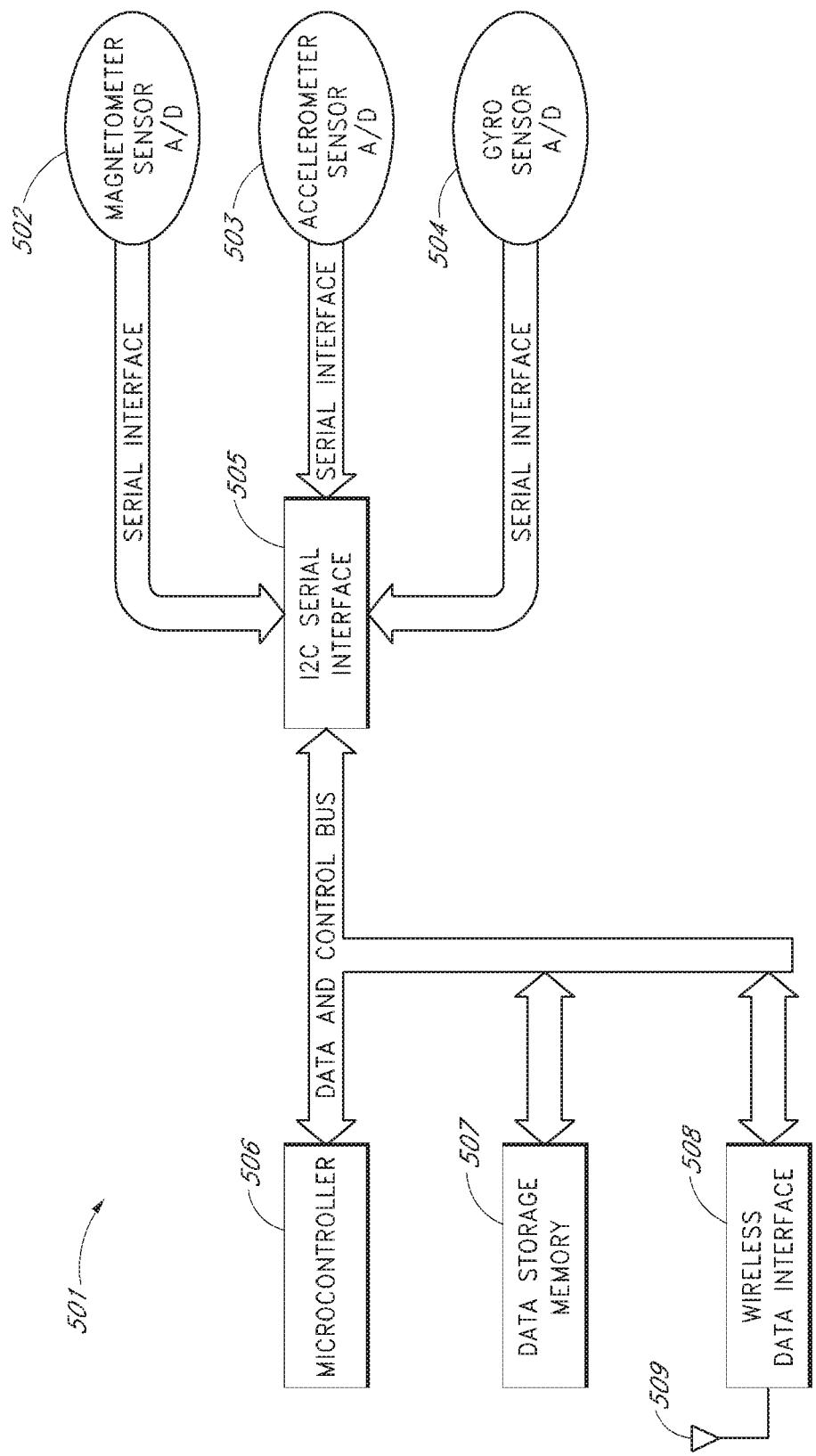
FIG. 5D is a block diagram that schematically illustrates an embodiment of a wireless sensor.

FIG. 5D is a block diagram that schematically illustrates an embodiment of a wireless sensor 501. The wireless sensor 501 can be implemented using electronic circuitry including, for example, an FPGA or CPLD. The wireless sensor 501 comprises a magnetometer 502, an accelerometer 503, and a gyroscopic sensor 504 attached via serial lines to a serial interface 505 (e.g., an inter-integrated circuit (I2C) serial interface), which communicates via a data and control bus with a microcontroller 506. The sensors 502-504 may include analog-to-digital converters. The microcontroller 506 can act as the bus master and coordinate the flow of data, for example, to on-board data storage memory 507 and to a wireless data interface 508 for transmission to a wireless data network via an antenna 509.

B. Golf Methods

Figure 6:
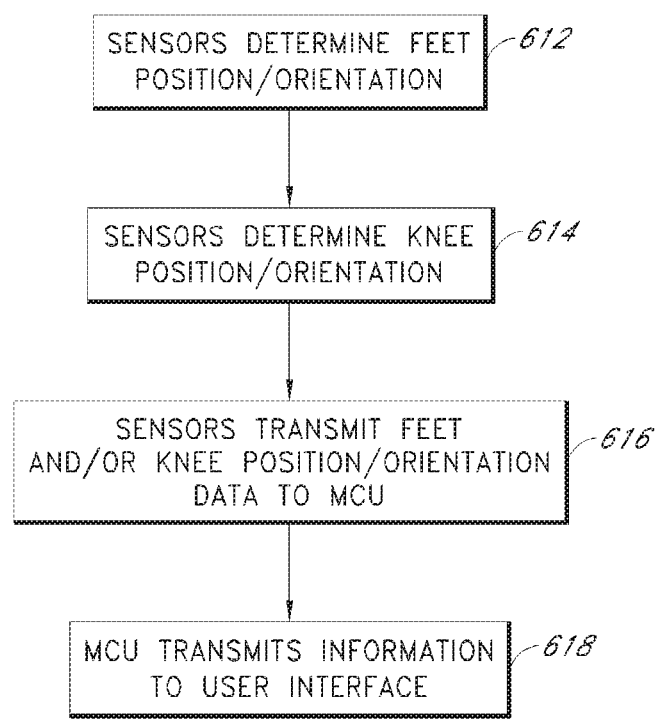
FIG. 6 is a flowchart that illustrates one method of determining whether a person's golf stance, alignment, and/or swing meets certain criteria.

In some embodiments, optical or other sensors can be used to determine whether a person's golf stance meets a certain criteria. An example process is illustrated in FIG. 6. For example, sensors can help determine the distance between and/or orientation of two feet of a golfer as shown at 612. In some embodiments, a position and/or orientation of a knee is also detected or determined as shown at 614. In some embodiments, sensors can be used instead of a yardstick to determine separation distance and/or orientation of a user's body. Sensors may transmit data to an MCU, as shown at 616. The MCL 141 can comprise a user interface, or it can transmit data relating to feet and/or knee position and or orientation to a separate user interface, as shown at 618. A user interface can be, for example, a device worn on the belt of or located in the pocket of a user, and the device can emit a sound to alert the user to correct or incorrect stance and/or positioning, for example. In some embodiments, a user can determine correct stance and/or positioning using one or a plurality of markings on a user's golf club that has been marked to show proper distances. The golf club thus marked can act as a template or measuring device that can be used instead of a yardstick, for example.

Figure 7:
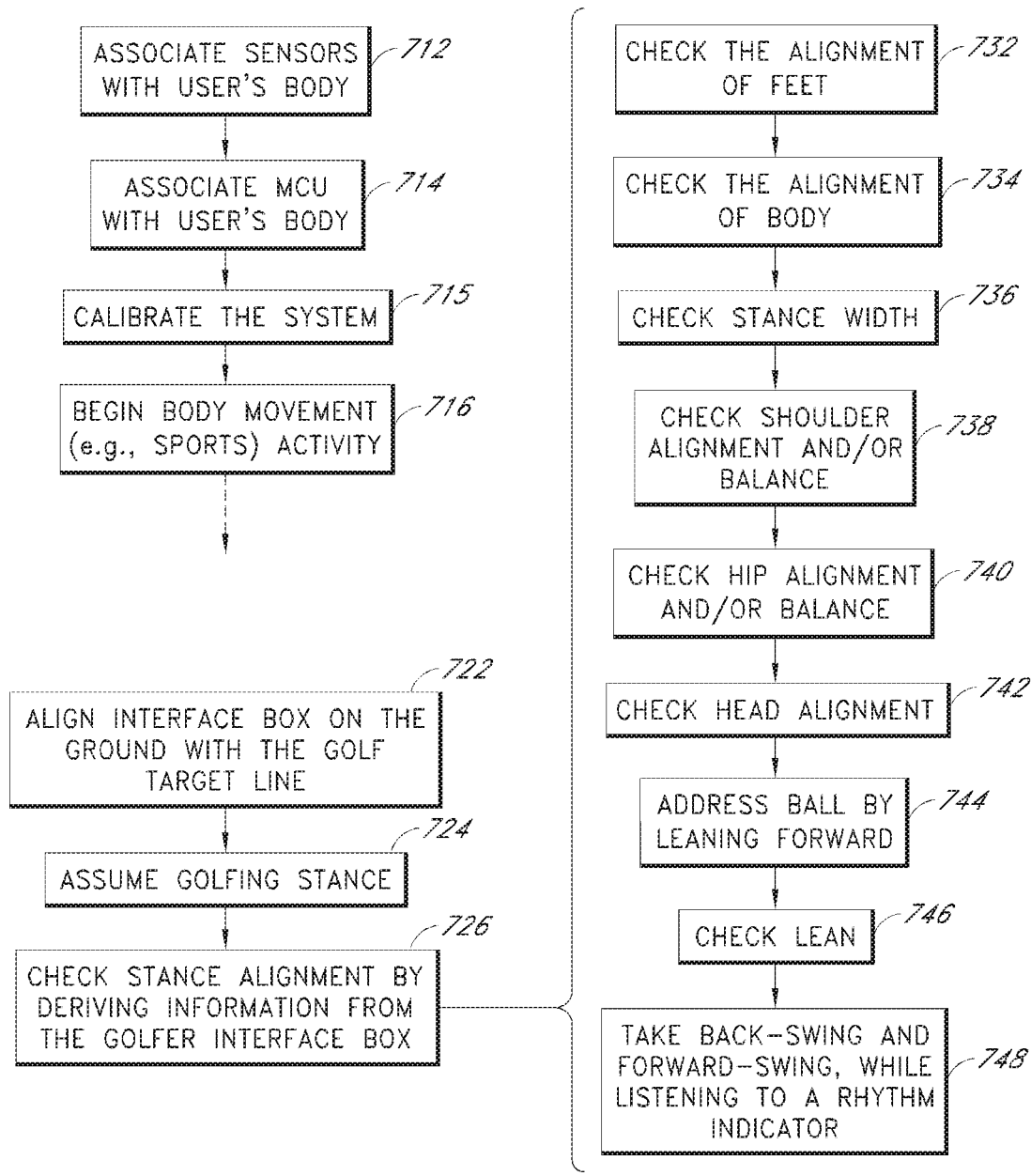
FIG. 7 is a flowchart that illustrates a, process by which a person can use the system of FIGS. 1A and 1B to evaluate his or her golf swing.

As illustrated in FIG. 7, a subject/user (e.g., a golfer) can follow some or all of the following steps to make use of a device such as those described above. A golfer can associate the sensors 131 with his body 712 by attaching them to his skin or placing them in pockets on his clothing. The golfer can then associate the MCU 141 with his body 714 (e.g., by clipping the MCU 141 to his belt). The golfer can then calibrate the system 715, e.g., by standing erect, with his back held straight against a vertical surface such as a door frame, with shoulders parallel to the ground and hips parallel to the ground (such that his left and right shoulders are each located generally the same distance from the ground, and such that his left and right hips are located generally the same distance from the ground). When this balanced, erect position is assumed, the golfer can push a button or otherwise communicate to the system that a calibration position is achieved. The system can then measure subsequent positions relative to the calibration position.

With continued reference to FIG. 7, after calibration, the user is ready to begin a sports activity (e.g., golfing). The golfer can ascertain the golf target line and place the interface box 153 on the ground such that the line 312 is aligned with the golf target line as shown at 722. The golfer can assume a golfing stance 724 by standing on the opposite side of the ball from where the interface box 153 is placed. The golfer can then check his alignment 726 by looking at (or listening to) the golfer interface box 153.

With continued reference to FIG. 7, the various aspects of proper alignment can be checked in various orders. For example, the golfer may first check the alignment of his feet 732 by observing the left foot alignment indicator 324 and the right foot alignment indicator 326. The golfer can also check the alignment of his body 734 using the body alignment indicator 322. The golfer can check his stance width 736 by observing the stance width indicator 332. The golfer can also check his shoulder alignment and/or balance 738 by referring to the shoulder LED 334, check his hip alignment and/or balance 740 by referring to the hip LED 338, and check his head alignment 742 by referring to the head LED 332. The golfer can then address the ball 744 by leaning forward, and check to see that the lean is correct 746 (e.g., that the head is up at the proper angle) by referring to the mid-back LED 336. The golfer can then take his back-swing and forward-swing 748, while listening to a rhythm indicator through the speaker 340, for example.

In some embodiments, the data produced and/or transmitted by the first processor 150 and/or the second processor 160 (see FIG. 1) can be stored, processed, and analyzed by a user (e.g., second user 162) that is different from the first user 152. The second user 162 can be a company that sells the data (in raw or processed form) to other users. The second user 162 can also perform research using the data to show statistical trends or quantities. Data can be used to in medical research studies, physical therapy studies (relating to both pre- and post-injury periods) to analyze a patient's recovery cycle, in addition to many other possible applications. The data collection, storage, processing, analysis, etc. can be accomplished as follows.

C. Data Collection Methods

An advantageous embodiment of the present invention comprises hardware and software that can measure body movement. The hardware and software can be inexpensive to manufacture. In some embodiments, a device can capture training data that reflects an athlete's or a patient's progress and/or training history. A system that can collect and store such historical data can become more and more valuable to a user over time, because a user may desire to see his or her own trends or patterns. Such a system can also have value to a data collection entity, because a data collection entity can provide research services (e.g., comparing the user's data to other users' data, comparing to the average user, comparing to a standard selected or designated by a coach, etc.) A data collection entity can also provide consulting services (e.g., providing automatic and/or personalized analysis of data, providing ways to improve accuracy and/or reliability of data, providing ideas of how to use the data collection device more effectively, etc.) A data collection entity can also provide performance enhancement services (e.g., advice on how to improve performance, training, etc.) Data collected during these activities can be stored and analyzed (e.g., to allow for better averages, better comparisons, more robust statistical analysis, etc.) The data can also be licensed and/or sold to other users such as researchers, coaches, scouts for professional athletics, etc., and can be used for many purposes (e.g., physiological studies, medical studies, sports performance studies, rehabilitation studies, etc.) In some embodiments, that data can allow research to be done on trends or averages of biometric data across various demographic groups. This data can be valuable, for example, to physical therapists attempting to analyze various treatment methods and/or to coaches researching improved training or coaching techniques. This data can be valuable, for example, to establish new industry benchmarks or indices or to establish normal or exceptional performance parameters.

In some embodiments, the data can be protected by separating the name of the user from which the data originated and the stored data itself. For example, the data can be stored by identification number, and approval can be required before the name and the data are associated. Permissions can be tracked and stored in a database. Various other encryption and password technologies can be employed to protect user data.

D. Example Data Engine

A "data engine" can be a series of computers that utilize software to collect, process, store, and/or data-mine information from the data collected using systems as described above (e.g., movement data, balance data, position, speed, or velocity data, direction data, rotation data, etc.). In addition to this data, sensors can also monitor temperatures, heart rate, EKG, EMG, blood pressure, blood oxygen content, glucose levels, etc.

Figure 8:
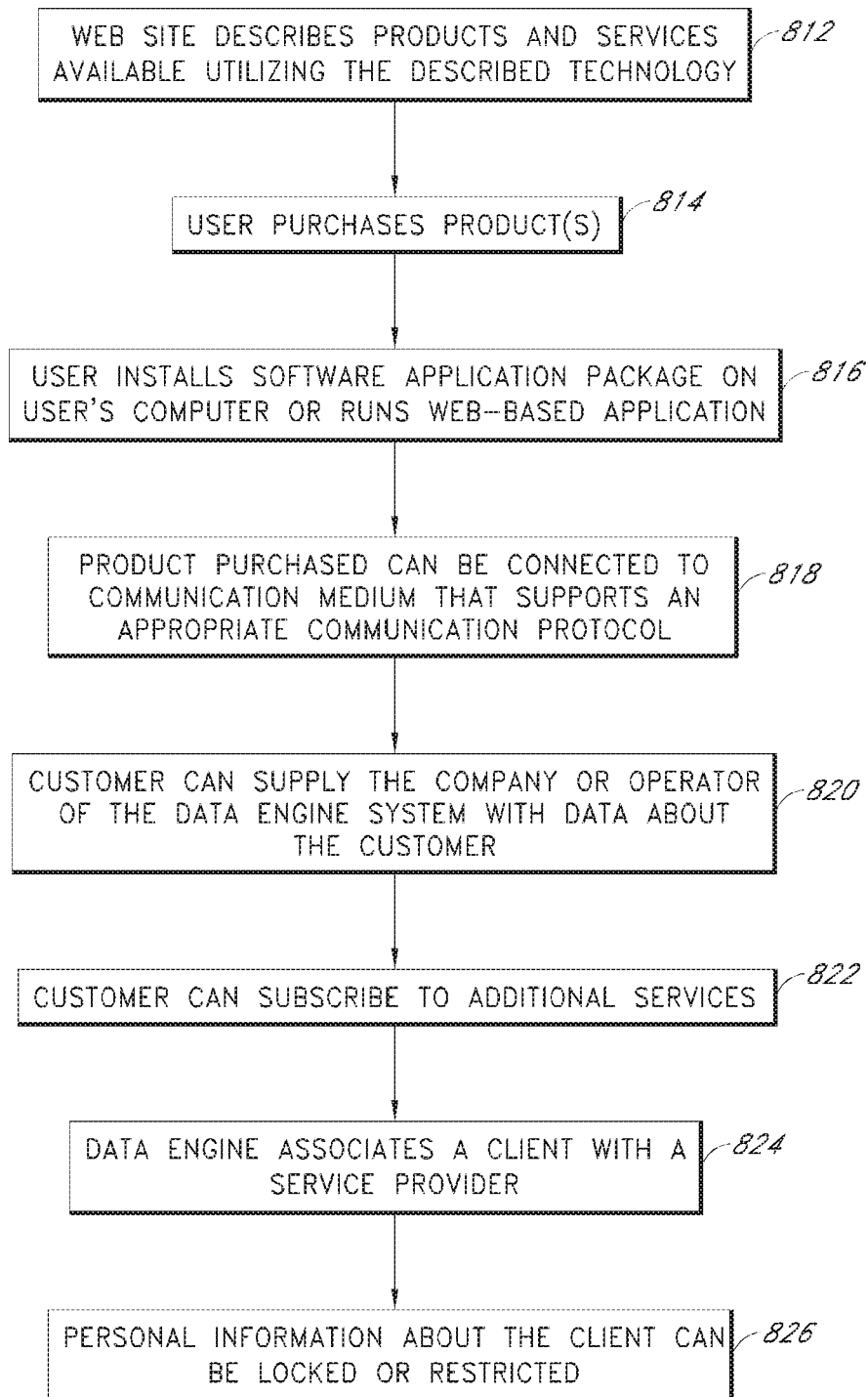
FIG. 8 is a flowchart that illustrates a method for using the disclosed system on a computer or web-based application.

As illustrated in FIG. 8, an example data collection process can start at a web site describing products and services available that utilize the described technology, as shown at 812. A customer (e.g., using an online, web-based, or telephone ordering system) can purchase products, as shown at 814, and have them delivered directly to the user's home or office, for example. The system can record information related to the user's interaction with the website and/or the user's purchase. When a customer purchases a technology that utilizes any of the described products (e.g., BodySensor products) a support software application package can be installed (e.g., by the user) on the user's computer, as shown at 816. The installation process can require the user to provide data. The product purchased may be connected with an existing telephone line, Internet connection, cable connection, or other communication medium that supports an appropriate communication protocol, as shown at 818. Using this protocol, data can be communicated to and stored by a server. In some embodiments, a customer can interact with the software, supplying the company or operator of the data engine system with data about the customer, as shown at 820. When utilizing sensor products, the customer can subscribe to additional services, as shown at 822. These services can include, for example, processing the data for a physical therapist, monitoring the training exercises of a baseball coach's players, etc.

In some embodiments, the data engine has the ability to associate a client with a service provider, as shown at 824. The service provider can be a professional in any field. For example, the service provider can be a doctor seeking to assist patients, a major-league sports team searching for athletes, etc. For example, the service provider can be a licensee and/or original equipment manufacturer (OEM) of products. Each client can be required to authorize any service provider, thus granting that service provider (or class of service providers) access to the client's information. More than one service provider can access a client's data. Personal information about the client can be locked, as shown at 826, so that service providers can not access the data without specifically requesting the locked information.

Figure 9:
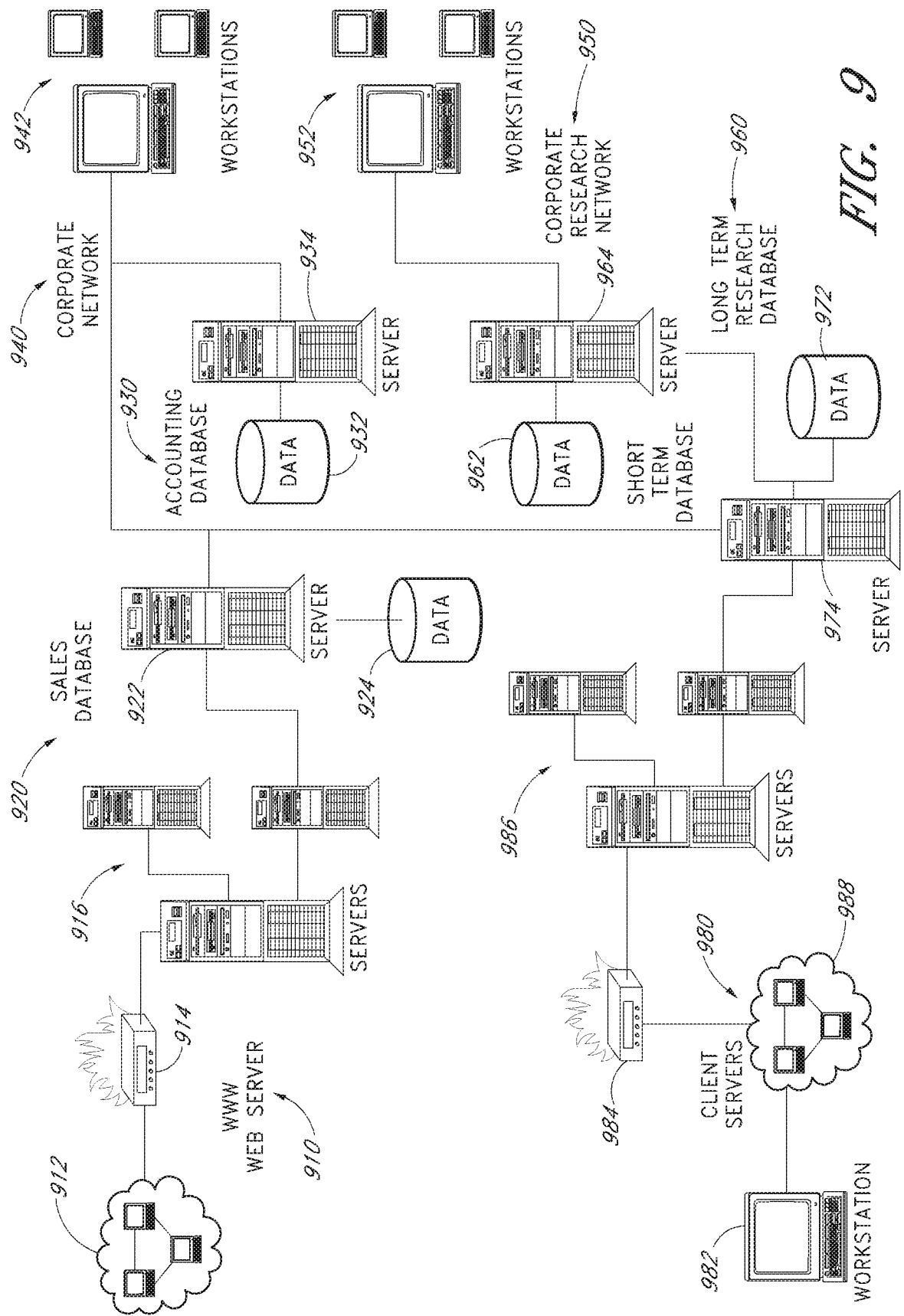
FIG. 9 schematically illustrates an example system for data collection and/or storage.

FIG. 9 illustrates an example system for data collection and/or storage. With regard to the purchase of products and services, a world-wide-web server 910 can allow users 912 to access information (through a firewall 914) from servers 916, and potentially purchase products and/or services. A sales database 920 can store client-specific information and data relating to services purchased, as shown at 922 and 924. A corporate network 940 can include an accounting database 930, accessed through a server 934, that can include the same information described above, and other information relating to billing, etc., as shown at 932. The data described above can be accessed through corporate workstations 942, for example.

With regard to body movement or other system data, client servers 980 can allow users 988 to upload and/or download data (through a firewall 984) to or from servers 986. A user's workstation 982 can be a cell phone, a desktop computer, a laptop computer, a personal digital assistant, an MCU as described above, etc. The system data 972 can be stored in a client short term database 970 using server 974, for example. In some embodiments, even if a user does not choose (or pay for) long term storage of the system data, it can be stored in a long term research database 960. The research data 962 can be accessed through a server 964 from a corporate research network 950 using workstations 952, for example.

As illustrated in FIG. 9, client and system information can stored in a number of different databases. The association of a client's name to the user ID can be stored in a secure database that can require executive level approval to access the data from the client's name and/or ID. This can guarantee the client's privacy but also allows a company administering the program to use the clients' data. In some embodiments, a client can approve a company's use of the data by agreeing to the licensing terms in a contract, for example. In some embodiments, a client may want to make his or her data available to another individual. An example is a college baseball player trying out for a major league time and the team specifically asking for data on his performance starting in high school. This type of a request can be processed either using the client's service agreement and or a contract with the major league baseball team.

1. Example Operation of a Data Engine

Figure 10:
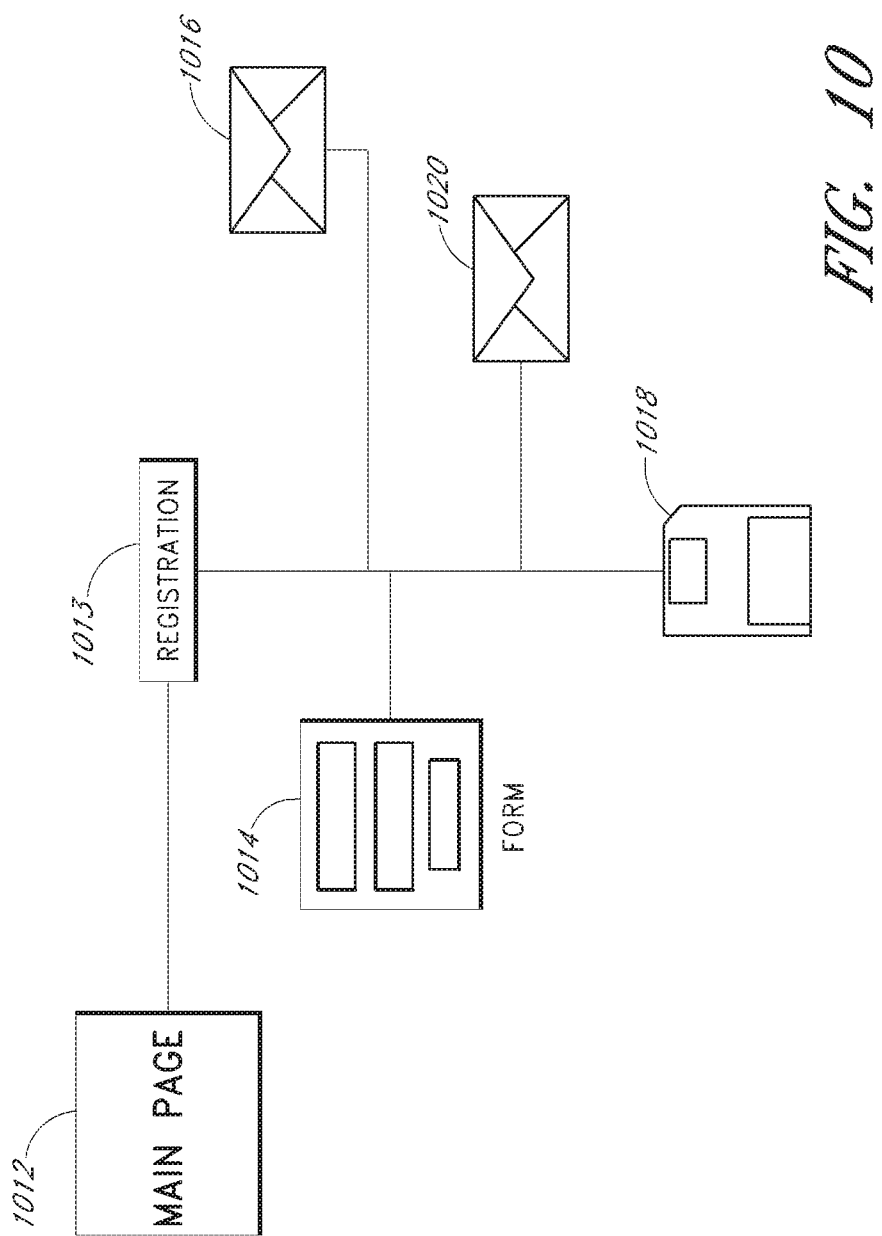
FIG. 10 schematically illustrates a data engine process.

A data engine process can begin when a user requests demonstration software or purchases a sensor product, as illustrated in FIG. 10. From a main page 1012, a user can begin a registration process 1013 and fill out a registration form 1014. Upon receipt (and/or verification) of the registration form, the system can send the user a registration code to authorize the demonstration or other program, as shown at 1016. Thus, when the customer checks out (e.g., from an on-line store) the customer can receive an authorization code that will allow him or her to download software from a Web server and install the software right away and start using it. The demonstration or other program can then be downloaded, as shown at 1018, or sent to the customer on a disc or other physical medium as shown at 1020. In some cases, (e.g., if the customer doesn't download the software), a copy of the software can be shipped with the product (e.g., sensor units). In some embodiments, the software is required to access any of the related services provided online.

FIG. 11 illustrates offline and online registration options. For example, once the customer installs the software and enters the registration code at a main page 1112, the client software can display a welcome message 1114, while attempting to connect with a services server. The registration server can request an approval for the registration code from an account authorization server. The registration code can be linked to a user's account, which can have information about which applications and/or service levels have been purchased by (or which demos have been sent to) that user. This information can be returned to the client application, enabling each item. Thus, the registration code can determine to which "business unit(s)" the user is titled to have access. Once the client applications are enabled, the client application displays a registration page (e.g., an online registration page 1116 or an offline registration page 1118) for the user to complete. The client application will send a second request to register the new user and an account ID created and the association with the sales order. Support can be supplied if the purchaser and the user are two different individuals. Online registration can enable online demonstration and level 1 access, for example, as shown at 1120. Offline registration can enable demo application from a demo CD as shown at 1122. Thus, once registered, the user can have access to all of the services purchased and any specific features that are offered to individuals that have not purchased services. Applications can be available on a corporate server 1124 for online registration, and on a CDROM 1126 for offline registration.

In some embodiments, the user can install on his or her body the sensors purchased and collect a sample of data to review. Once the data is captured, it is transferred to the client computer using either an SD Flash memory card (like a digital camera) or a wireless interface if purchased. In some embodiments, at this point the user can view the data collected and playback the motions that were captured.

The user, after capturing the data, can select the upload command and the client computer can automatically log the user into the account ID that was registered. In some embodiments, all of the data captured can be automatically uploaded when the authorization is approved to the appropriate file server. The data stored on the appropriate file server can be available for a time (e.g., about 90 days or about 30 days or about 60 days) before it is transferred to the Long Term Research Database 960 (see FIG. 9) where it can be stored indefinitely. In some embodiments, some data about the user can be stored that can reveal information about the user including all physical measurements, age, sex, etc. These data can be used when searching for specific age or height groups for research studies. Customers can request services to be performed on their data. For example, a customer's golf backswing can be analyzed (e.g., to determine why the customer's golf game has changed in the last two week or months). The Long Term Research Database 960 (illustrated in FIG. 9) can contain all of the customer records and can be used to search for contracted data types. The research group can convert company-specific data formats to customer-specific requirements.

Figure 12:
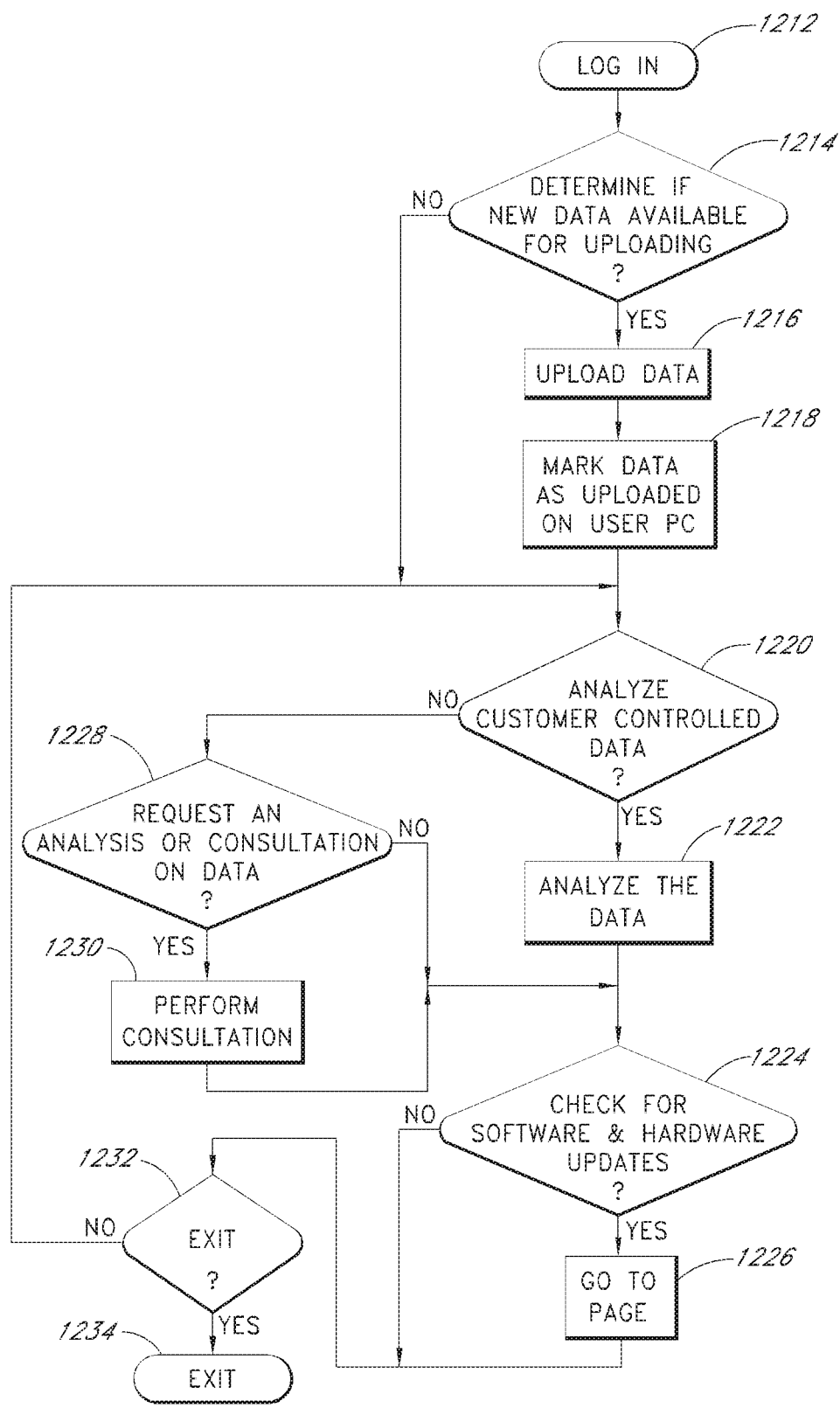
FIG. 12 is a flowchart that illustrates a process by which a user can exchange data and obtain an analysis or consultation from a network based application.

As illustrated in FIG. 12, a web server (WS) (e.g., the web server 910 or client servers 980 shown in FIG. 9) can give users and/or customers access to various aspects of communication with the provider (e.g., a company) and the provider's "learning center" to satisfy the user needs. New users can build accounts that allow additional users (max number per license) access to different support levels. In some embodiments, all software update and customer upgrades can be handled using the WS. In some embodiments, the WS can be configured to be easy to use for any person with or without computer knowledge.

In some embodiments, a user may log in 1212 to a server (e.g., using a username and password) and gain access to a data storage and analysis page. The system can determine if any new data is available to be uploaded to the server, as shown at 1214. If not, the system can proceed to analysis steps discussed below (e.g., at 1220), but if so, the data is uploaded, as shown at 1216. Once uploaded, the data on the user PC can be marked as uploaded, as shown at 1218.

The system can prompt the user to indicate if the customer-controlled should be analyzed, as shown at 1220. If so, the data can be analyzed by the user (or the user's PC), as shown at 1222, but if not, the user can be prompted to request or decline an analysis or consultation on data as shown at 1228. If requested, the consultation is performed, as shown at 1230. The data analysis options can be offered based on level of service a customer has purchased. The data can either be "raw" data that the user analyzes independently (with or without the help of the user's system or personal computer, for example) as shown at 1222, or it can be analyzed by a consultant or another server, as shown at 1228 and 1230. An analysis report can be sent to the user. Alternatively, a coach can have access to the data of a user and perform evaluations and analysis of the data.

At this point, the system can check for software and hardware updates, shown at 1224. If there are updates, the system can go to an update page 1226 that provides the user more information about those updates and allows software updates to be ordered, downloaded, etc. Information can be provided to the user about new products or the user can also be directed to an on line store, for example. If there are not updates, or once any updates have been installed or declined, the system can prompt the user, as shown at 1232, about whether or not to exit 1234. If a user declines to exit, the system can repeat the analysis steps, beginning at 1220, as shown. If a user elects to exit, the connection to a web server can be closed with a message thanking them for using the services, with further company contact information offered by email response, or via a customer representative telephone number.

In some embodiments, an athlete's performance can be enhanced and research can be advanced using data collected from that, athlete. Furthermore, an athlete can receive consulting services that can be automated or personalized.

2. Example System Configuration for Use with a Network

Figure 13A:
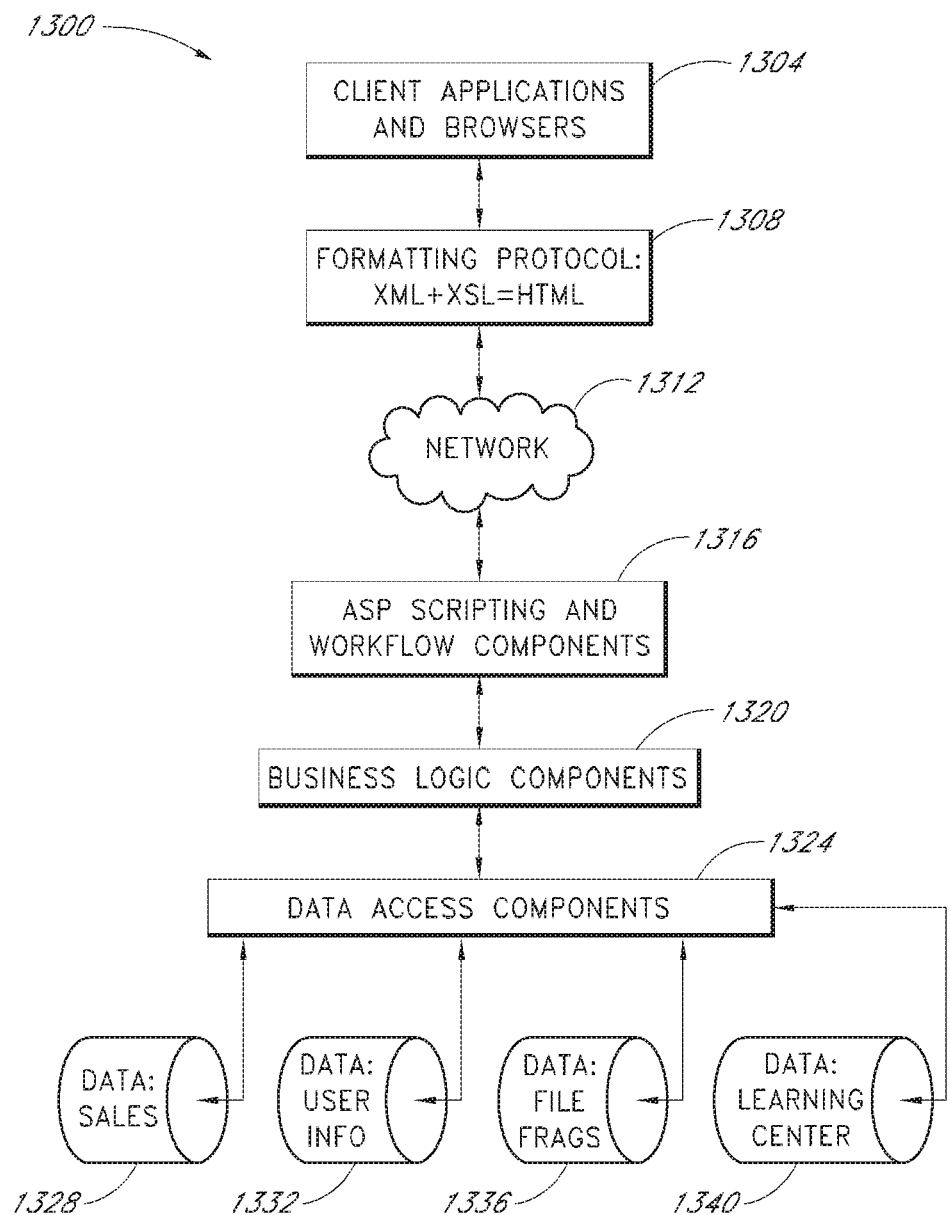
FIG. 13A schematically illustrates an example client/server system that provides communication between a user and a host server through a network.

FIG. 13A schematically illustrates an example client/server system 1300 that provides communication between a user and a host server through a network. The system 1300 can be used to transfer biometric and biomechanical data, biomechanical performance fingerprints, biometric instruction, images, video, audio, and other information between a user and the host server. The system 1300 can be implemented in the context of the systems shown and described with reference to FIG. 9 (and with FIGS. 14 and 15 described below).

In block 1304 of FIG. 13A, the user can interact with the system 1300 with a client application such as, for example, a browser that can display text, graphics, multimedia data, etc. The client application can run on a processor such as a personal computer, cell phone, personal digital assistant (PDA), pocket PC, or other portable communications and/or computing device. The client application may include a static and/or dynamic user interface (e.g., an HTML or ASP-based browser). Information may be transferred over a network 1312 using a suitable formatting protocol that enables the definition, validation, and/or interpretation of data. For example, information content may be described using an extensible markup language (e.g., XML or SGML), and the format or style of the information can be described using an extensible style language (e.g., XSL). In some world-wide-web applications, hypertext markup language (HTML) is used. The formatting of the client side applications, browsers, and information can be selected to provide a "user experience" that makes it easy for the user to transfer information between the client applications and the server applications.

The network 1312 may be any suitable network suitable for communicating data and information such as, for example, the Internet or a telecommunications network such as a cell phone network. Information is communicated via the network 1312 between the client applications (in block 1304) and the host server system (in blocks 1316-1340). The host server may include one or more processors (e.g., server computer systems, workstations, and/or mainframes) that implement the server functions. For example, the server system may include a business logic layer indicated in blocks 1316 and 1320 that provides a set of data management functions and business specific logic. For example, the business logic layer may determine an access level for the user which determines, in part, the data the user can access and the functions the user can invoke. The business logic layer may include server-side scripting such as, e.g., active server pages (ASP) scripting and other data resource management workflow components. Other scripting languages such as Perl, Java. Server Pages (JSP), or hypertext preprocessor (PHP) are used in other implementations.

The system 1300 also includes a data layer in block 1324 that provides the business logic layer (blocks 1316 and 1320) with access to data stored in one or more databases. For example, data may be stored in a sales database 1328, a user information database 1332, a file fragment database 1336, and a learning center database 1340. The business logic components in block 1320 may include a database management system (DBMS) that provides database access and manipulation functions. In some implementations, a structured query language (SQL) is used to implement the database functions, and information from queries is returned in XML format. The databases 1328-1340 advantageously may be stored in normalized form (e.g., 3NF) to reduce or minimize data redundancy, data restructuring, and input/output (I/O) rates by reducing the transaction size. Additionally, the DBMS may enforce referential integrity to prevent users or components from entering inconsistent data in the databases 1328-1340. In some implementations, one or more of the databases 1328-1340 may comprise short term storage and long term storage as discussed below with reference to FIG. 14. In order to maintain privacy of a user's biomechanical data, it is advantageous to structure the databases 1328-1340 so that the data is associated with a unique user identification string but not with the user's personal name or address.

In certain embodiments, the sales database 1328 includes information related to purchase of biometric and biomechanical products and services by a user. For example, the data may include user identification information, user address and contact information, user payment information, and user purchase information. The user information database 1332 include user-specific information needed for certain biometric and biomechanical applications such as, for example, a user's gender, birth date, height, and weight. The user information database 1332 may also include a user-type to identify a category for the user (e.g., player, team, coach, trainer, billed user, patient, medical provider, etc). Users of the system can have various identified relationships between or among each other, for example: player/coach; player/billed user; player/team; player/medical provider; player/trainer, etc.

The user information database 1332 may also include information related to the user's body such as the length or size of the user's arms, legs, torso, waist, etc. Such information may be further subdivided into, for example, the user's forearm and upper arm length, hand length, wrist size, etc. User body information such as this may be measured during an initial calibration session with the user, or such information may be measured from a garment used to hold the sensors (e.g., the garment 200 shown in FIG. 2A). User body information may be updated as the user ages or as the user's body shape changes. User body information stored in the user information database 1332 may be used to calculate sensor positions and orientations (e.g., via the quaternion methods described above).

The file fragment database 1336 contains information for storage and retrieval of user files. For example, in one implementation, a root folder is created to store data records and information generated during a particular day. Each day a new root folder is created, up to a maximum of N root folders. For example, in one embodiment, N can be set to 90 to store ninety days of data. When a new root folder is created, data stored in the oldest root folder may be deleted or may be archived in a long term database (e.g., the long term research database 960 shown in FIG. 9; see also the discussion of short term storage 1462 and long term storage 1464 below with reference to FIG. 14).

The learning center database 1340 may include information related to the user's biometric and/or biomechanical movements (e.g. a golfer's swing, a pitcher's throw, a patient's movements during rehabilitation). For example, the learning center database 1340 may include a time sequence of acceleration, velocity, position, and/or orientation data read out from some (or all) of the sensors while the user performs a movement. The business logic components in block 1320 may include executable program components that access the biometric data in the learning center database 1340 so as to provide a biometric analysis of the user's movements. For example, the biometric analysis may provide a performance fingerprint, graph, chart, or video. The biometric analysis may include statistical data (e.g., histograms, performance comparisons to a suitable population, etc.) by which the user can track his or her biometric progress.

The client/server system 1300 shown in FIG. 13A can be used to transfer user data into the databases 1328-1340 and/or to access, modify, and extract data from the databases 1328-1340. For example, the client applications in block 1304 can run on a user's cell phone and the network 1312 can be a cell phone network. The user can access program components (block 1320) that calculate the user's performance fingerprint (or other biometric information) from the user's biometric data stored in the learning center database 1340. The performance fingerprint (or other biometric information) can be transferred back through the cell phone network 1312 for audio and/or visual display on the user's cell phone. Many variations are possible and some variations are discussed below with reference to FIGS. 14 and 15.

Figure 13B:
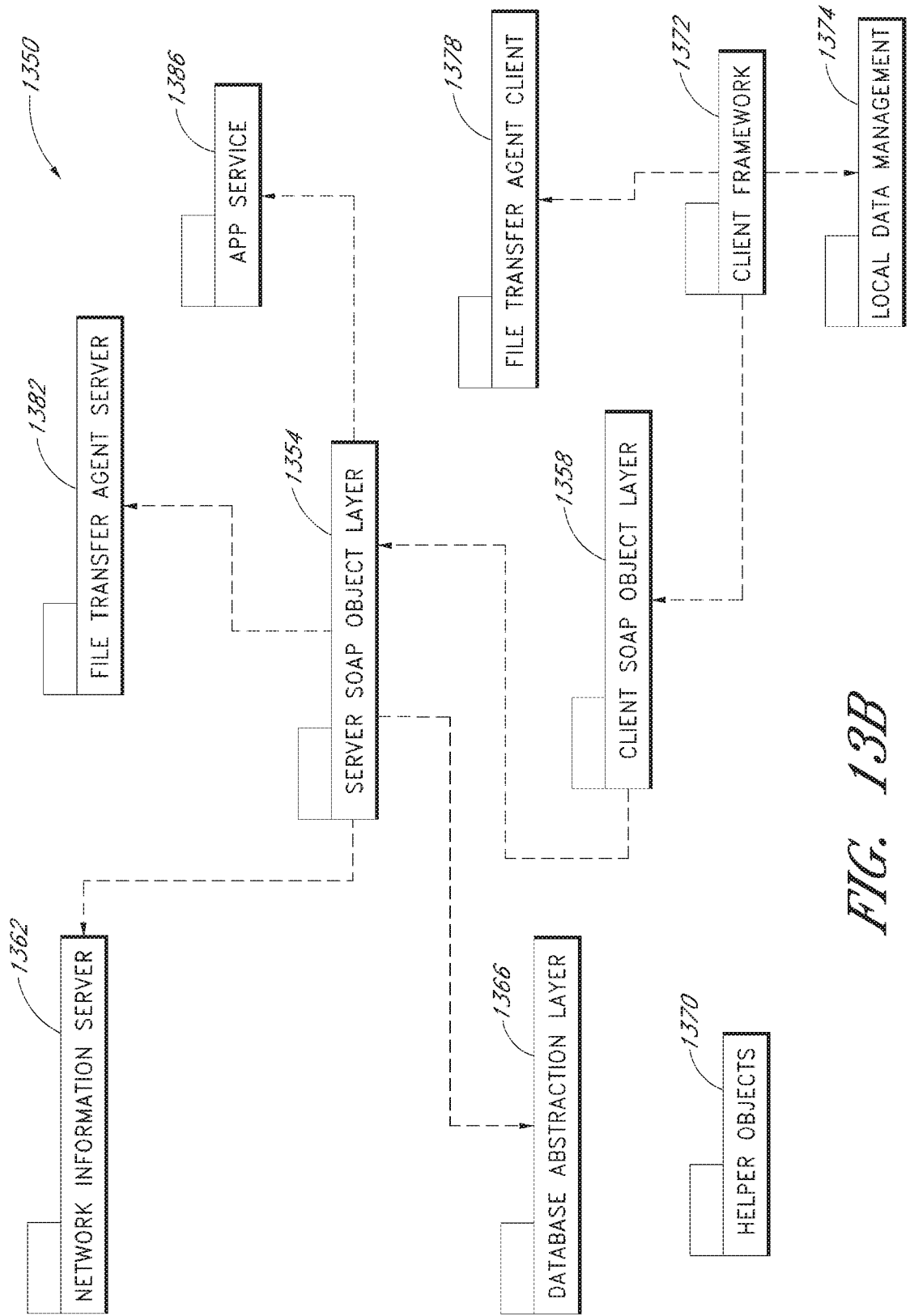
FIG. 13B is a unified modeling language (UML) diagram schematically illustrating an abstract model of a software architecture that may be used to implement the client/server system of FIG. 13A.

FIG. 13B is a unified modeling language (UML) diagram schematically illustrating an abstract model of a software architecture 1350 that may be used to implement the client/server system 1300 of FIG. 13A. FIG. 13B schematically illustrates the flow of data and commands in the architecture 1350 and depicts abstractions and interfaces used with the business logic layer of the system 1300 (blocks 1316 and 1320). In the embodiment shown in FIG. 13B, Simple Object Access Protocol (SOAP) is used to provide an XML-based protocol for exchanging structured and typed information across the network 1312 (e.g., the Internet). Blocks 1354 and 1358 are the server and client SOAP objects, respectively, which work together to proxy calls from the client to the server and to return requested data. The client SOAP objects 1358 may be invoked remotely by the client. The server SOAP objects 1354 may be executed by the server as an extension to a Network information Server (NIS) 1362. In some implementations, the NIS 1362 is an Internet Information Server (IIS). Application service objects 1386 are provided to mediate user rights at a login session, authenticate user name and password, and to manage session tokens.

The database abstraction, layer 1366 may provide access and data formatting between a caller and the database 1328-1340. In the architecture 1350 shown in FIG. 13B, the SOAP layer is a consumer of the database abstraction layer 1366. Various helper objects 1370 may be created for each data type that is exchanged between the client and the server. For example, helper objects 1370 may monitor the progress of the data transfer, set file paths for data storage, etc. Local data management objects 1374 are used to facilitate storage of data on the user's client-side system. In some implementations, the local data management objects 1374 are configured to work like a file system in order to simplify storage requirements.

Data and files may be exchanged between the client and the server via a client framework 1372, client-side file transfer agent 1378, and server-side file transfer agent 1382. It is advantageous for the client-side and server-side file transfer agents 1378 and 1382 to share a common protocol to manage file transfers between the client and server computer systems. In some implementations the file transfer agents 1378 and 1382 manage software upgrades and exchange of motion data captured by the sensors described herein.

3. Alternative System Configurations

In some embodiments (e.g., a golf system such as the example system 109 shown in FIG. 1B), a second processor may not be included in the system. However, in some embodiments, a second processor 160 (see. FIG. 1), and/or additional processors (not shown) can also be included in the system. Indeed, various components can be included in various embodiments that can be configured for different users.

In some embodiments, a system (e.g., a "BodySensor" system) can have three components: the sensors, a Master Control Unit (MCU) (see FIG. 2 for illustrations of each), and a Software ProPack (SPP). Each component can have various (e.g., three) different configurations. For example, a lower level system can include fewer sensors, an MCU with less functionality, and an SPP with fewer or less-advanced features. In contrast, a higher level system can include more sensors, an MCU with more functionality, and an SPP with more numerous or more-advanced features.

In some embodiments, the Software ProPacks ("SPP"s) are computer programs that operate using any of a number of operating systems, including, for example, Microsoft Windows, Linux, etc. In some implementations of the system, there are three software packs having increasing numbers of advanced features: "Introductory," "Mid-Level," and "Professional." The three packs may be provided as three separate software packages or as three different modes within a single software package. In other implementations, fewer or greater levels of features may be provided. Each software pack provides the customer with access to certain levels of provider services. For example, each software pack can allow the user to log-in to the provider's web site and, based on the user's service level, obtain updates to the MCU, the sensors, and/or the SPP features.

In one implementation, non-limiting examples of three SPP packs (or modes) are the following:

An Introductory SPP is designed for a personal user and can allow a user and/or a web service to track the movement and position of the arm and upper torso. Movement tracking is accomplished in one embodiment by positioning four sensors at different locations on the arm. For example, sensors can be located on the back of the hand, on the lower forearm, on the upper forearm and on the rear side of the shoulder. Each of the sensors can be connected to an MCU 141 that collects, monitors, and stores data. The Introductory SPP may support monitoring of fewer (e.g., only one) sensor. The user can utilize the provider's services to compare new data to previously stored data and obtain professional services to analyze the data and/or to make personalized recommendations on improvements.

A Mid-Level SPP can offer enhancements over the Introductory SPP including, for example, functionality to gather and process data from an additional set of sensors for the opposite arm. The second set of sensors can allow the MCU 141 to monitor and store collected data for the upper body, including waistline motion, for example. The user may have access to more local analysis of data and the ability to set multiple data points to monitor and view. The user can have increased access to the provider's consulting services.

A Professional SPP can have all the functionality of the Mid-Level SPP and can also include functionality to gather and process data from additional sensors attached to the user's lower body. Lower body sensors can include ankle, lower leg, and upper leg sensors for each leg. The Professional SPP may provide increased access to professional trainers, swing coaches, and the like.

The software ProPacks can be executed by a computing device (e.g., the first processor 150 or the second processor 160 [see FIG. 1]), which can execute the functions illustrated in the figures and described herein. The SPP may allow a user to monitor and play back a recorded event (e.g., a golf swing or a baseball pitch) in real time or slow motion, for example. A user can manipulate an image corresponding to the recorded event in order to view it from any three-dimensional position. The recorded event may correspond to recorded movements of the user or recorded movements of another person such as, a teammate, an instructor, a trainer, a professional, etc. The user can invoke a reference point for comparing his or her data to an existing stored reference (e.g., the user's or another's recorded events). The user may compare his or her training exercise to the stored reference to determine potential for improvement, for example.

Embodiments of the described invention can also be helpful in the prevention of both serious and minor injury among sports participants. Such injuries may include painful joint, tendon, & muscle injuries, and more. One advantageous function is to improve performance, training, technique, and confidence. The product may also serve to protect its wearer from the more severe outcomes resulting from incorrect techniques over time. Injuries caused by poor techniques in athletics are a serious problem. Furthermore, recovery rates from injuries caused by improper techniques are poor and recovery techniques can cause further injury. Recovery techniques can be less valuable than prevention techniques when muscle, joint or tendon damage occur. Injuries produced by trauma can be more related to function than biological structure. Trauma may produce a variety of muscle, electrical & physiological abnormalities.

Embodiments can be used in gaming to track the movements of the body of a game player. Instead of using a controller that is hand-operated, for example, a player can move his or her body in a way to control the player's character in a game. Information can be transmitted from the sensors on a player to a processor (e.g., an MCU) as described above with respect to sports embodiments (e.g., wirelessly).

III. Wireless Communication Systems and Methods

FIG. 14 illustrates an example system 1410 with components that can communicate data wirelessly. The illustrated system 1410 is similar to that described above with respect to FIG. 1B. The system 1410 can include a wireless telecommunications device 1412, e.g., a mobile telephone or a cellular phone ("cell phone"). The wireless telecommunications device 1412 can function as the transceiver 140, the first processor 150, and/or the second processor 160 of the system 110 (see FIG. 1). The wireless communications device 1412 may be a disposable cell phone or a prepaid cell phone. The wireless telecommunications device 1412 may be capable of transmitting and/or receiving electromagnetic signals (e.g., RF signals). The wireless telecommunications device 1412 may include a visual display having, for example, text and/or graphics capabilities. Graphics capabilities can include two-dimensional graphics and/or three-dimensional graphics.

The telecommunications device 1412 can include internal data storage and/or one or more internal processors. In some embodiments of the system 110, some or all of the processing of the signals from the sensors 140 is performed by the wireless telecommunications device 1412. The wireless telecommunications device 1412 can be used to transmit data, images, graphics, messages, etc. between the first and second users 152 and 162 (see the arrow 116), between either of the processors 150, 160 and the users 152, 162 (see the arrows 114, 115), and/or between the sensors 130 and the transceiver 140, and/or between the transceiver 140 and the first processor 150 (see the arrow 112). Many variations are possible, and the aforementioned description of the telecommunications uses of the device 1412 is intended to be illustrative and non-limiting. It is recognized that the wireless telecommunications device 1412 can be used for virtually any component of the system 110 wherein it is desired or feasible to receive, transmit, and/or process data.

In some embodiments the wireless telecommunications device 1412 is, for example, a conventional cell phone; however, in other embodiments, the device 1412 is, for example, a cell phone augmented or enhanced with additional processor and/or transceiver components that are configured for biometric data processing, analysis, data packetizing, transmission, or reception. For example, an expansion slot in a personal digital assistant or cell phone can be filled with microchips or other electronic devices configured to allow collection of body movement data. In some embodiments, the augmented cell phone is delivered to the end user (e.g., the first or second users 152, 162). In some embodiments, the cell phone is equipped with one or more card slots (e.g., a PCMCIA slot) that are configured for a separate biometric data device that performs suitable biometric data analysis, processing, transmission, and/or reception functions. It is preferred, but not necessary, that the biometric analysis, processing, transmission, and/or reception functions be carried out according to an industry standard or protocol so that biometric data is readily transportable from and/or between different devices 1412 and systems 110.

FIG. 14 shows one example embodiment that illustrates certain features of the system 310. In this embodiment, four sensors (e.g., "head," 1422, "upper back," 1424, "lower back," 1426, and "shoe" 1428) are attached to the user, although fewer or more sensors can be used in other embodiments. This embodiment is an implementation of a system for a user playing golf (similar to the system shown in FIGS. 1A and 1B). In other embodiments, the sensors can be configured for use with, for example, baseball, softball, swimming, tennis, or another sport or exercise. In this embodiment, wireless sensors are used that transmit signals over a suitable wireless network (e.g., Bluetooth, 802.11, RF, etc.). The sensor signals may be received by a display 1430 (e.g., the interface box 153 shown in FIG. 1B). The sensor signals may also be sent to the wireless telecommunications device 1412 (e.g., a cell phone). In some embodiments, a laptop 1440 can be connected (e.g., via a USB cable 1442 or internal wiring) to a wireless transmitter 1444 that can communicate with the display 1430 and/or the sensors 1422-1428. The wireless device 1412 (and/or the laptop 1440) can communicate through a wireless network (and/or the internet) 1450 to a remote server 1460, which can be connected to short-term data storage 1462 and/or long-term data storage 1464.

In some embodiments, sensor signals relating to the biometric and biomechanical movements of the user are transmitted to the wireless telecommunications device 1412, through a wireless network, and then through the same and/or a different wireless network, to the server. The server is preferably configured to perform processing (e.g., biometric processing) of the sensor signals. For example, the server can preferably convert the sensor output (which in some embodiments comprises position, orientation, velocity, acceleration, and/or magnetic field data) to a graphics format that illustrates the biomechanical motions performed by the user. The biomechanical motions can include, for example, the movement and rotation of the limbs and torso of the user during an athletic act. In some embodiments, the server processes the sensor signals so as to generate a graphics output that can be used by a graphical display to show the position and movements of the user's body. In other embodiments, the server can combine the sensor signal data to generate a performance "fingerprint" as further discussed herein. The server can communicate the graphics output and/or the fingerprint information through the wireless network (and/or the internet) to the telecommunications device 1412 (and/or the laptop).

In certain embodiments, the telecommunications device 1412 is configured to display the performance fingerprint or the graphics output so that the user can obtain real-time (or near real-time) feedback on his or her athletic performance or other movement. For example, the telecommunications device 1412 can be configured to display an image, graphic, movie, or video showing, e.g., the user's golf swing. The telecommunications device 1412 can also optionally display the performance fingerprint, and/or other performance metrics to enable the user to track his or her athletic or rehabilitation progress. The telecommunications device 1412 can display instructional information to improve the user's athletic performance. Many types of information can be communicated between the server, the telecommunications device 1412, and/or the laptop, and the above examples are intended as non-limiting illustrations of the types of possible information.

In some embodiments, the server 1460 stores the sensor signal data and/or the graphics output and/or the performance fingerprint information in data storage (e.g., short term storage 1462 and/or long term storage 1464) where it can be retrieved later as needed. In some embodiments, the server is configured to compare the present user data with prior user data so as to generate a performance metric indicative of the user's athletic progress. For example, the server may communicate (e.g., through the wireless network 1450) graphics output of a prior golf swing by the user (or by a professional or an instructor or a coach) to be compared with the present golf swing of the user.

In some embodiments, the data storage comprises short term data storage and long term data storage. For example, certain data may be stored in short term data storage 1462 for easy retrieval (e.g., the short term storage may comprise an array of hard disks having fast access times), while other data may be stored in long term data storage 1464 (e.g., an archival data storage system that may comprise, for example, hard disks, optical disks, magnetic tapes, etc.). The server 1460 in some implementations is configured to access the data storage to perform data mining operations designed to extract implicit, previously unknown, and potentially useful information from the data. For example, the server 1460 may mine the stored data for correlations among performance fingerprints. After finding a group of users with similar performance fingerprints, the server can communicate this information to, for example, a coach, an athletic gear manufacturer, or other product or service provider, which can then efficiently offer suitable products and/or services to the group.

The stored data can be mined for biometric, biomechanical, medical, performance, and marketing information related to the users of the system. Many examples are possible, and the following are intended to be non-limiting. The data may be retrieved for segmentation studies of the types of athletes who use the system. The data may be mined for marketing related purposes, such as to gather sell-through data, to obtain customer relationship management ("CRM") data, to provide bundled products and devices having sports content and/or a biometric theme (e.g., a golf phone with golf content cards, ring tones, wallpapers designed to match the user's performance fingerprint or other stored data). The CRM data and the sell-through data can be further mined, for example, to deliver targeted offers, updates, incentives, rebates, and/or upgrades to selected users.

In some embodiments, the user can communicate with one or more web sites that offer content, instruction, products, and/or services related to sports, athletics, exercise, and/or biometric and biomechanical applications. The user can access the web site(s) via the telecommunications device 1412 and/or a computer (e.g., the laptop 1440). Data related to the user's web site access (e.g., CRM data and/or sell-through data) can be stored on the data storage system and then tracked and mined. It is recognized that many marketing, advertising, and promotional opportunities are provided by the user performance data and web site(s) access data that can be stored by the storage device and processed or mined by the server.

IV. Biometric and Biomechanical, Data Services System

Figure 15:
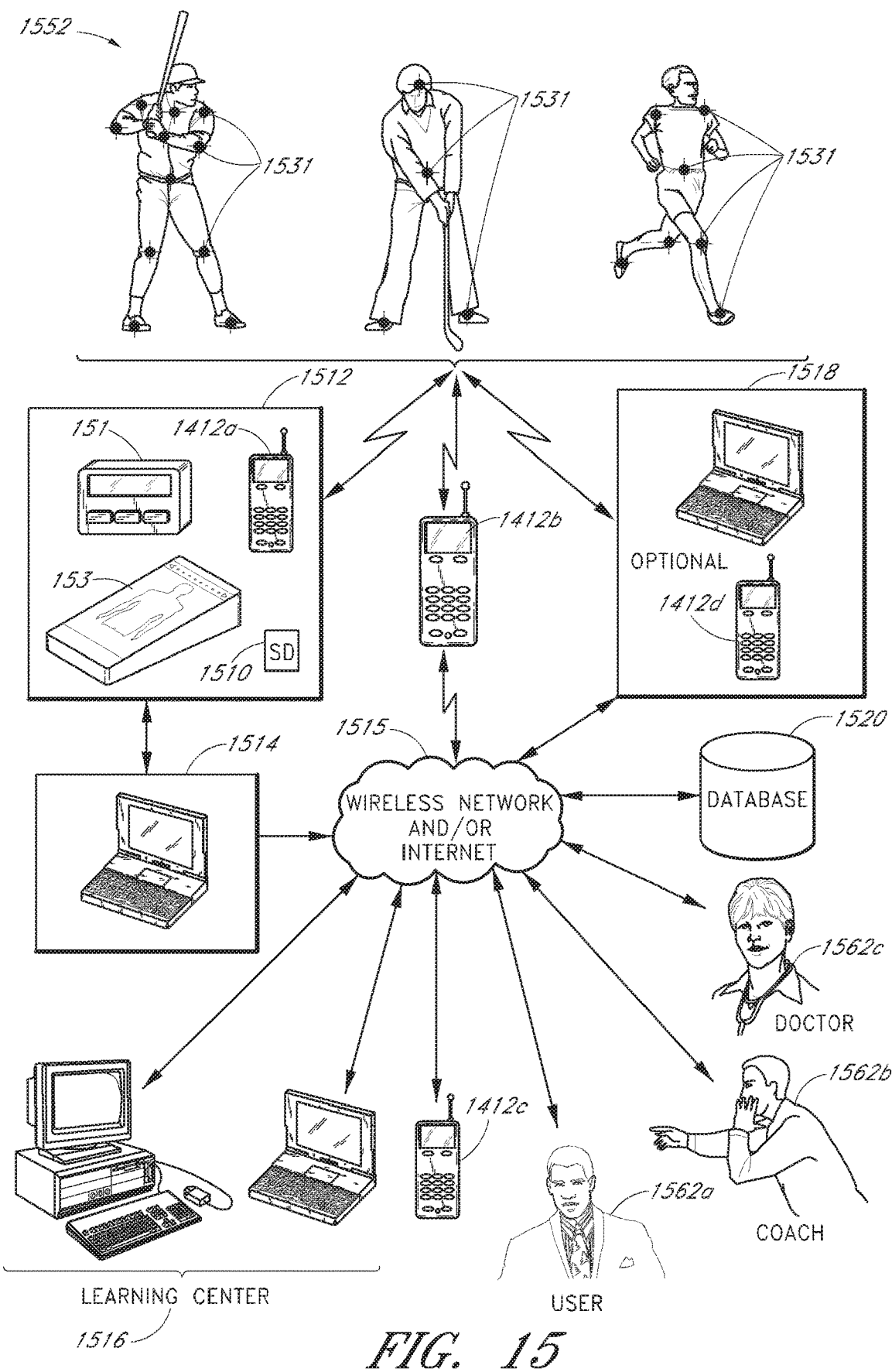
FIG. 15 schematically illustrates various examples of systems according to the present disclosure.

FIG. 15 illustrates further examples and embodiments of a system, including optional combinations of components. Users 1552, such as baseball or softball players, golfers, runners, and the like, can attach one or more sensors 1531 to portions of their body to collect and/or process biometric data. In some embodiments, the users 1552 are examples of the subject 120 (FIG. 1). In some embodiments, the users 1552 are also examples of the first user 152 (FIG. 1). The biometric data can be intercommunicated among some or all of the various components of the system as shown by the examples in FIG. 15.

In some embodiments, the biometric data is communicated to one or more devices 1512 such as, for example, the MCU 141, the interface device 153, and/or a wireless telecommunications device 1412 a (e.g., a cell phone). The devices 1512 are examples of the first processor 150 (FIG. 1). In some embodiments, the devices 1512 include a storage device 1510 such as a flash memory device (e.g., an SD memory card) that can be used to store the data for transport to another hardware device (e.g., a computer such as a laptop computer). The device 1512 can also include a component that performs biometric data processing or data packaging, transmission, or reception. For example, the processing component may be an add-on or built-in feature of the telecommunications device 1412 a (e.g., a card inserted into a card slot in a cell phone). In some embodiments, the storage device 1510 is combined with one of the other devices 1512 so that a wireless or other connection is not necessary. Data can be stored on the storage device 1510 and manually transported when the storage device 1510 is decoupled from a slot in another device (such as a slot in the MCU 141 or the cell phone 1412*a*, for example).

With further reference to FIG. 15, biometric data can be communicated to a processor 1514 (e.g., a desktop or laptop computer), which is an example of the second processor 160 (FIG. 1). In other embodiments, biometric information is additionally (or optionally) communicated through the internet (or a wireless network) 1515 to other processors or devices. For example, the biometric information can be communicated through the internet 1515 to a learning center 1516 (which may be a web-based computer system). The learning center 1516 can comprises processors and server computers that also are examples of the second processor 160. The second user 162 can access the biometric information in the learning center 1516. For example, some examples of the second user 162 include the subject 120 (FIG. 1) (which can be the user 1552), the user him or herself 1562*a* (which can be the same as the user 1552), a coach or instructor 1562*b*, a doctor, physician, sport psychologist, or trainer 1562*c*, etc. In various embodiments, the biometric data can be stored in a storage device 1520 (e.g., stored in a database). In some embodiments, the data is stored in a database 1520 before being made available to a learning center 1516.

In some embodiments, the biometric data can be transferred to a device 1518 such as a computer (e.g., a laptop computer) and/or a telecommunications device 1412*d*. The device 1518 can communicate the biometric information to, e.g., the learning center 1516 and/or the users 1562*a*-1562*c*, and/or the database 1520 substantially similarly as described above. In this embodiment, either the device 1518, the telecommunications device 1412*d*, or a combination of both can be the first processor 150, and can perform some of the functions described above with respect to the MCU 141, for example.

In some embodiments, the user 1552 can have a device such as the cell phone 1412*b* that performs both the role of the first processor 150—by obtaining data from the sensors 1531 and relaying it to a database 1520 and or a web-based learning center 1516—and also allows the user 1552 to access the learning center 1516 via the web 1515. For example, a golfer can upload data relating to a golf swing, that data can be processed, and the results can be relayed back to the golfer by way of the screen on the golfer's telecommunications device 1412*b*.

In certain embodiments, the user 1552 can utilize a telecommunications device 1412*b* (e.g., a cell phone and/or personal digital assistant) to communicate biometric data through a wireless network (and/or the internet) to the learning center 1516, other telecommunications devices 1412*c*, other computers, processors, storage devices, etc. In some embodiments, the second user 162 (e.g., another user 1562*a*, the coach 1562*b*, or the doctor 1562*c*) can use a telecommunications device 1412*c* to communicate with the first user 152 (e.g., the person 1552 engaged in the athletic activity). The second user 162 can, for example, view the biometric data from the user 1552 (e.g., at the learning center 1516 or on a computer, or on a display screen of the telecommunications device 1412*c*), and then can further use the telecommunications device 1412*c* to give personalized recommendations, instructions, coaching, and/or diagnosis to the user 1552.

In some embodiments, the first user 152 (e.g., any of the example users 1552 shown in FIG. 15) can communicate with the second user 162 (e.g., any of the example users 1562*a*-1562*c*) via the telecommunications device 1412*b*. This communication is preferably a wireless communication and can include not only the usual voice communication between the first and second users 152 and 162, but more particularly can include audible and/or visual communication regarding biometric information (e.g., graphics or a performance fingerprint) that is displayed on, for example, the telecommunications devices 1412*b* and 1412*c*. In this manner, the second user 162 and the first user 152 can use a pair of telecommunications devices 1412*b* and 1412*c* to share biometric information, recommendations, and instruction at any suitable time and/or place. Additionally, in various embodiments, the user 1552 can share his or her biometric information with other users, friends, teammates, parents, children, etc. via one or more telecommunications devices 1412*a*-1412*d*. Since the biometric data is stored in the storage device 1520 in many embodiments, the users 152 and 162 can retrieve, analyze, compare, process, and discuss biometric information acquired at earlier times and/or places. The various users 152, 162 can examine the current and prior biometric information to, for example, assess performance improvements and intercompare performances (e.g., between users or between a user and a coach, a professional athlete, etc.).

Accordingly, certain preferred embodiments of the system permit the various first and second users 152 and 162 to preserve and share biometric data, performance data, graphical views, performance fingerprints, assessment data via any of the devices shown in FIG. 15 (e.g., via cell phones, laptop computers, the Internet) so as to empower the users 152, 162 to feel and stay connected whenever, wherever, and however they need to. Embodiments of the system provide a verbal and visual connection, which allows users to share needs, ideas, and emotions so as to further increase feelings of connection. Users can utilize features of the system to stay genuinely and affirmatively connected to performance assessment, coaches, and trainers through the connectivity provided by embodiments of the present system.

A biometric and biomechanical data services provider (e.g., the provider of the sensors 1531, the operator of a website, the server 1460 (FIG. 14), the storage systems (FIGS. 14, 15), and the database 1520) can collect, store, and mine any of the acquired biometric data for any suitable instructional, health-related, marketing, promotional, advertising, or business objective. The biometric data can be shared among doctors, trainers, and health professionals to develop new methods to prevent or reduce injury or to help improve recovery from injury. As is apparent from FIG. 15 (and the other Figures described herein), many types of devices and many wired and wireless channels of communication are possible to share biometric and biomechanical data derived from one or more sensors 1531 among various users 1552, 1562*a*-1562*c*, devices 1412*a*-1412*c*, 1510, 1512, 1515, 1518, 1520, learning centers 1516, websites, etc. Many uses are possible and the examples discussed herein are intended to be illustrative and non-limiting.

V. Wireless Access Management Systems and Methods for Biometric Data

As described above, embodiments of the disclosed system are particularly advantageous for sharing biometric data. As used herein, biometric data can include without limitation biomechanical and biomedical data. Accordingly, it is beneficial to provide a biometric data management system architecture and protocol ("Protocol") for sharing, communicating, processing, analyzing, and otherwise using biometric data.

Figure 16:
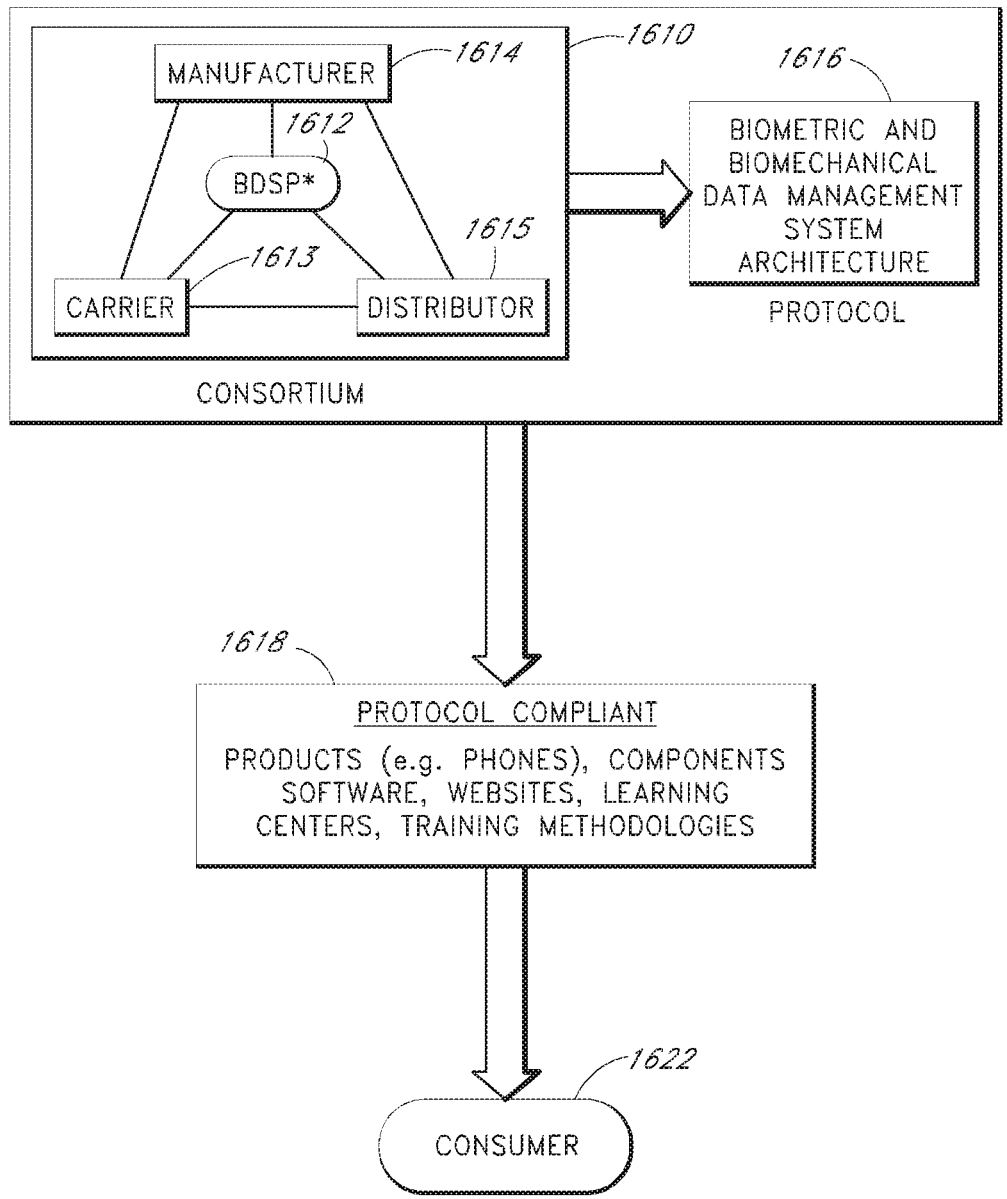
FIG. 16 is a block diagram that schematically illustrates an embodiment of a system and process for providing a biometric and biomedical data services protocol.

FIG. 16 illustrates an embodiment of a system and a process for providing a protocol 1616. In this example, a consortium 1610 comprising two or more members is formed. The central member is a biometric data services provider ("BDSP") 1612. An example BDSP is an entity that provides embodiments of the systems and methods disclosed herein. The BDSP 1612 may generally be responsible for activities such as, for example, developing, coordinating, producing, disseminating, and marketing intellectual property concepts relating generally to biometric data. For example, the BDSP 1612 may implement the systems and methods disclosed herein. The BDSP 1612 may develop sensor technology, and the mathematical algorithms and methods for converting sensor data to usable biometric performance fingerprints and/or graphics. The BDSP 1612 may develop communication standards for transmitting and receiving biometric information. For example, the BDSP 1612 may develop standards for packetizing the biometric sensor data so as to efficiently utilize available bandwidth in one or more communications channels, particularly in wireless communications channels.

In certain embodiments, the BDSP 1612 can develop hardware, firmware, and/or software usable by the components and devices of the system (e.g., any of the devices shown in FIGS. 14 and 15). For example, the BDSP 1612 may develop a hardware card that is insertable into a standard or proprietary slot on a telecommunications device that enables the device to be compatible with the Protocol. The BDSP 1612 may develop website(s), learning centers (e.g., learning center 1516 in FIG. 15), instructional tools or aids, biometric fingerprint algorithms or formulas, graphical user interfaces, interface devices such as device 163, etc.

The consortium 1610 may include one or more other members. In the example shown in FIG. 16, the consortium further includes a manufacturer 1614. The manufacturer may be a telecommunications device manufacturer such as, for example, a wireless telecommunications device manufacturer. The manufacturer 1614 may have primary responsibility for producing one or more products or devices that are compatible with the systems and methods established by the BDSP 1612.

Another member of the consortium 1610 may be a carrier such as, for example, a telecommunications carrier 1613, and in particular a wireless telecommunications carrier. The carrier 1613 may, for example, develop transmission and reception standards that are compatible with the systems and methods developed by the BDSP 1612. The carrier 1613 provides the network (e.g., a wireless network and/or internet that can be used to carry user's biometric data among the components of the system (see, e.g., FIGS. 14 and 15). The carrier 1613 may also provide websites, information, advertising, and marketing to provide easier access to products developed by the manufacturer and sold to consumers.

Another member of the consortium 1610 can be a distributor such as, for example, a distributor 1615 of telecommunications devices suitable for use on the carrier's telecommunications network. The distributor 1615 may be the direct access point by which consumers obtain products and services from the consortium 1610.

The consortium 1610 can include fewer or more members. Furthermore, the consortium 1610 can include more than one member of a particular class (e.g., more than one carrier 1613). Additionally, the consortium 1610 can include different classes than shown in FIG. 16, e.g., wholesale and retail stores, dealers, agents, etc. In some embodiments, the members of the consortium 1610 can perform some or all of the tasks described above, while in other embodiments the members of the consortium 1610 perform different tasks. The tasks may dynamically evolve as the consortium 1610 acquires new members, information, etc. In some embodiments, the members of the consortium 1610 may share responsibility for carrying out the tasks of the consortium. For example, the BDSP 1612 may coordinate the development of the Protocol 1616 by the other members of the consortium 1610. Many variations are possible.

In preferred embodiments, the consortium 1610 will produce a biometric and biomechanical data management system architecture (the protocol 1616) that comprises standards, rules, guidelines for the sharing, communication, processing, analysis, and other uses of biometric information. The protocol 1616 may reflect a consensus among the members of the consortium 810 regarding the most technologically efficient ways to share, communicate, and use the biometric data. The protocol 1616 may include compatibility standards to ensure that products and services meet the requirements of the protocol 1616. Compliance with the protocol 1616 will ensure that products developed by the consortium 1610 (e.g., by the manufacturer) are interoperable. In one embodiment, the consortium 1614 may promulgate a certification mark (or other suitable trademark or trade dress) for use on protocol-compliant products and services. In preferred embodiments, the standards of the protocol 1616 will be compliant with and generally determined by the systems and methods provided by the BDSP.

Members of the consortium 1610 generally will agree to provide products and, services that conform to the Protocol 1614. Entities not members of the consortium 1610 generally will be precluded from providing products and services that claim to be protocol compliant, without, for example, paying licensing fees or royalties to the consortium.

The consortium 1610 generally will develop a Protocol-compliant line 1618 of products and services including, for example and without limitation, goods, devices, components, hardware, firmware, software, websites, learning or training centers, training, instruction, and treatment methodologies. The consortium 1610 may develop proprietary trade secrets relating to the protocol 1614. Additionally, the consortium 1610 may develop other valuable intellectual property relating to biometric data and its uses. Typically, the protocol-compliant line 1618 will be marketed and sold to consumers 1622. An important group of consumers 1622 include the first and second users 152 and 162 of the system 110. However, in other embodiments the protocol-compliant line 1618 may be sold or marketed to non-members of the consortium 1610 for further sales or marketing to wholesalers, retailers, and/or consumers. Many variations are possible.

One embodiment relates generally to providing protocol-compliant wireless technology devices such as, for example, cellular telephones (cell phones). The cell phones may bear a mark (such as a certification mark) indicating to the consumer 1622 that the cell phone is compliant with the Protocol 1614 and can be used to share and communicate biometric data with other Protocol-compliant devices. In one embodiment, the cell phones can be delivered straight to consumers, activated, protocol-compliant, and ready to use. In some embodiments, the cell phones may include internal or external devices or components manufactured by a member of the consortium 1610 so that the cell phone can reliably and efficiently transmit biometric data over the member carrier's network. In certain embodiments, the BDSP 1612 markets cell phones to the consumer 1622. The carrier may permit a consumer 1622 to keep his or her current cell phone number when purchasing a protocol-compliant cell phone. Some cell phones may include sports-specific content (e.g., a golf or baseball phone with suitable content cards, ring tones, and/or wallpapers). In some embodiments, the cell phone is a disposable or prepaid cell phone. When a consumer 1622 buys a cell phone from the BDSP 1612 and subscribes to the carrier's telecommunications network, the BDSP 1612 may retain a fee for providing a customer to the carrier. In other embodiments, the members of the consortium 1610 may adopt a range of methods for sharing income streams, license fees, royalties, etc. among themselves.

The consortium 1610 may capture and store CRM data and sell-through data, regarding the access, use, and purchase of goods and services on websites operated by the consortium 1610 or by its individual members. Data mining operations can examine and extract information and correlations between CRM data, sell-through data, and biometric data. For example, the data mining operations may indicate that, for example, golfers having a performance fingerprint within a certain range (e.g., corresponding to a particular skill level) may preferentially purchase golf equipment from one or a small group of suppliers. The consortium 1610 can provide such information to the suppliers (for a suitable fee or royalty) so that the suppliers can directly market or advertise to such golfers. It is apparent that many marketing variations are possible.

In some embodiments, the consortium 1610 may desire to fulfill some or all of the following objectives: providing Protocol-compliant products and services to consumers, minimizing cross-shopping within carrier channels, driving post-sale accessory and content purchases, facilitating analysis of promotional campaigns, building consortium 1610 brand equity with consumers 1622, collecting CRM data to facilitate continuous marketing dialog/relationship/research, bundling devices with sports specific content, targeting products and services to certain segments of the consumer market, providing offers, incentives, and rebates to premium customers, or other suitable objectives.

FIG. 16 illustrates one example embodiment of a consortium 1610 that promotes a Protocol 1616 and protocol-compliant goods and services 1618 to consumers 1622. Many variations are possible, and the illustration in FIG. 16 is intended as one non-limiting example.

VI. Applications for Military and Police Enforcement Entities

Some embodiments are systems with multiple devices (which can be used, for example, by military entities such as dismounted soldiers or by police entities such as a SWAT team or by other first responders such as firefighters, emergency response technicians, etc.). The devices can be designed to operate in a local area network so that a group of devices can be monitored in real time while interacting with each other (e.g., on the battlefield). A time division multiplex system can be used to allow monitoring of some or all of the devices and communication with individual units and or groups through the devices. Sensors can be miniaturized, attached to human bodies, and adapted to incorporate a tactile feed back system for bi-directional communication of real time graphics. For this application, sensors can be advantageously low-power. Adding additional sensors can provide additional information for monitoring the stance and/or status of a human: standing, sitting, prone, firing position, injured position, biological/medical vital signs, etc. Signals can be transmitted in code or using a modified sign language to represent many of the same commands that are used where visual communication is used. For example, if a certain arm or finger position has a visual meaning between soldiers, that same arm or finger position can be used and monitored by sensors even when that signal is not directly visible to the other soldier.

Sensors can be incorporated into the combat attire of soldiers to allow collection of individual location and action information. That information can later be presented to a unit commander, for example. Such information can be useful in showing heroism of a soldier or investigating alleged criminal behavior by a soldier, for example. To demonstrate the technology, a system can be configured to interface with current communication systems. In some advantageous embodiments, a device that accompanies a soldier is battery-operated and has power-conservation features. The device's radio interface advantageously supports both standard microphone and data interface modes, enabling the user to select the mode of operation.

In the data mode, the transmitted data can be packetized, coded, multiplexed, or otherwise modulated to minimize the amount of data transmitted and the length of transmission time, while at the same time reporting the relevant information such as location of the user, body position, vitals, etc. Transmitted data can be sent or broadcast by each user (e.g., each soldier, war fighter, law enforcement personnel, etc.), and the data can be stored by the communication system. Data from users that are out of range (e.g., if a user's signal is being blocked by a structure or terrain) can be forwarded to another user that is within the signal range (and field of view, if line-of-sight methods are used) of both units. In some advantageous embodiments, each user can visibly see the location (and/or other information) of other users on a display system, which can include security settings to make sure that information is safe. The display system can be hand-held or mounted to be seen by a user hands-free.

In some embodiments, a unit commander can send and receive commands to a group or individual users using brevity codes, which provide shortened commands without concealing the content of the commands. The brevity codes can control signaling devices. Signaling devices can include vibration, tactile stimulus, and/or devices that are attached to a mouth type of teeth retainer that can modulate or vibrate a tooth or jaw. For example, a Morse code message or other coded sequence could be transmitted to the signaling device.

A. Mouthpiece Signaling Device

Figure 17A:
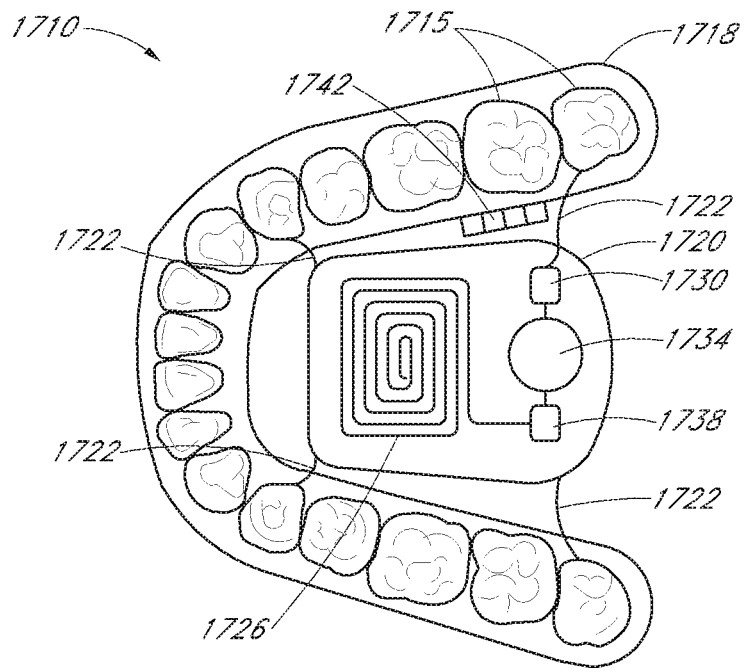
FIG. 17A is a top-view that schematically illustrates a signaling device that can be placed in a user's mouth.

FIG. 17A is a top-view that schematically illustrates a signaling device 1710 that can be placed in a user's mouth. In some embodiments, the signaling device 1710 includes a tooth retainer 1718 much like those used to straighten teeth. The retainer 1718 may be configured to snap into a user's mouth to position a miniature audio and/or tactile transducer 1742 near, for example, the rear teeth 1715, gum, or jaw bone. The retainer 1718 may be attached to the user's upper teeth or lower teeth. In some implementations, retainers 1718 for both the upper and the lower teeth are used. It is advantageous to attach the retainer 1718 to the user's upper teeth to provide a substantially free range of movement of the user's tongue, which allows the user to speak, eat, and drink more naturally.

The signaling device 1710 schematically illustrated in FIG. 17*a* comprises a base 1720 that is attached to the retainer 1718 by one or more clips 1722. The base 1720 may be shaped so as to conform to the user's mouth or palate and may advantageously be flexible to be more comfortable to wear. The base 1720 can be used to support and position electronic circuitry within the user's mouth. In some embodiments, the base 1720 comprises a flexible printed circuit board (PCB) to electrically connect electronic components of the device 1710. Although the electronic circuits are shown in FIG. 17*a* as disposed on the base 1720, in other embodiments, the circuits are disposed in or on the retainer 1718. Such embodiments beneficially may provide less of an impediment to speech and eating by the user.

The signaling device 1710 can contain microcircuits (e.g., disposed in or on the base 1720) similar to those present in radio frequency identification (RFID) technology. Power can be supplied to the microcircuits by an internal and/or an external power supply. In the embodiment depicted in FIG. 17*a*, the device 1710 comprises a microcontroller 1730, a signal discriminator 1738, an internal power source 1734, and an RF antenna 1726, which are disposed on the base 1720. The microcontroller 1730 is used to control and coordinate the functions and operation of the device 1710. The microcontroller 1730 may be configured to decode or decrypt coded signals. The power source 1734 may include a battery and/or a capacitive storage device, such as a supercapacitor. In some embodiments, the device 1710 utilizes an external power source, and the internal power source 1734 is used for backup and/or standby power needs. In such embodiments, the internal power source 1734 can be charged by the external power source.

The embodiment of the device 1710 shown in FIG. 17*a* also includes a vibrator or modulator 1742 that provides a tactile stimulus to a portion of the user's mouth. The modulator 1742 may be disposed near the user's teeth, gums, or jawbone. In the embodiment shown in FIG. 17*a*, the device 1710 is configured so that the modulator 1742 is disposed adjacent the rear teeth 1715 of the user. The modulator 1742 vibrates in response to signals from the microcontroller 1730, and the user detects the vibrations in his or her teeth and/or gums. In some embodiments, more than one modulator 1742 is used. For example, the device 1710 may include modulators 1742 disposed on the right and the left sides of the user's mouth, or the front and the back of the mouth. Multiple modulators 1742 are advantageously used in applications where signals from different senders are communicated to the user. For example, a first modulator may indicate signals from a central command post, while a second modulator may indicate signals from a field command post. Many variations are within the contemplation of the present disclosure.

Information such as, e.g., data, commands, and messages, can be communicated to the signaling device 1710, which is configured to communicate this information to the user through one or more modulators 1742. For example, the device 1710 can be configured to receive radio frequency (RF) signals transmitted from an external transmitter, transceiver, or antenna. For example, in one implementation, the external transmitter comprises a broom-like microphone device including a transmitter circuit and a small antenna. The broom-like microphone picks up voice commands to be transmitted from a sender to the user of the device 1710. In various implementations, the microphone and transmitter are integrated into an existing radio assembly used by the sender, e.g., a unit commander, or are integrated into a head set worn by the sender. The microphone and/or transmitter can be powered by, for example, a battery pack worn by the sender. In some implementations, the biomechanical sensors described herein are used to detect body movements of the sender (or sequences of body movements), for example, hand signals, which are converted into suitably coded signals by a controller (e.g., the MCU of FIG. 1), and then transmitted to the user (e.g., via an RF signal). In a preferred embodiment, the transmitted information includes both voice commands and body movement commands.

The transmitter circuit may transmit signals electromagnetically by means of an RE carrier plus a modulated sub-carrier that includes the information to be communicated to the user. In some applications, the carrier is rectified, and electromagnetic energy in the transmitted signal is used to charge the power source 1734. The antenna 1726 of the device 1710 can receive the RF signals transmitted by the RF transmitter. Information may be transmitted from remote locations via satellite or other suitable communications link (e.g., a digital RF link).

The transmitted signal can include information, data, messages, commands, etc., which may be encoded via Morse or brevity codes. The signal may be encrypted in some cases. The antenna 1726 receives the transmitted signal. In applications wherein the signal is transmitted via an RF carrier and a modulated sub-carrier, the RF carrier typically is present during both the transmission and the reception of the signal. The microcontroller 1730 can be used to decode the information carried by the sub-carrier signal. In some implementations, information is transmitted via the sub-carrier signal at a relatively low rate so that the microcontroller 1730 can decode bit sequences suitable for communicating minimal command sequences. In certain such implementations, data can be sent to the microcontroller 1730 while the transmit carrier is present, if the microcontroller 1730 is configured to request the data from the transmitter. In some embodiments, the device 1710 includes a transceiver that can be used to establish bi-directional communications. For example, the transceiver can request data at a polled rate from one or more sources of transmitted signals.

As depicted in FIG. 17*a*, the signal received by the antenna 1726 is communicated to the signal discriminator 1738, which decodes the received signal. For example, the decoded signal may include a binary sequence of "1's" and "0's." The decoded signal is communicated to the microcontroller 1730, which can determine the message or command contained in the decoded signal (e.g., by processing the binary sequence). In some applications, the information may have been encrypted, and the microcontroller 1730 may decrypt the received information.

The microcontroller 1730 is configured to provide a signal to the modulator 1742 in the user's mouth so as to provide a physical sensation capable of being perceived by the user. The modulator 1742 shown in FIG. 17*a* is a vibrator that vibrates in response to the signal, and the vibrations can be felt by the user's teeth or jawbone, for example. In some embodiments, the vibration of the teeth is at a frequency (e.g., 1000 Hz) capable of being perceived in the user's inner ear as the vibrations propagate to the inner ear through oral and nasal bony structures. In some embodiments, the modulator 1742 causes a physical sensation in the mouth. The type and magnitude of the physical sensation can depend on the frequency of modulator vibrations. In some embodiments, vibrations can be directional (e.g., a right vibration or a left vibration). By perceiving the physical sensation, the user can determine the information transmitted by the sender. In some embodiments, multiple modulators 1742 are used, for example, a modulator 1742 on the left side and the right side of the user's mouth. Each such modulator 1742 may cause a distinctive physical sensation (e.g., a vibration), and the physical sensations may be different for different modulators 1742. Multiple modulators 1742 advantageously may be used, for example, to communicate information from multiple transmission sources (e.g., a central command post and a field command post) or from different parts of a battlefield.

Signals transmitted to multiple modulators 1742 may indicate to the user a desired or commanded direction of movement (or other action). For example, in one implementation, the modulator 1742 provides a physical sensation to indicate whether the user should move forward, backward, right, or left. Additional or alternative user actions can be indicated by the modulator 1742 as well, e.g., stand up, lie down, halt, run, return to a base, etc. It will be recognized that many types of commands, actions, and movements can be indicated to the user by the modulator 1742.

Figure 17B:
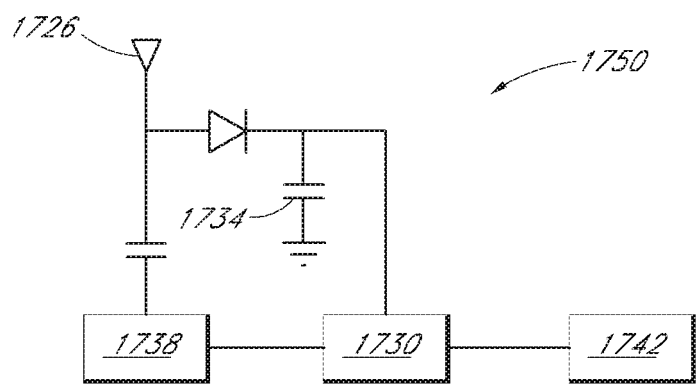
FIG. 17B schematically illustrates an embodiment of a circuit that can be used with the signaling device illustrated in FIG. 17A.

FIG. 17*b* schematically illustrates an embodiment of a circuit 1750 that can be used with the signaling device 1710, The circuit 1750 comprises the antenna 1726, the internal power source 1734 (depicted as a capacitor, e.g., a supercapacitor), the signal discriminator 1738, the microcontroller 1730, and the modulator 1742. In this embodiment of the circuit 1750, the antenna 1726 receives a signal transmitted by a sender (e.g., an RF signal). The discriminator 1738 decodes the received signal into, e.g., a binary sequence. The microcontroller 1730 interprets the binary sequence as commands, data, or messages to be communicated to the modulator 1742, which causes a sensory effect in the user's mouth in response to the commands, data, or messages. The sensory effect is perceivable by the user (e.g., as a vibration in the mouth or as a sound in the ear) and conveys the commands, data, or messages to the wearer.

The systems and devices described in detail above with respect to sports applications can also be used for military applications. As described above, depending on the number of sensors and types of sensors, a body limb can be measured with 3-dimensional representation. Advanced motion sensor devices can measure acceleration, rotation, speed and direction. Biometric sensors can measure heart rate, body temperature, etc. With multiple motion sensors, the human body position can be monitored and measured, while transmitting the position in real time. For example, the sensors and sensor configurations that can be used to improve a golf swing or baseball form can also be used to indicate that a soldier is standing, sitting, firing, or in an injured position. This information can be displayed on local and/or remote display units in real time and simulated playback mode. The position or movement of arms, head, legs, etc. can be used to signal and or indicate a response to a command. Thus, a soldier in remote communication with his commander using this system can acknowledge receipt of instructions with a silent nod of the head, detectable by the body movement sensors. The sensor sampled data at the originating user can be converted to digital data and sent to a central communication system to be digitally transmitted to the field unit commander. In some embodiments, the sensor data can be relayed to a remote command center. In addition to body position, health, etc., the speed and direction of a user can be reported by including GPS capabilities. Preferably, the system can be used to communicate with a user through coded signaling devices that can instruct the wearer or user to perform actions without using audio voice transmission.

Certain objects and advantages of the inventions are described herein. It is to be understood that not necessarily all such objects or advantages may be achieved in accordance with any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed, herein, the acts or operations making up the method/process may be performed in any suitable sequence and are not necessarily limited to any particular disclosed sequence.

The foregoing description sets forth various preferred embodiments and other exemplary but non-limiting embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Accordingly, the scope of the inventions disclosed herein is to be determined according to the following claims and their equivalents.

What is claimed is:

1. A garment comprising:
    two or more sensors contained within the garment and configured to gather data on a stance and/or a movement of a wearer of the garment undertaking a physical activity; and
    one or more actuators configured to provide haptic feedback to the wearer of the garment, wherein:
        the sensors are respectively associated with different joints of the wearer, and the sensors are configured to transmit the data to a processor for generation of instructions for the wearer, wherein the instructions are based on data from each of the sensors associated with the different joints; and
        the one or more actuators provide the haptic feedback to the wearer, the haptic feedback corresponding to the instructions for the wearer as—generated by the processor.

2. The garment of claim 1, wherein the instructions for the wearer comprise movement instructions for the wearer to move in a specified manner.

3. The garment of claim 2, wherein a characteristic of the haptic feedback depends on the specified manner in which the wearer is instructed to move.

4. The garment of claim 1, wherein the instructions for the wearer comprise movement instructions for the wearer to change a posture or stance.

5. The garment of claim 1, wherein the one or more actuators are contained within the garment.

6. The garment of claim 1, wherein the one or more actuators are coupled to the garment.

7. The garment of claim 1, wherein:
    the one or more actuators are contained within the garment;
    the instructions for the wearer comprise instructions for the wearer to move one or more body parts of the wearer; and
    a type of the haptic feedback depends on the specified manner in which the wearer is instructed to move.

8. A system configured to be worn by or coupled to a human body, the system comprising:
    two or more sensors configured to sense information about a position of at least a portion of the human body, wherein the sensors are associated with respective different body joints;
    one or more transducers configured to provide a tactile stimulus to the human body; and
    a processor configured to:
        receive, from the two or more sensors associated with the respective different body joints, the information about the position of at least a portion of the human body and,
        provide instructions to the one or more transducers to provide the tactile stimulus to the human body, wherein the instructions are based on the information from the two or more sensors associated with the respective different body joints.

9. The system of claim 8, wherein the sensors are coupled to a garment wearable by the human body.

10. The system of claim 8, wherein the one or more transducers include a vibrator.

11. The system of claim 8, wherein the one or more transducers include an audio transducer.

12. The system of claim 8, wherein the one or more transducers are coupled to a mouthpiece.

13. The system of claim 8, wherein the processor is configured to provide a command signal to the one or more transducers to provide the tactile stimulus to thereby indicate movement instructions for the human body.

14. The system of claim 8, wherein the processor is configured to provide a command signal to the one or more transducers to provide the tactile stimulus to thereby indicate instructions for the human body to change posture.

15. The system of claim 8, further comprising a garment, wherein the sensors and the one or more transducers are coupled with the garment.

16. A system comprising:
    two or more sensors configured to sense information about a position of at least a portion of a human body, wherein the sensors are associated with respective different body joints;
    one or more actuators configured to produce a tactile effect on a user;
    a communication circuit;
    a processor configured to control the one or more actuators and the communication circuit; and
    a first external device having a user interface and instructions operating thereon configured for at least causing the first external device:
        to communicate with the processor via the communication circuit to thereby control the one or more actuators in response to the sensed information from the sensors, wherein the sensed information includes information from each of the sensors associated with the respective different body joints; and
        to receive user instructions from the user interface to cause the one or more actuators to produce the tactile effect.

17. The system of claim 16, wherein the instructions are configured to cause the first external device to receive user instructions from the user interface about a type of tactile effect to produce for the user.

18. The system of claim 17, wherein the type of the tactile effect indicates a corresponding type of movement or posture change for the user to perform.

19. The system of claim 16, further comprising a garment that includes the one or more actuators, the communication circuit, and the processor.

20. The system of claim 16, wherein the one or more actuators comprise at least one of a vibrator, an audio transducer, and a mouthpiece transducer.

* * * * *